(12) United States Patent
Fan et al.

(10) Patent No.: US 9,518,026 B2
(45) Date of Patent: Dec. 13, 2016

(54) **5-AMINOPYRAZOLE-4-CARBOXAMIDE INHIBITORS OF CDPK1 FROM *T. GONDII* AND *C. PARVUM***

(71) Applicant: UNIVERSITY OF WASHINGTON THROUGH ITS CENTER FOR COMMERCIALIZATION, Seattle, WA (US)

(72) Inventors: Erkang Fan, Seattle, WA (US); Wesley C. Van Voorhis, Seattle, WA (US); Zhongsheng Zhang, Seattle, WA (US); Wenlin Huang, Seattle, WA (US); Kayode K. Ojo, Seattle, WA (US)

(73) Assignee: University of Washington Through its Center For Commercialization, Seattle, WA (US)

( * ) Notice: Subject to any disclaimer, the term of this patent is extended or adjusted under 35 U.S.C. 154(b) by 0 days.

(21) Appl. No.: 14/891,237

(22) PCT Filed: May 20, 2014

(86) PCT No.: PCT/US2014/038813
§ 371 (c)(1),
(2) Date: Nov. 13, 2015

(87) PCT Pub. No.: WO2014/189947
PCT Pub. Date: Nov. 27, 2014

(65) Prior Publication Data
US 2016/0090362 A1  Mar. 31, 2016

Related U.S. Application Data

(60) Provisional application No. 61/825,364, filed on May 20, 2013, provisional application No. 61/889,451, filed on Oct. 10, 2013.

(51) Int. Cl.
| | |
|---|---|
| *C07D 217/00* | (2006.01) |
| *C07D 231/38* | (2006.01) |
| *C07D 311/20* | (2006.01) |
| *C07D 235/08* | (2006.01) |
| *C07D 235/12* | (2006.01) |
| *C07D 487/04* | (2006.01) |
| *C07D 231/14* | (2006.01) |
| *C07D 401/04* | (2006.01) |
| *C07D 401/06* | (2006.01) |
| *C07D 403/04* | (2006.01) |
| *C07D 405/04* | (2006.01) |
| *C07D 405/14* | (2006.01) |

(52) U.S. Cl.
CPC .......... *C07D 231/38* (2013.01); *C07D 231/14* (2013.01); *C07D 235/08* (2013.01); *C07D 235/12* (2013.01); *C07D 311/20* (2013.01); *C07D 401/04* (2013.01); *C07D 401/06* (2013.01); *C07D 403/04* (2013.01); *C07D 405/04* (2013.01); *C07D 405/14* (2013.01); *C07D 487/04* (2013.01)

(58) Field of Classification Search
CPC ..................................................... C07D 231/38
USPC ........................................................ 546/139
See application file for complete search history.

(56) References Cited

U.S. PATENT DOCUMENTS

| | | | | |
|---|---|---|---|---|
| 5,922,741 | A | * | 7/1999 | Davis .................. C07D 231/38 514/341 |
| 7,307,097 | B2 | | 12/2007 | Adams et al. |
| 2016/0090362 | A1 | | 3/2016 | Huang et al. |

FOREIGN PATENT DOCUMENTS

| | | |
|---|---|---|
| WO | 97/40019 A1 | 10/1997 |
| WO | 2007/025540 A1 | 3/2007 |
| WO | 2007/025540 A2 | 3/2007 |
| WO | 2011/094628 A1 | 4/2011 |
| WO | 2012/127212 A1 | 9/2012 |

OTHER PUBLICATIONS

Thaher et al. Journal of Medicinal Chemistry (2012), 55(2), 961-965.*
Venkatesh et al., J. Pharm. Sci. 89, 145-54 (2000).*
Dorwald F. A. Side Reactions in Organic Synthesis, 2005, Wiley: VCH, Weinheim p. IX of Preface p. 1-15.*
Huang et al. Medicinal Chemistry Letters (2015), 6(12), 1184-1189.*
Ajjampur, et al., "Closing the diarrhoea diagnostic gap in Indian children by the application of molecular techniques," J Med Microbiol, vol. 57, pp. 1364-1368, 2008.
Bishop, et al., "Generation of Monospecific Nanomolar Tyrosine Kinase Inhibitors via a Chemical Genetic Approach," J. Am. Chem. Soc., vol. 121, pp. 627-631, 1999.
International Search Report PCT/US2014/038813, mailed Aug. 11, 2014.
Bobko, et al., "Novel Synthesis of 5-Amino-3-bromo-1-(tert-butyl)-1H-pyrazole-4-carbonitrile: A Versatile Intermediate for the Preparation of 5-Amino-3-aryl-1-(tert-butyl)-1H-pyrazole-4-carboxamides," Org. Lett., vol. 14, pp. 3906-3908, 2012.
Castellanos-Gonzalez, et al., "A Novel Calcium-Dependent Protein Kinase Inhibitor as a Lead Compound for Treating Cryptosporidiosis," Journal Infect Dis , vol. 208, pp. 1342-1348, 2013.
Johnson, et al., "Development of Toxoplasma gondii calcium-dependent protein kinase 1 (TgCDPK1) inhibitors with potent anti-toxoplasma activity," J Med Chem, vol. 55, No. 5, pp. 2416-2426, 2012.
Kroe, et al., "Thermal Denaturation: A Method to Rank Slow Binding, High-Affinity P38α MAP Kinase Inhibitors" Journal of Medicinal Chemistry 2003, vol. 46, No. 22, pp. 4669-4675, 2003.
Larson, et al., "Multiple determinants for selective inhibition of apicomplexan calcium-dependent protein kinase CDPK1," J. Med. Chem., vol. 55, pp. 2803-2810, 2012.

(Continued)

*Primary Examiner* — Nizal Chandrakumar
(74) *Attorney, Agent, or Firm* — McDonnell Boehnen Hulbert & Berghoff LLP

(57) ABSTRACT

The present disclosure is generally directed to compositions and methods for treating apicomplexan protozoan related disease, such as toxoplasmosis and cryptosporidiosis.

16 Claims, 4 Drawing Sheets

(56) References Cited

OTHER PUBLICATIONS

Lebakken, et al., "Development and Applications of a Broad-Coverage, TRFRET-Based Kinase Binding Assay Platform," J. Biomol. Screen., vol. 14, pp. 924-935, 2009.
Lourido, et al., Calcium-dependent protein kinase 1 is an essential regulator of exocytosis in Toxoplasma, Nature, vol. 465, pp. 359-362, 2010.
Lourido, et al., "Optimizing small molecule inhibitors of calcium-dependent protein kinase 1 to prevent infection by Toxoplasma gondii," Journal of Medicinal Chemistry, vol. 56, 2013.
Markwalder, et al., "Synthesis and Biological Evaluation of 1-Aryl-4,5-dihydro-1H-pyrazolo[3,4-d]pyrimidin-4-one Inhibitors of Cyclin-Dependent Kinases," Journal of Medicinal Chemistry, vol. 47, No. 24, pp. 5894-5911, 2004.
Montoya, et al., "Toxoplasma," In Mandell, Douglas, & Bennett's Principles and Practice of Infectious Diseases, Chapter. 279, pp. 3495-3526. 2010.
Murphy, et al. "Discovery of Potent and Selective Inhibitors of CDPK1 from C. parvum and T. gondii," ACS Medicinal Chemistry Letters, vol. 1, No. 7, pp. 331-335, 2010.
Ojo, et al, "A Specific Inhibitor of PfCDPK4 Blocks Malaria Transmission: Chemical-genetic Validation," Journal Infect Dis, vol. 209, pp. 275-284, 2014.
Ojo, et al., "Toxoplasma gondii calcium-dependent protein kinase 1 is a target for selective kinase inhibitors," Nat Struct Mol Biol, vol. 17, No. 5, pp. 602-607, 2010.
Ojo, et al., "Transmission of malaria to mosquitoes blocked bump kinase inhibitors," The Journal of Clinical Investigation, vol. 122, No. 6, pp. 2301-2305, 2012.
Pargellis, et al., "Inhibition of p38 MAP kinase by utilizing a novel allosteric binding site," Nat. Struct. Mol. Biol., vol. 9, pp. 268-272, 2002.
Samie, et al., "Cryptosporidium species: preliminary descriptions of the prevalence and genotype distribution among school children and hospital patients in the Venda region, Limpopo Province, South Africa," Exp Parasitol, vol. 114, No. 4, 314-322, 2006.
Sato, et al., "Enantioselective synthesis of substituted 3-quinolyl alkanols and their application to asymmetric autocatalysis," Synthesis, vol. 9, pp. 1419-1428, 2004.
Schwartzman, et al., "Toxoplasmosis," In Tropical Infectious Diseases: Principles, Pathogens and Practice, pp. 722-728, 2011.
Sugi, et al., "Use of the Kinase Inhibitor Analog 1NM-PP1 Reveals a Role for Toxoplasma gondii CDPK1 in the Invasion Step," Eukaryotic Cell, vol. 9, No. 4, pp. 667-670, 2010.
Wernimont, et al., "Structures of apicomplexan calcium-dependent protein kinases reveal mechanism of activation by calcium," Nat. Struct. Mol. Biol., vol. 17, pp. 596-601, 2010.
White, et al., "*Cryptosporidium* Species" In Mandell, Douglas, & Bennett's Principles and Practice of Infectious Diseases, Chapter. 283, pp. 3547-3560, 2010.
Zhang, et al., "A second-site suppressor strategy for chemical genetic analysis of diverse protein kinases," Nat. Meth., vol. 2, pp. 435-441, 2005.
Zhang, et al., "Benzoylbenzimidazole-based selective inhibitors targeting Cryptosporidium parvum and Toxoplasma gondii calcium-dependent protein kinase-1," Bioorg Med Chem Lett, vol. 22, No. 16, pp. 5264-5267, 2012.
Bobko, Mark A. et al. "Novel Synthesis of 5-Amino-3-bromo-1-(tert-butyl)-1 H-pyrazole-4-carbonitrile: A Versatile Intermediate for the Preparation of 5-Amino-3-aryl-1-(tert-butyl)-1 Hpyrazole-4-carboxamides" Organic Letters (2012), vol. 14(15), pp. 3906-3908.
Sobenina, L. N. et al. "Synthesis of 5-Amino-3-(2-pyrrolyl)pyrazoles" Russian Journal of Organic Chemistry (1999), vol. 35(8), pp. 1214-1218.
The International Search Report (ISR) with Written Opinion for PCT/US2014/038813 dated Jul. 22, 2014, pp. 1-12.

\* cited by examiner

| Name | Enzyme inhibition (conc. 50% inhibitory, IC$_{50}$) (µM) | | | | Parasite Proliferation (µM) | |
|---|---|---|---|---|---|---|
| | Tg CDPK1 | Cp CDPK1 | SrcKD | AblKD | T. gondii (EC$_{50}$) | C. parvum (EC$_{50}$) |
| 1294 | 0.003 | 0.001 | >10 | >3 | 0.14 | 0.1 |
| 1517 | 0.001 | 0.002 | >30 | >10 | 0.15 | 0.08 |

Table, continued

| Human cell (toxicity) (µM) | | hERG IC$_{50}$ (µM) | Solubility (µM) | Cmpd Stability T$_{1/2}$ (min) | Mouse PK Analysis Results Oral (10 mg/kg dose) | | |
|---|---|---|---|---|---|---|---|
| HepG2 (EC$_{50}$) | CRL 8155 (EC$_{50}$) | | pH 6.5 | Mouse Liver Microsomes | C$_{max}$ (µM) | T$_{max}$ (min) | AUC (µM-min) |
| >40 | >40 | 0.2 | 82 | >60 | 0.75 | 129 | 430 |
| >40 | >40 | >30 | 26 | >60 | 9.9 | 60 | 2450 |

Table, continued

| Plasma Binding (% bound) | | Oral Bioavailability (Rat) |
|---|---|---|
| Human | Mouse | %F |
| 85% | 80% | 91% |
| 67% | 74% | 100% |

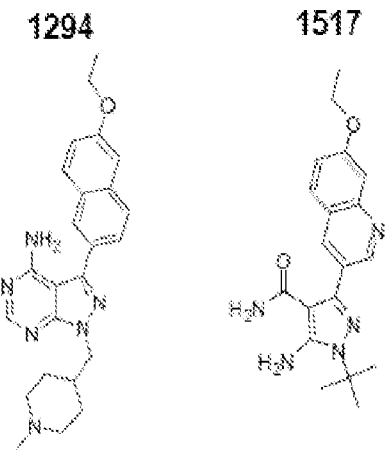

FIGURE 4

5-AMINOPYRAZOLE-4-CARBOXAMIDE INHIBITORS OF CDPK1 FROM T. GONDII AND C. PARVUM

CROSS-REFERENCE TO RELATED APPLICATIONS

This application is a U.S. National Phase of International Application No. PCT/US2014/038813, filed May 20, 2014, which claims priority to U.S. Provisional Patent Application No. 61/825,364, filed May 20, 2013 and U.S. Provisional Patent No. 61/889,451, filed Oct. 10, 2013, the disclosures of which are hereby incorporated by reference in their entireties.

STATEMENT OF GOVERNMENT SUPPORT

This invention was made with government support under Grant No. R01AI089441, awarded by the National Institutes of Health (NIH). The government has certain rights in the invention.

BACKGROUND OF THE INVENTION

1. Field of the Invention

The present disclosure is generally directed to compositions and methods for treating apicomplexan protozoan related disease, such as toxoplasmosis and cryptosporidiosis.

2. Description of Related Art

Toxoplasma gondii (T. gondii) and Cryptosporidium parvum (C. parvum) are apicomplexan parasites that cause serious diseases in humans (toxoplasmosis and cryptosporidiosis) with inadequate treatment options. C. parvum infection has been implicated in 15-20% of childhood diarrhea cases in developing countries and can lead to life-threatening illness in immunocompromised persons. The only approved medicine for C. parvum infection, nitazoxanide, is expensive and not very effective for treating immunocompromised patients. Toxoplasmosis also leads to life-threatening situations in immunocompromised patients. T. gondii infection of pregnant women can result in severe birth defects or miscarriage.

The calcium-dependent protein kinase-1 orthologs of both T. gondii (TgCDPK1) and C. parvum (CpCDPK1) have attracted interest as potential drug targets for these parasites. CDPK1 belongs to a family of serine/threonine protein kinases found in plants and Apicomplexa but not in humans or other animals. Recent genetic and chemical evidence suggests that TgCDPK1 plays critical role in the lifecycle of T. gondii parasites by controlling the exocytosis of micronemes, which are specialized organelles that contain a number of proteins involved in parasite invasion and egress. CpCDPK1 is likely of importance to the lifecycle of C. parvum for similar reasons.

SUMMARY OF THE INVENTION

Current options for treatment of C. parvum and T. gondii infections are limited to sulfadiazine and pyrimethamine, which can have toxic side effects and require lifelong treatment for immunocompromised persons. The present disclosure provides new and effective compounds for treating apicomplexan-related disorders, including those caused by the infectious eukaryotic parasite T. gondii, C. parvum and Cryptosporidium hominus (C. hominus), with no toxic side effects, such as cardiotoxicity. In addition, the compounds of the disclosure provide good oral bioavailability and compound stability in vivo.

Thus, one aspect of the disclosure provides compounds of formula (I):

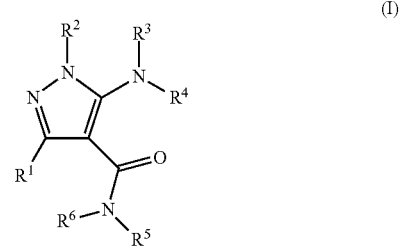

or a pharmaceutically acceptable salt thereof, wherein $R^1$ is one of the formulas:

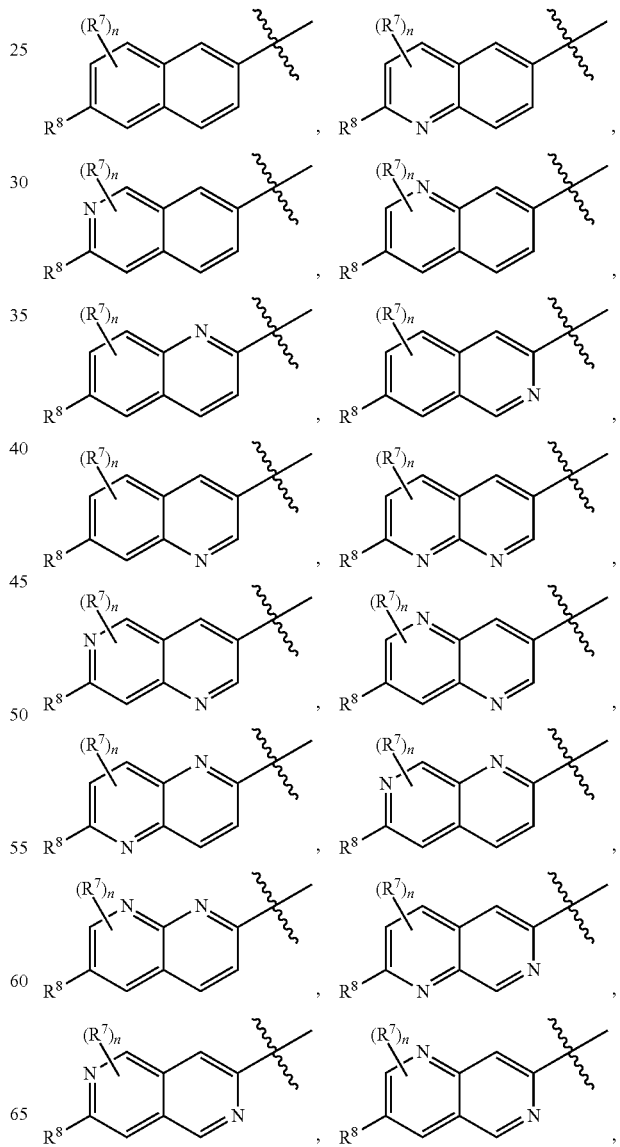

-continued

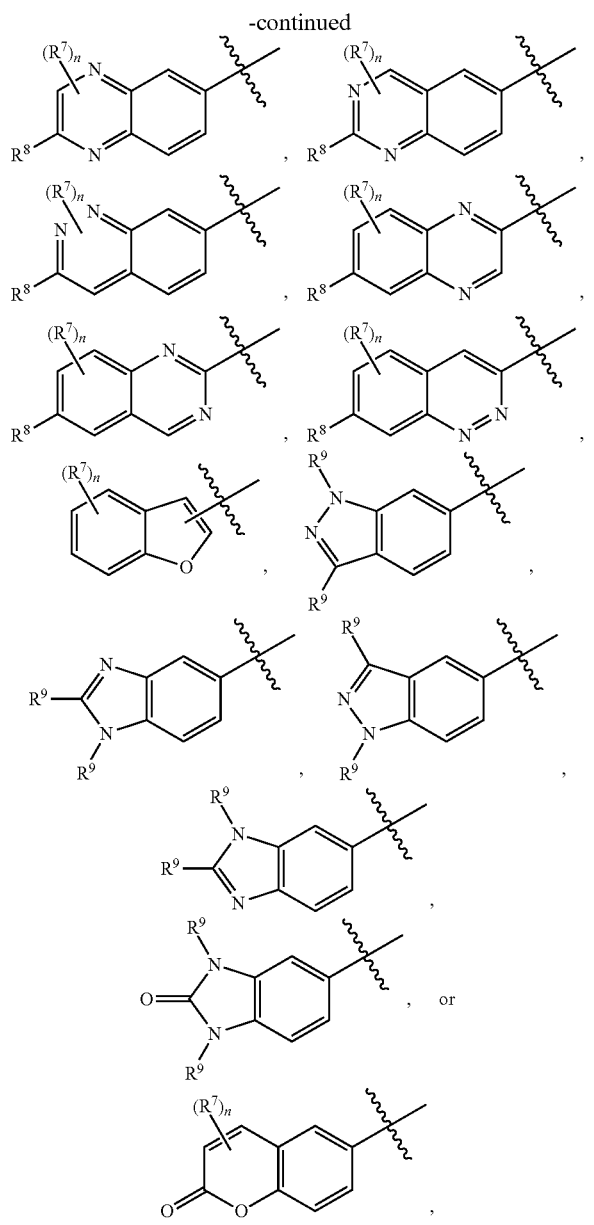

wherein
n is 0, 1, or 2;
each $R^7$ (at any available position on the ring) is independently halogen, cyano, nitro, $C_{1-6}$ alkyl, $C_{1-6}$ haloalkyl, —$OR^{10}$, —$SR^{10}$, —$N(R^{10})_2$, —$C(O)R^{10}$, —$C(O)OR^{10}$, —$C(O)N(R^{10})_2$, —$S(O)_2R^{10}$, —$OC(O)R^{10}$, —$OC(O)OR^{10}$, —$OC(O)N(R^{10})_2$, —$N(R^{10})C(O)R^{10}$, —$N(R^{10})C(O)OR^{10}$, or —$N(R^{10})C(O)N(R^{10})_2$, wherein each $R^{10}$ is independently hydrogen or $C_{1-6}$ alkyl;
$R^8$ is hydrogen, halogen, cyano, nitro, $C_{1-6}$ alkyl, $C_{1-6}$ haloalkyl, or -Q-$R^{8'}$;
Q is —O—, —S—, —NH—, or —N($C_{1-6}$ alkyl)-;
$R^{8'}$ is hydrogen, $C_{1-6}$ alkyl, $C_{2-6}$ alkenyl, $C_{1-6}$ haloalkyl, $C_{3-8}$ cycloalkyl, heterocyclyl, aryl, aryl$C_{1-6}$ alkyl, heteroaryl, or heteroaryl$C_{1-6}$ alkyl, wherein the alkyl, aryl, arylalkyl, heteroaryl, and heteroarylalkyl are optionally substituted with one, two, three, or four groups that are each independently halogen, cyano, nitro, $C_{1-6}$ alkyl, $C_{1-6}$ haloalkyl, —$OR^{14}$, —$SR^{14}$, —$N(R^{14})_2$, —$C(O)R^{14}$, —$C(O)OR^{14}$, —$C(O)N(R^{14})_2$, —$S(O)_2R^{14}$, —$OC(O)R^{14}$, —$OC(O)OR^{14}$, —$OC(O)N(R^{14})_2$, —$N(R^{14})C(O)R^{14}$, —$N(R^{14})C(O)OR^{14}$, or —$N(R^{14})C(O)N(R^{14})_2$, wherein each $R^{14}$ is independently hydrogen or $C_{1-6}$ alkyl; and
each $R^9$ is independently hydrogen or $C_{1-6}$ alkyl;
$R^2$ is hydrogen, $C_{1-6}$ alkyl, $C_{1-6}$ haloalkyl, —$C_{1-4}$ alkyl-$R^{12}$, $C_{2-6}$ alkenyl, $C_{2-6}$ alkynyl, $C_{3-8}$ cycloalkyl, monocyclic heterocyclyl, monocyclic heteroaryl, or phenyl, wherein the alkyl, cycloalkyl, heterocyclyl, heteroaryl, and phenyl groups are each optionally substituted with one or two $R^{13}$ groups;
each $R^{13}$ is independently $C_{1-6}$ alkyl, $C_{1-6}$ haloalkyl, —OR, —SR, —$NR_2$, —C(O)R, —C(O)OR, —C(O)$NR_2$, —$S(O)_2NR_2$, or —$S(O)_2R$; and
where $R^{12}$ is —OR, —SR, —$NR_2$, —C(O)R, —C(O)OR, —C(O)$NR_2$, —$S(O)_2R$, —OC(O)R, —OC(O)OR, —OC(O)$NR_2$, —N(R)C(O)R, —N(R)C(O)OR, —N(R)C(O)$NR_2$, phenyl, monocyclic heteroaryl, $C_{3-8}$ cycloalkyl, or monocyclic heterocyclyl, wherein the aryl, heteroaryl, $C_{3-8}$ cycloalkyl, and heterocyclyl groups are each optionally substituted by one, two, or three groups that are each independently halogen, cyano, nitro, $C_{1-6}$ alkyl, $C_{1-6}$ haloalkyl, —OR, —SR, —$NR_2$, —C(O)R, —C(O)OR, —C(O)$NR_2$, —$S(O)_2R$, —OC(O)R, —OC(O)OR, —OC(O)$NR_2$, —N(R)C(O)R, —N(R)C(O)OR, or —N(R)C(O)$NR_2$;
and each R is independently hydrogen, $C_{1-6}$ alkyl, $C_{2-6}$ alkenyl, $C_{1-6}$ haloalkyl, $C_{3-8}$ cycloalkyl, heterocyclyl, aryl, aryl$C_{1-6}$ alkyl, heteroaryl, or heteroaryl$C_{1-6}$ alkyl, wherein the alkyl, aryl, arylalkyl, heteroaryl, and heteroarylalkyl are optionally substituted with one, two, three, or four groups that are each independently halogen, cyano, nitro, $C_{1-6}$ alkyl, $C_{1-6}$ haloalkyl, —$OR^0$, —$SR^0$, —$N(R^0)_2$, —$C(O)R^0$, —$C(O)OR^0$, —$C(O)N(R^0)_2$, —$S(O)_2R^0$, —$OC(O)R^0$, —$OC(O)OR^0$, —$OC(O)N(R^0)_2$, —$N(R^0)C(O)R^0$, —$N(R^0)C(O)OR^0$, or —$N(R^0)C(O)N(R^0)_2$, wherein each $R^0$ is independently hydrogen or $C_{1-6}$ alkyl;
or $R^2$ and $R^3$ together with the atoms to which they are attached form a heterocyclyl optionally substituted with one or more $R^{13}$ groups;
$R^3$ and $R^4$ are independently selected from hydrogen and $C_{1-6}$ alkyl; and
$R^5$ and $R^6$ are independently selected from hydrogen and $C_{1-6}$ alkyl.
In another aspect, the disclosure provides pharmaceutical compositions comprising one or more of compounds of the disclosure and a pharmaceutically acceptable carrier, diluent, or excipient.
In another aspect, the disclosure provides methods for treating an apicomplexan protozoan related disease comprising providing to a patient in need of such treatment a therapeutically effective amount of either (i) one or more of compounds of the disclosure or (ii) a pharmaceutical composition comprising one or more of compounds of the disclosure and a pharmaceutically acceptable excipient, carrier, or diluent. In other aspect, the apicomplexan protozoan related disease is toxoplasmosis, cryptosporidiosis, malaria neosporosis, eimeriosis, or coccidiosis.
In another aspect, the compounds of the disclosure inhibit apicomplexan calcium dependent protein kinases, including but not limited to T. gondii calcium dependent protein kinases (TgCDPKs) or C. parvum and C. hominus calcium dependent protein kinases (CpCDPKs).

BRIEF DESCRIPTION OF THE DRAWINGS

FIG. 4 shows the table comparing the biological data of compound 39 (1517) and compound 9 (1294).

DETAILED DESCRIPTION OF THE INVENTION

Figure 1:
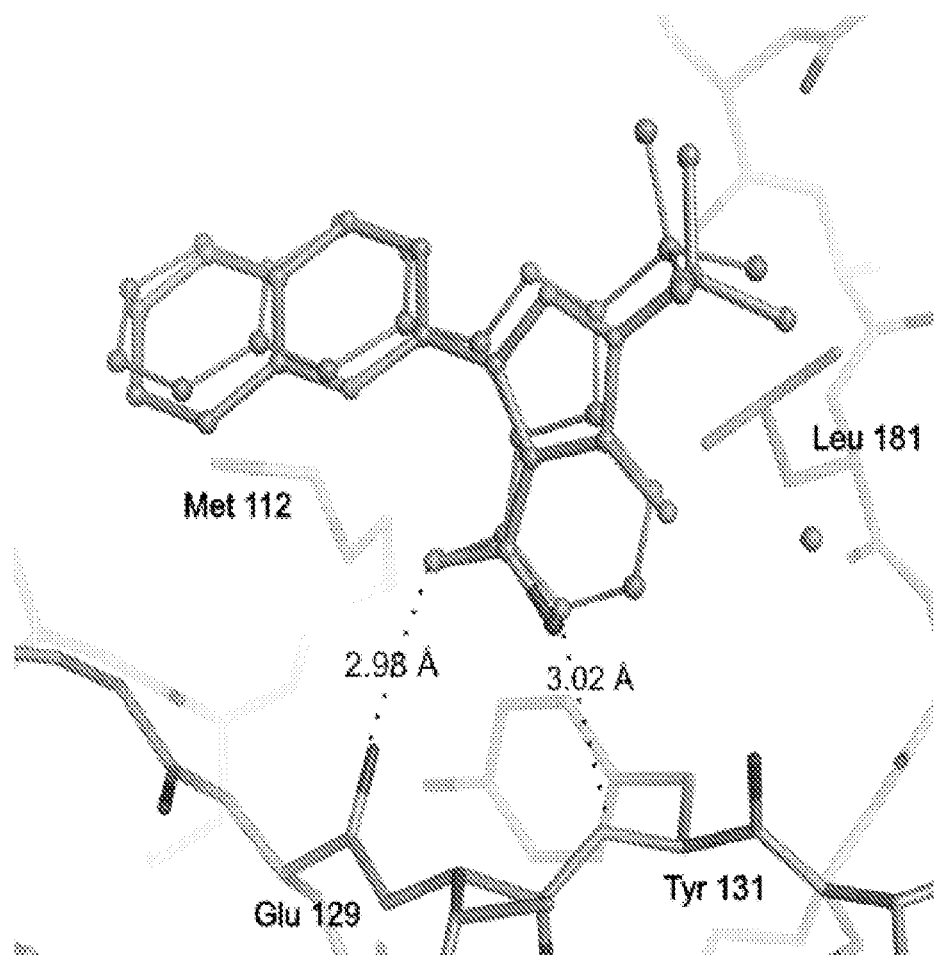
FIG. 1 illustrates a close-up view of inhibitors in an overlay of TgCDPK1-bound 35 (2.0 Å, PDB 4M84; green structure, nitrogen in cyan, oxygen in red, and sulfur in yellow) and 2 (PDB 3I7C carbon in orange and water in pink). The key hydrogen bonds to the backbone oxygen of Glu129 and NH of Tyr131 are the same in both scaffolds.

The following description provides specific details for a thorough understanding of, and enabling description for, embodiments of the disclosure. However, one skilled in the art will understand that the disclosure may be practiced without these details. In other instances, well-known structures and functions have not been shown or described in detail to avoid unnecessarily obscuring the description of the embodiments of the disclosure.

In view of the present disclosure, the compounds described herein can be configured by the person of ordinary skill in the art to meet the desired need. In general, the disclosed compounds provide improvements in treatment of apicomplexan protozoan related diseases. For example, in certain aspects, the compounds of the disclosure are effective against disorders, including those caused by the infectious eukaryotic parasite *T. gondii, C. parvum* and *C. hominus*, with low or no toxic side effects. In particular aspects, the compounds of the disclosure have little or no recombinant hERG (human Ether-à-go-go-Related Gene) binding, which when hERG is inhibited is beneficial against long Q-T syndrome (i.e., cardiotoxicity). In certain other aspects, the compounds of the disclosure provide good oral bioavailability and stability in vivo.

In one embodiment, the compounds of formula (I) are those where $R^3$ and $R^4$ are independently selected from hydrogen and $C_{1-3}$ alkyl. In other embodiments, $R^3$ and $R^4$ are independently selected from hydrogen and methyl. In some other embodiments, one of $R^3$ and $R^4$ is hydrogen and the other is $C_{1-3}$ alkyl. In some other embodiments, one of $R^3$ and $R^4$ is hydrogen and the other is methyl. In certain embodiments, $R^3$ and $R^4$ are both hydrogen.

In one embodiment, the compounds of formula (I) and any preceding embodiment are those where $R^5$ and $R^6$ are independently selected from hydrogen and $C_{1-3}$ alkyl. In other embodiments, $R^5$ and $R^6$ are independently selected from hydrogen and methyl. In some other embodiments, one of $R^5$ and $R^6$ is hydrogen and the other is $C_{1-3}$ alkyl. In some other embodiments, one of $R^5$ and $R^6$ is hydrogen and the other is methyl. In certain embodiments, $R^5$ and $R^6$ are both hydrogen.

Compounds of formula (I), in one embodiment, include those where $R^3$, $R^4$, $R^5$ and $R^6$ are all hydrogen.

Compounds of formula (I) and any previous embodiment include compounds wherein $R^2$ is $C_{1-6}$ alkyl, $C_{1-6}$ haloalkyl, —$C_{1-4}$ alkyl-$R^{12}$, $C_{2-6}$ alkenyl, $C_{2-6}$ alkynyl, $C_{3-8}$ cycloalkyl, monocyclic heterocyclyl, monocyclic heteroaryl, or phenyl, wherein the alkyl, cycloalkyl, heterocyclyl, heteroaryl, and phenyl groups are each optionally substituted with one or two $R^{13}$ groups. In one embodiment, $R^2$ is $C_{1-6}$ alkyl, $C_{1-6}$ haloalkyl, or —$C_{1-4}$ alkyl-$R^{12}$, wherein the alkyl group is optionally substituted with one or two $R^{13}$ groups. In another embodiment, $R^2$ is $C_{1-6}$ alkyl or $C_{1-6}$ haloalkyl, wherein the alkyl group is optionally substituted with one or two $R^{13}$ groups. In another embodiment, $R^2$ is $C_{1-6}$ alkyl or —$C_{1-4}$ alkyl-$R^{12}$, wherein the alkyl group is optionally substituted with one or two $R^{13}$ groups.

Certain embodiments of the compounds of the disclosure include those where $R^2$ is $C_{1-6}$ alkyl optionally substituted with one or two $R^{13}$ groups. In some embodiments, $R^2$ is $C_{1-6}$ alkyl optionally substituted with —OR or —$NR_2$. In other embodiments, $R^2$ is $C_{1-6}$ alkyl optionally substituted with —OH. In one embodiment of the disclosure, the compounds are those where $R^2$ is unsubstituted $C_{1-6}$ alkyl. For example, $R^2$ may be methyl, ethyl, propyl, isopropyl, butyl, secbutyl, isobutyl, and tertbutyl. In one embodiment, $R^2$ may be methyl, ethyl, propyl, isopropyl, butyl, secbutyl, isobutyl, or tertbutyl, each optionally substituted with one or two $R^{13}$ groups. In a particular embodiment, $R^2$ is tert-butyl. In some other embodiments, $R^2$ is $C_{1-6}$ haloalkyl.

Other particularly useful compounds of formula (I) and any preceding embodiment are those where $R^2$ is —$C_{1-4}$ alkyl-$R^{12}$ optionally substituted with one or two $R^{13}$ groups. In one embodiment, $R^{12}$ is —OR, —$NR_2$, —C(O)R, —C(O)OR, —C(O)$NR_2$, —S(O)$_2$R, phenyl, monocyclic heteroaryl, $C_{3-8}$ cycloalkyl, or monocyclic heterocyclyl, wherein the aryl, heteroaryl, $C_{3-8}$ cycloalkyl, and heterocyclyl groups are each optionally substituted by one, two, or three groups that are each independently halogen, cyano, nitro, $C_{1-6}$ alkyl, $C_{1-6}$ haloalkyl, —OR, —SR, —$NR_2$, —C(O)R, —C(O)OR, —C(O)$NR_2$, —S(O)$_2$R, —OC(O)R, —OC(O)OR, —OC(O)$NR_2$, —N(R)C(O)R, —N(R)C(O)OR, or —N(R)C(O)$NR_2$. In certain embodiments, $R^{12}$ is —OR, —$NR_2$, phenyl, monocyclic heteroaryl, $C_{3-8}$ cycloalkyl, or monocyclic heterocyclyl, wherein the aryl, heteroaryl, $C_{3-8}$ cycloalkyl, and heterocyclyl groups are each optionally substituted by one, two, or three groups that are each independently halogen, cyano, nitro, $C_{1-6}$ alkyl, $C_{1-6}$ haloalkyl, —OR, —SR, —$NR_2$, —C(O)R, —C(O)OR, —C(O)$NR_2$, —S(O)$_2$R, —OC(O)R, —OC(O)OR, —OC(O)$NR_2$, —N(R)C(O)R, —N(R)C(O)OR, or —N(R)C(O)$NR_2$.

In another embodiment, $R^{12}$ is —OR, —SR, —$NR_2$, —C(O)R, —C(O)OR, —C(O)$NR_2$, $C_{3-8}$ cycloalkyl, or monocyclic heterocyclyl, wherein the $C_{3-8}$ cycloalkyl, and heterocyclyl groups are each optionally substituted by one, two, or three groups that are each independently halogen, cyano, nitro, $C_{1-6}$ alkyl, $C_{1-6}$ haloalkyl, —OR, —SR, —$NR_2$, —C(O)R, —C(O)OR, —C(O)$NR_2$, —S(O)$_2$R, —OC(O)R, —OC(O)OR, —OC(O)$NR_2$, —N(R)C(O)R, —N(R)C(O)OR, or —N(R)C(O)$NR_2$. In another embodiment, $R^{12}$ is —OR or —$NR_2$. Some embodiments include compounds of $R^2$ where $R^{12}$ is —OR. Some other embodiments include compounds of $R^2$ where $R^{12}$ is $C_{3-8}$ cycloalkyl or monocyclic heterocyclyl, both substituted as noted above.

In another embodiment, compounds of formula (I) and the above embodiments are those where $R^2$ is $C_{3-8}$ cycloalkyl or monocyclic heterocyclyl, each optionally substituted with one or two $R^{13}$ groups. In some embodiments, $R^2$ is $C_{3-8}$ cycloalkyl optionally substituted with one or two $R^{13}$ groups. In other embodiments, $R^2$ is monocyclic heterocyclyl optionally substituted with one or two $R^{13}$ groups.

In another embodiment, compounds of formula (I) and the above embodiments are those where $R^2$ is hydrogen.

Other particularly useful compounds of formula (I) and any preceding embodiment are those wherein $R^1$ is one of the formulas:

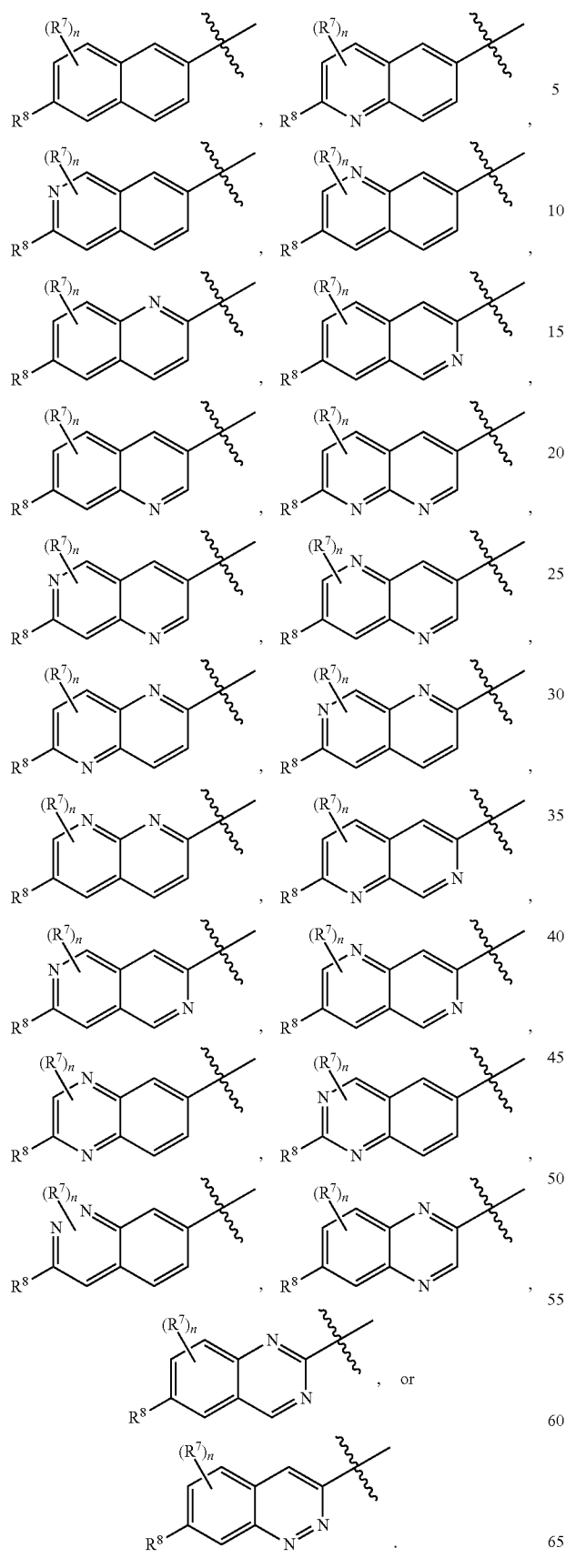
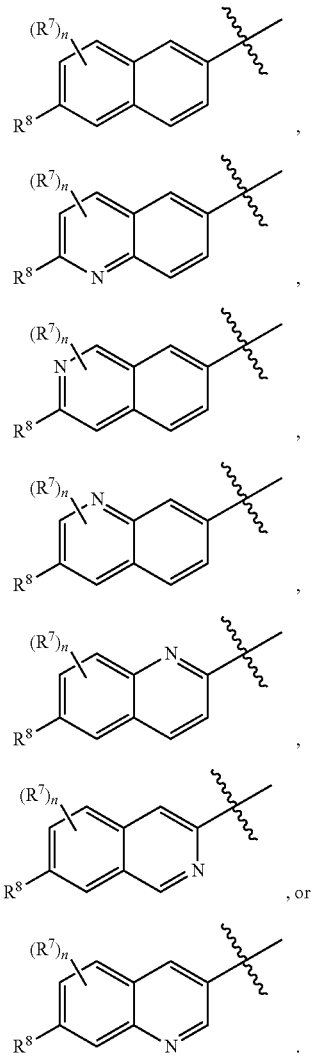
As understood by one of skill in the art, each $R^7$ may be in any available position on the bicyclic ring. In some embodiments, $R^1$ is of the formula:
In another embodiment, $R^1$ is of the formula:
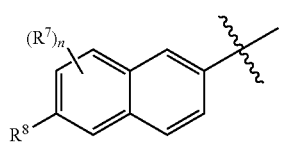
In some embodiments, $R^1$ is one of formulas:
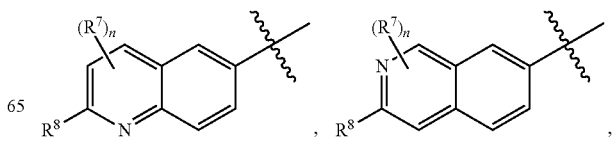

-continued
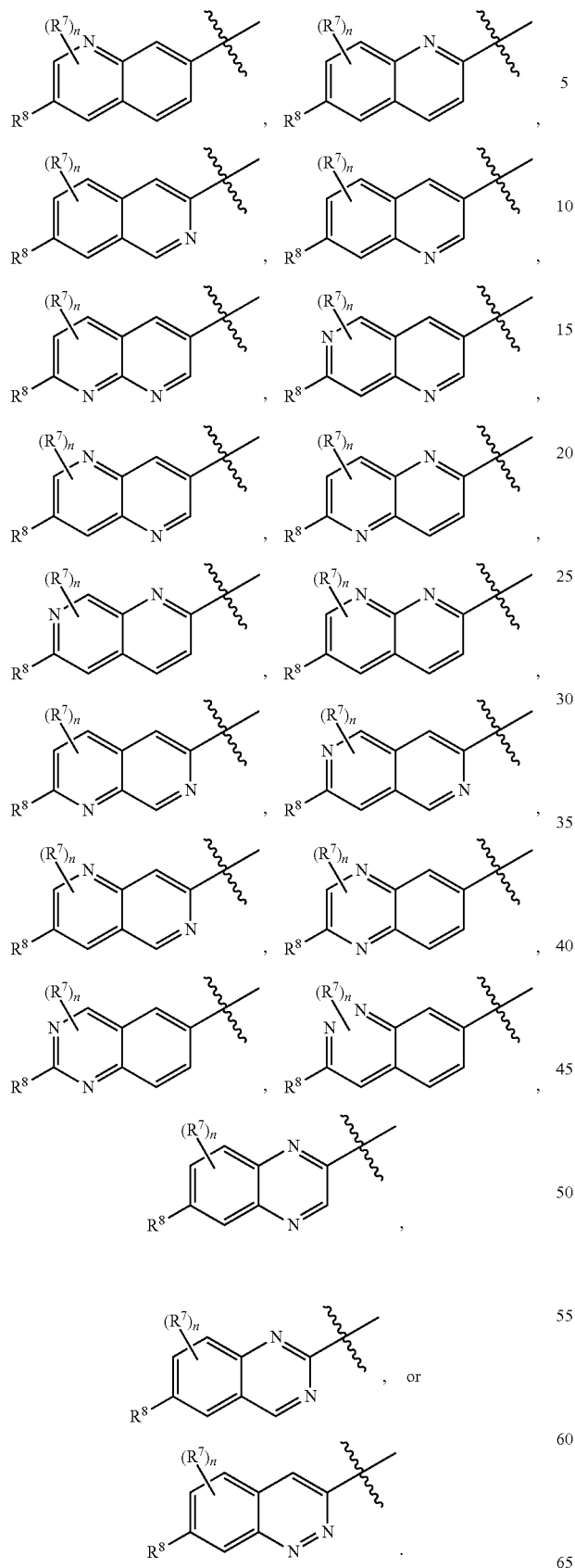
In some other embodiments, R¹ is one of formulas:
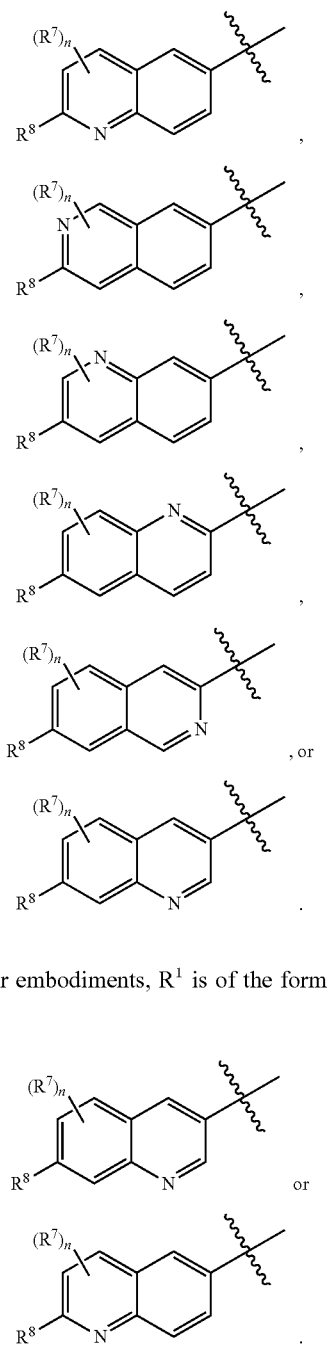
In some other embodiments, R¹ is of the formula:
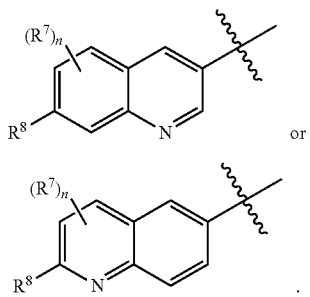
In another embodiment, R¹ is of the formula:
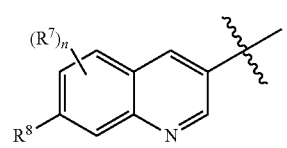

In yet another embodiment, R¹ is of the formula:
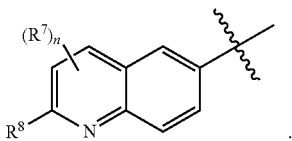
In some other embodiments, R¹ is of the formula:
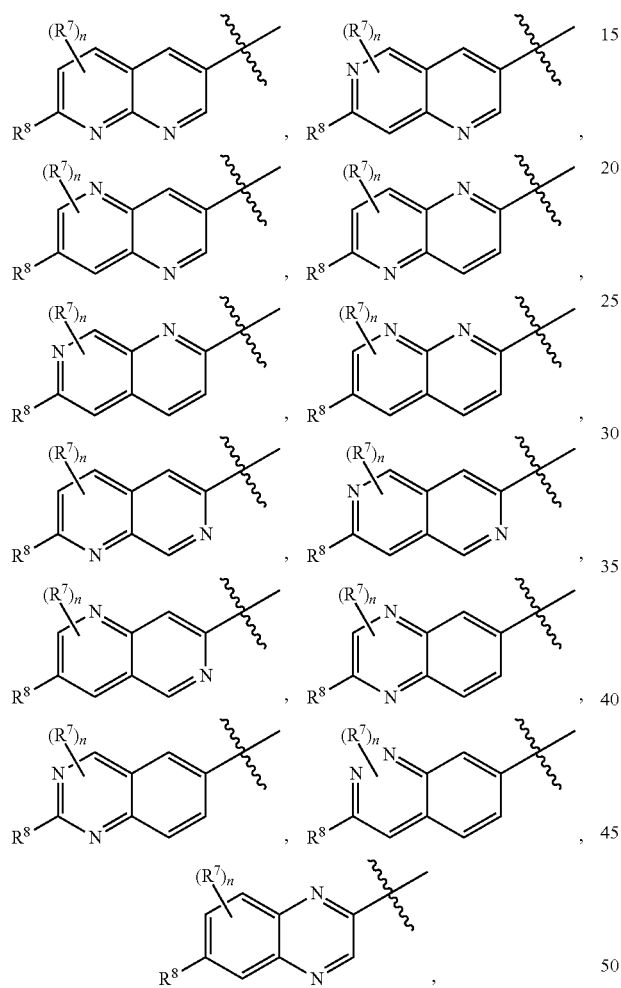
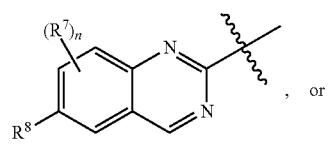, or
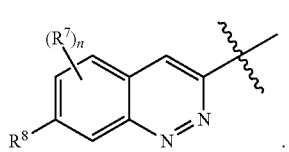.
In some other embodiments, R¹ is of the formula:
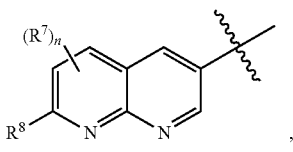,
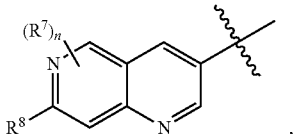,
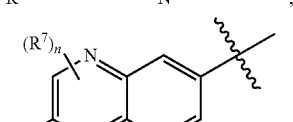,
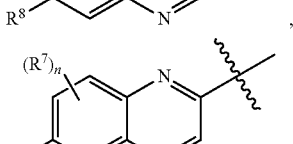,
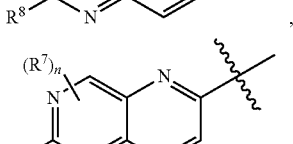,
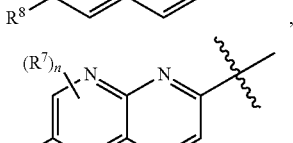,
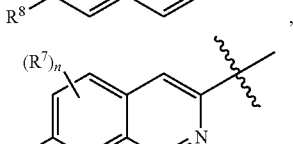,
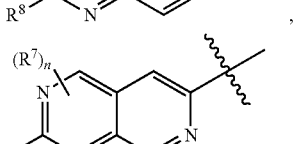,
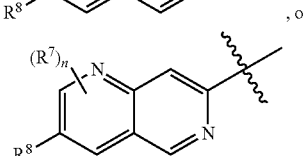, or
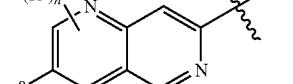.
In some other embodiments, R¹ is of the formula:
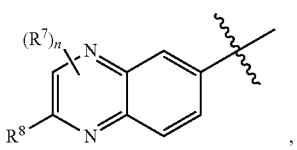,
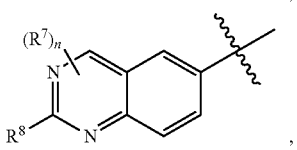,

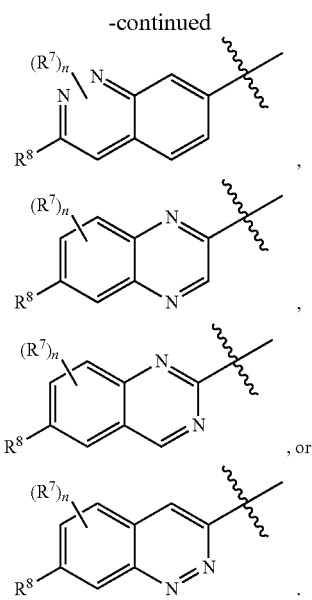

As noted above, $R^8$ may be hydrogen, halogen, cyano, nitro, $C_{1-6}$ alkyl, $C_{1-6}$ haloalkyl, or -Q-$R^{8'}$. Thus, in one embodiment, compounds of formula (I) and any of the above embodiments include those where $R^8$ is hydrogen, halogen, cyano, nitro, $C_{1-6}$ alkyl, $C_{1-6}$ haloalkyl. In one embodiment, $R^8$ is hydrogen, halogen, cyano, or nitro. In another embodiment, $R^8$ is hydrogen, halogen, $C_{1-6}$ alkyl, or $C_{1-6}$ haloalkyl. In yet another embodiment, $R^8$ is hydrogen or halogen. In particular embodiments, $R^8$ is hydrogen.

Another embodiment provides compounds of formula (I) and any of the above embodiments include those where $R^8$ is -Q-$R^{8'}$.

Embodiments of the compounds of the disclosure include those where, when $R^8$ is -Q-$R^{8'}$, then:

Q is —O—, —S—, —NH—, or —N($C_{1-6}$ alkyl)-;

$R^{8'}$ is hydrogen, $C_{1-6}$ alkyl, $C_{2-6}$ alkenyl, $C_{1-6}$ haloalkyl, $C_{3-8}$ cycloalkyl, heterocyclyl, aryl, aryl$C_{1-6}$ alkyl, heteroaryl, or heteroaryl$C_{1-6}$ alkyl, wherein the alkyl, aryl, arylalkyl, heteroaryl, and heteroarylalkyl are optionally substituted with one, two, three, or four groups that are each independently halogen, cyano, nitro, $C_{1-6}$ alkyl, $C_{1-6}$ haloalkyl, —OR$^{14}$, —SR$^{14}$, —N(R$^{14}$)$_2$, —C(O)R$^{14}$, —C(O)OR$^{14}$, —C(O)N(R$^{14}$)$_2$, —S(O)$_2$R$^{14}$, —OC(O)R$^{14}$, —OC(O)OR$^{14}$, —OC(O)N(R$^{14}$)$_2$, —N(R$^{14}$)C(O)R$^{14}$, —N(R$^{14}$)C(O)OR$^{14}$, or —N(R$^{14}$)C(O)N(R$^{14}$)$_2$, wherein each R$^{14}$ is independently hydrogen or $C_{1-6}$ alkyl.

In other embodiments, Q is —O—, —S—, —NH—, or —N($C_{1-6}$ alkyl)-; and $R^{8'}$ is $C_{1-6}$ alkyl, $C_{2-6}$ alkenyl, $C_{1-6}$ haloalkyl, $C_{3-8}$ cycloalkyl, heterocyclyl, aryl, aryl$C_{1-6}$ alkyl, heteroaryl, or heteroaryl$C_{1-6}$ alkyl, wherein the alkyl, aryl, arylalkyl, heteroaryl, and heteroarylalkyl are optionally substituted with one, two, three, or four groups that are each independently halogen, cyano, nitro, $C_{1-6}$ alkyl, $C_{1-6}$ haloalkyl, —OR$^{14}$, —SR$^{14}$, —N(R$^{14}$)$_2$, —C(O)R$^{14}$, —C(O)OR$^{14}$, —C(O)N(R$^{14}$)$_2$, —S(O)$_2$R$^{14}$, —OC(O)R$^{14}$, —OC(O)OR$^{14}$, —OC(O)N(R$^{14}$)$_2$, —N(R$^{14}$)C(O)R$^{14}$, —N(R$^{14}$)C(O)OR$^{14}$, or —N(R$^{14}$)C(O)N(R$^{14}$)$_2$, wherein each R$^{14}$ is independently hydrogen or $C_{1-6}$ alkyl.

Embodiments of the compounds of the disclosure include those where $R^8$ is —O—$R^{8'}$, —NHR$^{8'}$, or —N($C_{1-6}$ alkyl)R$^{8'}$. In some other embodiments, $R^8$ is —O—R$^{8'}$.

Other embodiments provide compounds where, according to any preceding embodiment, $R^{8'}$ is hydrogen, $C_{1-6}$ alkyl, $C_{2-6}$ alkenyl, $C_{1-6}$ haloalkyl, or $C_{3-8}$ cycloalkyl, wherein the alkyl moieties are optionally substituted with one, two, three, or four groups that are each independently halogen, cyano, nitro, $C_{1-6}$ alkyl, $C_{1-6}$ haloalkyl, —OR$^{14}$, —SR$^{14}$, —N(R$^{14}$)$_2$, —C(O)R$^{14}$, —C(O)OR$^{14}$, —C(O)N(R$^{14}$)$_2$, —S(O)$_2$R$^{14}$, —OC(O)R$^{14}$, —OC(O)OR$^{14}$, —OC(O)N(R$^{14}$)$_2$, —N(R$^{14}$)C(O)R$^{14}$, —N(R$^{14}$)C(O)OR$^{14}$, or —N(R$^{14}$)C(O)N(R$^{14}$)$_2$, wherein each R$^{14}$ is independently hydrogen or $C_{1-6}$ alkyl. In some other embodiments, $R^{8'}$ is $C_{1-6}$ alkyl, $C_{1-6}$ haloalkyl, or $C_{3-8}$ cycloalkyl, wherein the alkyl moieties are optionally substituted with one, two, three, or four groups that are each independently halogen, cyano, nitro, $C_{1-6}$ alkyl, $C_{1-6}$ haloalkyl, —OR$^{14}$, —SR$^{14}$, —N(R$^{14}$)$_2$, —C(O)R$^{14}$, —C(O)OR$^{14}$, —C(O)N(R$^{14}$)$_2$, —S(O)$_2$R$^{14}$, —OC(O)R$^{14}$, —OC(O)OR$^{14}$, —OC(O)N(R$^{14}$)$_2$, —N(R$^{14}$)C(O)R$^{14}$, —N(R$^{14}$)C(O)OR$^{14}$, or —N(R$^{14}$)C(O)N(R$^{14}$)$_2$, wherein each R$^{14}$ is independently hydrogen or $C_{1-6}$ alkyl. In additional embodiments, $R^{8'}$ is $C_{1-6}$ alkyl optionally substituted with one, two, three, or four groups that are each independently halogen, cyano, nitro, $C_{1-6}$ alkyl, $C_{1-6}$ haloalkyl, —OR$^{14}$, —SR$^{14}$, —N(R$^{14}$)$_2$, —C(O)R$^{14}$, —C(O)OR$^{14}$, —C(O)N(R$^{14}$)$_2$, —S(O)$_2$R$^{14}$, —OC(O)R$^{14}$, —OC(O)OR$^{14}$, —OC(O)N(R$^{14}$)$_2$, —N(R$^{14}$)C(O)R$^{14}$, —N(R$^{14}$)C(O)OR$^{14}$, or —N(R$^{14}$)C(O)N(R$^{14}$)$_2$, wherein each R$^{14}$ is independently hydrogen or $C_{1-6}$ alkyl.

Another embodiment provides compounds of any of the above embodiments include those where $R^{8'}$ is $C_{1-6}$ alkyl optionally substituted with one, two, three, or four groups that are each independently halogen, —OR$^{14}$, —SR$^{14}$, —N(R$^{14}$)$_2$, —C(O)R$^{14}$, —C(O)OR$^{14}$, —C(O)N(R$^{14}$)$_2$, or —S(O)$_2$R$^{14}$, wherein each R$^{14}$ is independently hydrogen or $C_{1-6}$ alkyl. Embodiments of the disclosed compounds include those where $R^{8'}$ is unsubstituted $C_{1-6}$ alkyl.

Embodiments of the compounds of the disclosure include those where $R^{8'}$ is methyl, ethyl, propyl, i-propyl, butyl, i-butyl, sec-butyl, or t-butyl. In some embodiments, $R^{8'}$ is ethyl.

In one embodiment, $R^8$ is —O—$R^{8'}$, wherein $R^{8'}$ is $C_{1-6}$ alkyl, $C_{1-6}$ haloalkyl, $C_{3-8}$ cycloalkyl, aryl$C_{1-6}$ alkyl, or heteroaryl$C_{1-6}$ alkyl, each optionally substituted as noted above.

Other embodiments provide compounds where $R^8$ is —O—$R^{8'}$, and $R^{8'}$ is $C_{1-6}$ alkyl or $C_{1-6}$ haloalkyl, each optionally substituted as noted above. In one embodiment, $R^8$ is $C_{1-6}$ alkoxy optionally substituted as noted above. For example, $R^8$ may be methoxy, ethoxy, n- or i-propoxy, or n-, i-, or t-butoxy (each optionally substituted as noted above). In one embodiment, $R^8$ is ethoxy.

Another embodiment provides compounds of formula (I) and any of the above embodiments where $R^8$ is hydrogen, halogen, $C_{1-6}$ alkyl, or $C_{1-6}$ haloalkyl. In one embodiment, $R^8$ is $C_{1-6}$ alkyl or $C_{1-6}$ haloalkyl. In another embodiment, $R^8$ is hydrogen or halogen. In yet another embodiment, $R^8$ is halogen, $C_{1-6}$ alkyl, or $C_{1-6}$ haloalkyl.

Other particularly useful compounds of formula (I) and any preceding embodiment are those wherein $R^1$ is one of the formulas:

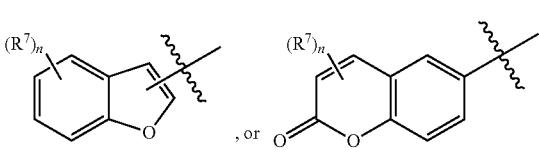

In another embodiment, $R^1$ is of the formula:

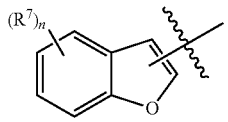

In another embodiment, $R^1$ is of the formula:

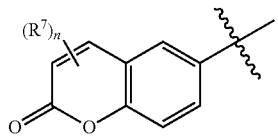

Another embodiment provides compounds of formula (I) and any of the above embodiments where $R^7$, when present, is at any available position on the ring and independently selected from halogen, cyano, nitro, $C_{1-6}$ alkyl, $C_{1-6}$ haloalkyl, $-OR^{10}$, $-SR^{10}$, $-N(R^{10})_2$, $-C(O)R^{10}$, $-C(O)OR^{10}$, $-C(O)N(R^{10})_2$, $-S(O)_2R^{10}$, and $-N(R^{10})C(O)R^{10}$, wherein each $R^{10}$ is independently hydrogen or $C_{1-6}$ alkyl. In another embodiment, $R^7$, when present, is independently selected from halogen, cyano, nitro, $C_{1-6}$ alkyl, $C_{1-6}$ haloalkyl, $-OR^{10}$, $-N(R^{10})_2$, $-C(O)R^{10}$, $-C(O)OR^{10}$, and $-C(O)N(R^{10})_2$. In another embodiment, $R^7$, when present, is independently selected from halogen, cyano, nitro, $C_{1-6}$ alkyl, $C_{1-6}$ haloalkyl, $-OR^{10}$, and $-N(R^{10})_2$. In another embodiment, $R^7$, when present, is independently selected from $C_{1-6}$ alkyl, $C_{1-6}$ haloalkyl, $-OR^{10}$, and $-N(R^{10})_2$. In another embodiment, $R^7$, when present, is independently selected from $C_{1-6}$ alkyl and $C_{1-6}$ haloalkyl.

Other embodiments of the disclosure according to any preceding embodiments provide compounds where each $R^7$ when present is independently halogen, cyano, nitro, $C_{1-6}$ alkyl, $C_{1-6}$ haloalkyl, $-OR^{10}$, $-SR^{10}$, $-N(R^{10})_2$, $-C(O)R^{10}$, $-C(O)OR^{10}$, or $-C(O)N(R^{10})_2$, wherein each $R^{10}$ is independently hydrogen or $C_{1-6}$ alkyl. In one embodiment, each $R^7$ is independently halogen, cyano, nitro, $C_{1-6}$ alkyl, $C_{1-6}$ haloalkyl, $-OR^{10}$, or $-N(R^{10})_2$, wherein each $R^{10}$ is independently hydrogen or $C_{1-6}$ alkyl. In another embodiment, each $R^7$ is independently halogen, cyano, nitro, $C_{1-6}$ alkyl, or $C_{1-6}$ haloalkyl.

Another embodiment provides compounds of formula (I) and any of the above embodiments where n is 0 or 1. In one embodiments, n is 0. In other embodiments, n is 1.

Other particularly useful compounds of formula (I) and any preceding embodiment are those wherein $R^1$ is one of the formulas:

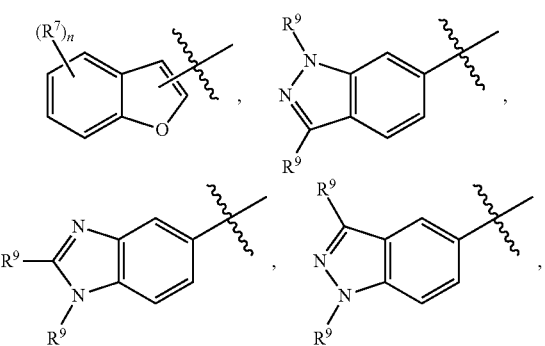

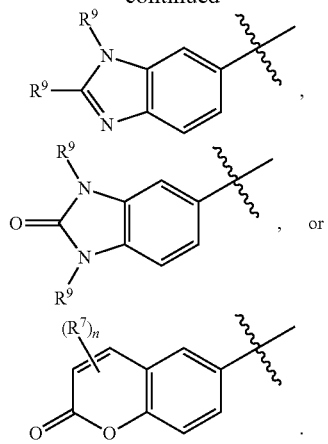

As understood by one of skill in the art, each $R^7$ may be in any available position on the bicyclic ring. In one embodiment, $R^1$ is one of the formulas:

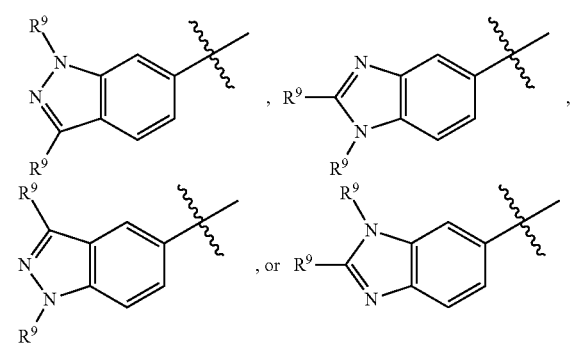

In another embodiment, $R^1$ is one of the formulas:

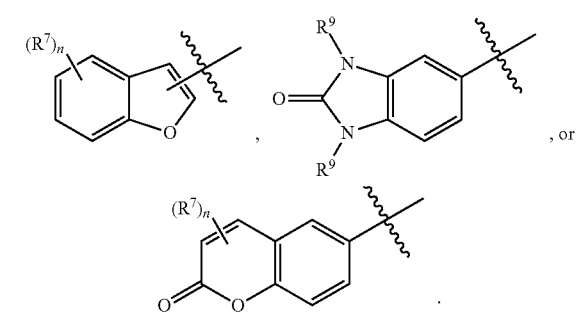

In another embodiment, $R^1$ is of the formula:

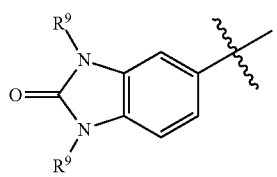

Other embodiments provide compounds where, according to any preceding embodiment, each $R^9$ is independently hydrogen or $C_{1-4}$ alkyl. In some embodiments, each $R^9$ is independently hydrogen or methyl.

Clinical toxoplasmosis is caused by the actively dividing tachyzoite form of the parasite, which exits its host cell and invades a new cell every few days. TgCDPK1 has a unique ATP-binding site with a small gatekeeper residue, as opposed to the large gatekeeper residues present in mammalian protein kinases. This key difference in gatekeeper residues between mammalian kinases and TgCDPK1 allowed use of bumped kinase inhibitors (BKIs) to selectively inhibit TgCDPK1 without untoward effects on the mammalian host cell.

Accordingly, the disclosure provides methods for treating an apicomplexan protozoan related disease comprising providing to a patient in need of such treatment a therapeutically effective amount of either (i) one or more of compounds of the disclosure or (ii) a pharmaceutical composition comprising one or more of compounds of the disclosure and a pharmaceutically acceptable excipient, carrier, or diluent. In one embodiment, the compound of the disclosure is according to of the formula (I) as defined above, or any embodiment thereof.

One embodiment of the present disclosure provide a method of treating a subject in need of treatment for an apicomplexan-related disease comprising administering an effective amount of one or more of compound of the disclosure, that inhibits the activity of an apicomplexan calcium dependent protein kinase (CDPK).

Particular embodiments of the present disclosure provide a method of treating cryptosporidiosis in a subject comprising administering an effective amount of one or more of compounds of the disclosure, that inhibits the activity of *Cryptosporidium parvum* and *C. hominus* calcium dependent protein kinase 1 (CpCDPK1).

Other particular embodiments of the present disclosure provide a method of treating cryptosporidiosis in a subject comprising administering an effective amount of one or more of compounds of the disclosure, that inhibits the activity of *T. gondii*, calcium dependent protein kinase 1 (TgCDPK1).

Optionally, the compound of the disclosure, can be administered in combination with a second agent, such as agents specific for use against the specific apicomplexan-related disorder being treated.

In one embodiment, the apicomplexan protozoan related disease is toxoplasmosis. As understood by one of ordinary skill in the art, toxoplasmosis can encompass a number of pathologies, including, but not limited to, encephalitis, retinitis, lymphadenopathy, disseminated disease, and hepatitis. Toxoplasmosis infects most genera of warm-blooded animals, including humans, but the primary host is the felid (cat) family.

Cats are the definitive host for the *Toxoplasma* organism. Infection with this protozoan parasite is fairly common, but actual disease caused by this parasite is relatively rare in cats. Cats can become infected by *Toxoplasma* by eating any of the three infective stages of the parasites. The most common route of infection is probably by ingestion of tissue cysts in infected prey or in other raw meat. *Toxoplasma* multiply in the small intestines and in approximately two to three weeks the oocysts are excreted in the infected cat's feces. In another example, cats may be treated prophylactically for toxoplasmosis (e.g., a gastrointestinal infection) provided by providing a therapeutically effective amount of one or more of compounds of the disclosure or to eliminate the chance that they would shed infectious Toxoplasmodia oocyts and infect their owners. In another embodiment, infected cats may be treated by providing a therapeutically effective amount of one or more of compounds of the disclosure to treat toxoplasmosis. As will be understood by those of skill in the art, similar prophylactic and therapeutic methods for limiting development of or treating toxoplasmosis can be used in any animal that can be infected by *Toxoplasma* sp.

Animals are infected by eating infected meat, by ingestion of feces of a cat that has itself recently been infected, or by transmission from mother to fetus. While cats are often blamed for spreading toxoplasmosis, contact with raw meat is a more significant source of human infections in many countries, and fecal contamination of hands is a greater risk factor. Infection has two stages (1) acute toxoplasmosis; and (2) latent toxoplasmosis. During acute toxoplasmosis, symptoms are often influenza-like: swollen lymph nodes, or muscle aches and pains that last for a month or more. Rarely, a patient with a fully functioning immune system may develop eye damage from toxoplasmosis. Young children (15 years old or younger) and immunocompromised patients, such as those with HIV/AIDS, those taking certain types of chemotherapy, or those who have recently received an organ transplant, may develop severe toxoplasmosis. In an embodiment, a young child can be 14 years old or younger; or 13 years old or younger; or 12 years old or younger; or 11 years old or younger; or 10 years old or younger; or 9 years old or younger; or 8 years old or younger; or 7 years old or younger; or 6 years old or younger; or 5 years old or younger; or 4 years old or younger; or 3 years old or younger; or 2 years old or younger; or 1 year old or younger. This can cause damage to the brain (encephalitis) or the eyes (necrotizing retinochoroiditis). Infants infected via placental transmission may be born with either of these problems, or with nasal malformations, although these complications are rare in newborns. In most immuno-competent patients, the infection enters a latent phase, during which only bradyzoites are present, forming cysts in nervous and muscle tissue. Most infants who are infected while in the womb have no symptoms at birth but may develop symptoms later in life. The most common current therapy for toxoplasmosis is sulfadiazine/pyrimethamine combination therapy, but therapy is often limited by allergic reactions to the sulfa component, anemia and pancytopenia induced by blocking the folate pathway. When sulfadiazine cannot be used, clindamycin may be combined with pyrimethamine but most experts feel it does not work as well as sulfadiazine. Spiramycin has been used for toxoplasmosis during pregnancy but has issues with low efficacy and is no longer available in the United States. Thus few therapeutic alternatives are available.

In another embodiment, the apicomplexan protozoan related disease is cryptosporidiosis. Cryptosporidiosis is caused by infection with the single-celled parasite (not bacterium) *Cryptosporidium parvum*. This parasite is found in many mammals including lambs, calves, goat kids, piglets and humans. Research so far has shown two basic types, the bovine type which affects most species, and a second human type which causes disease in humans only. Outbreaks of human disease, where large numbers of people are affected, are usually water-borne and usually associated with the bovine type of *cryptosporidium*. Individual sporadic cases of cryptosporidiosis in humans are mostly (around 60%) associated with the human type of *cryptosporidium*.

Cryptosporidiosis affects the intestines of mammals and is typically an acute short-term infection. It is spread through the fecal-oral route, often through contaminated water; the main symptom is self-limiting diarrhea in people with intact immune systems. In immunocompromised individuals, such as HIV/AIDS patients, the symptoms are particularly severe and often fatal. *Cryptosporidium* is the organism most commonly isolated in HIV positive patients presenting with diarrhea. Cryptosporidiosis is one of the most common waterborne diseases and is found worldwide. The parasite is transmitted by environmentally hardy microbial cysts (oocysts) that, once ingested, exist in the small intestine and result in an infection of intestinal epithelial tissue. Infection is through contaminated material such as earth, water, uncooked or cross-contaminated food that has been in contact with the feces of an infected individual or animal. It is especially prevalent amongst those in regular contact with bodies of fresh water including recreational water such as swimming pools. Other potential sources include insufficiently treated or insufficiently filtered water supplies, contaminated food, or exposure to feces. Symptoms appear from two to ten days after infection, and last for up to two weeks or more. In immuno-competent people, the disease can be asymptomatic or cause acute diarrhea or persistent diarrhea that can last for a few weeks. There is often stomach pain or cramping and a low fever. Other symptoms may include nausea, vomiting, malabsorption, and dehydration. Individuals who are asymptomatic (have no symptoms) are nevertheless infective. Immunocompromised people, as well as very young or very old people, can develop a more severe form of cryptosporidiosis. When *Cryptosporidium* spreads beyond the intestine, as it can predominantly in patients with AIDS, it can reach the lungs, middle ear, pancreas, and stomach. Thus, one symptom is pain in the right upper quadrant. The parasite can infect the biliary tract, causing biliary cryptosporidiosis. This can result in cholecystitis and cholangitis. Current treatment is symptomatic, with fluid rehydration, electrolyte correction and management of any pain. Nitazoxanide has been FDA-approved for treatment of diarrhea caused by *Cryptosporidium* in people with healthy immune systems and is available by prescription, however it only shortens the duration of diarrhea by a couple of days. The effectiveness of nitazoxanide in immunosuppressed individuals is unclear and multiple trials have shown no benefit.

The compounds described herein may have use in other apicoplexa protozoan related diseases, such as coccidiosis or eimeriosis caused by *Eimeria* spp., cause infections and disease in poultry; which causes Babesiosis which is caused by *Babesia* spp. and results in a malaria-like disease, and malaria in humans and animals caused by *Plasmodium* spp.

As used herein, the term "subject", "individual," or "patient," used interchangeably, refers to any animal, including mammals, preferably mice, rats, other rodents, rabbits, dogs, cats, birds, swine, horses, livestock (e.g., pigs, sheep, goats, cattle), primates or humans.

As used here, a subject "in need thereof" refers to a subject that has the disorder or disease to be treated or is predisposed to or otherwise at risk of developing the disease or disorder.

As used here, the terms "treatment" and "treating" means:
(i) inhibiting the progression the disease;
(ii) prophylactic use for example, preventing or limiting development of a disease, condition or disorder in an individual who may be predisposed or otherwise at risk to the disease, condition or disorder but does not yet experience or display the pathology or symptomatology of the disease;
(iii) inhibiting the disease; for example, inhibiting a disease, condition or disorder in an individual who is experiencing or displaying the pathology or symptomatology of the disease, condition or disorder;
(iv) ameliorating the referenced disease state, for example, ameliorating a disease, condition or disorder in an individual who is experiencing or displaying the pathology or symptomatology of the disease, condition or disorder (i.e., reversing or improving the pathology and/or symptomatology) such as decreasing the severity of disease; or
(v) eliciting the referenced biological effect.

In various preferred embodiments, the individual may be immunocompromised (having an immune system that has been impaired by disease or treatment, such as an HIV infected patient, and AIDS patient, or a patient receiving chemotherapy or an organ transplant), a pregnant female, fifteen years old or younger, fifty-five years old or older, exposed to contaminated water supplies, and/or exposed to other sources of contamination (fecal matter, blood transfusion, earth, food, etc.) The methods may further comprise administering the compounds disclosed herein to subjects at risk of acquiring an apicomplexan-related disease, such as those with compromised immune systems or that are extremely young in high risk areas.

In other embodiments, the compounds described herein can be used in prophylactic manner. Cryptosporidiosis is usually seen in calves between one and two weeks of age and presents with diarrhea, colic and pain, depression, loss of appetite, and weight loss. Thus, in one embodiment, calves may be treated prophylactically by providing an effective amount of one or more of compounds of the disclosure to limit the contraction or transmission of cryptosporidiosis. In a preferred embodiment, the administering is done within the first 7-8 days after birth (day 1, 2, 3, 4, 5, 6, 7, or 8) when calves are most susceptible to Cryptosporidia infection. Such treatments may be repeated as necessary as would be understood by one skilled in the art.

In another embodiment, infected cattle may be treated by providing a therapeutically effective amount of one or more of compounds of the disclosure to treat cryptosporidiosis. Such treatments may be repeated as necessary as would be understood by one skilled in the art. In this embodiment, the compounds of the invention may be administered together with electrolytes if cattle become dehydrated. If disease is severe, halofuginone can be used in combination with the compounds of the invention to reduce disease severity and prevent spread to other animals.

In another example, lambs are susceptible to cryptosporidiosis and may be provided a therapeutically effective amount of one or more of compounds of the disclosure to limit the contraction or transmission of cryptosporidiosis.

In another example, any or all members of a herd (e.g., cattle, goats, lambs, etc.), may be provided a therapeutically effective amount of one or more of compounds of the disclosure to limit the contraction or transmission of toxoplasmosis or cryptosporidiosis or to rid the herd of cattle of toxoplasmosis or cryptosporidiosis.

In another embodiment, goat kids may be treated prophylactically by providing an effective amount of one or more of compounds of the disclosure to limit the contraction or transmission of cryptosporidiosis. In a preferred embodiment, the administering is done within the first 7-8 days after birth (day 1, 2, 3, 4, 5, 6, 7, or 8) when kids are most susceptible to cryptosporidiosis. Such treatments may be repeated as necessary as would be understood by one skilled in the art. The extent to which a kid is infected seems to be dependent on its age and immune status. Younger animals are much more susceptible to infection than adults. In studies done with lambs, five-day-old lambs had diarrhea for 9-10 days and suffered from a high rate of mortality. Sixty-day-old lambs showed no symptoms when they were infected, and adult sheep completely resisted infection. There is an indication that adults develop an immunity to *Cryptosporidium*, yet this immunity does not seem to be passed to their offspring.

Immune-depressed goats are very susceptible to the disease. This refers to the total immune status, not just protection from cryptosporidiosis. Many situations can cause animals to lack immunity. Animals with severe infections are more susceptible to secondary infections. The most common problem with kids is receiving a deficient amount of colostral antibodies following birth. Whether caused by disease, an imbalanced ration or improper management, animals lacking adequate immunity are much more susceptible to cryptosporidiosis.

In another embodiment, infected goats may be treated by providing a therapeutically effective amount of one or more of compounds of the disclosure to treat cryptosporidiosis. In a preferred embodiment, the goat is a kid.

In another example, pigs are susceptible to cryptosporidiosis and may be provided a therapeutically effective amount of one or more of compounds of the disclosure to limit the contraction or transmission of cryptosporidiosis. In a preferred embodiment, the administering is done within the first 21 days after birth (day 1, 2, 3, 4, 5, 6, 7, 8, 9, 10, 11, 12, 13, 14, 15, 16, 17, 18, 19, 20, or 21) when piglets are most susceptible to cryptosporidiosis and/or most likely In another embodiment, infected pigs may be treated by providing a therapeutically effective amount of one or more of compounds of the disclosure to treat cryptosporidiosis. In a preferred embodiment, the pig is a piglet.

In another example, birds, such as turkeys and chickens, are susceptible to cryptosporidiosis and may be provided an effective amount of one or more of compounds of the disclosure to prevent the contraction or transmission of cryptosporidiosis. In particular, *Cryptosporidium baileyi* can cause respiratory disease in chickens and turkeys. The same species causes infections of the hindgut and cloacal bursa in chickens, turkeys, and ducks. *C. meleagridis* also infects both species. A further species causes respiratory disease in quail. The oocysts are excreted ready sporulated in the feces and infection occurs by inhalation and ingestion. Signs of cryptosporidiosis in poultry include snick, cough, swollen sinuses, low weight gain, and diarrhea. In another embodiment, infected birds may be treated by providing a therapeutically effective amount of one or more of compounds of the disclosure to treat cryptosporidiosis.

In another example, birds, such as turkeys and chickens, are susceptible to coccidiosis or eimeriosis due to *Eimeria* infections and may be provided an effective amount of one or more of compounds of the disclosure to limit the contraction or transmission of coccidiosis, a parasitic disease caused by the development and multiplication of coccidia in the epithelial cells of the intestine. *Eimeria* infections are ubiquitous; they are found wherever chickens or turkeys are reared (traditional, industrial, label or organic/bio farms). Particular strains of *Eimeria* known to infect birds include, but are not limited to, *Eimeria acervuline. Eimeria adenoeides, Eimeria brunette, Eimeria colchici, Eimeria curvata, Eimeria dispersa, Eimeria duodenali, Eimeria fraterculae, Eimeria gallopavonis, Eimeria praecox, Eimeria maxima, Eimeria meleagrimitis, Eimeria mitis, Eimeria necatrix, Eimeria phasiani, Eimeria procera*, and *Eimeria tenella*. In another embodiment, infected birds may be treated by providing a therapeutically effective amount of one or more of compounds of the disclosure to treat coccidiosis In another example, mammals, such as goats, sheep, llamas, alpacas, cattle, rabbits, and mice, are susceptible to coccidiosis or eimeriosis and may be provided an effective amount of one or more of compounds of the disclosure to limit the contraction or spreading of *Eimeria*. Particular strains of *Eimeria* known to infect mammals include, but are not limited to, *Eimeria ahsata, Eimeria alabamensis, Eimeria alijevi, Eimeria apsheronica, Eimeria arloingi, Eimeria arundeli, Eimeria bakuensis, Eimeria bovis, Eimeria cameli, Eimeria caprina, Eimeria caprovina, Eimeria christenseni, Eimeria clethrionomyis, Eimeria coecicola, Eimeria contorta, Eimeria couesii, Eimeria crandallis, Eimeria dammahensis, Eimeria dowleri, Eimeria exigua, Eimeria falciformis, Eimeria farasanii, Eimeria ferrisi, Eimeria flavescens, Eimeria gallatii, Eimeria granulosa, Eimeria hirci, Eimeria intestinalis, Eimeria irresidua, Eimeria intricate, Eimeria jolchijevi, Eimeria krijgsmanni, Eimeria larimerensis, Eimeria macusaniensis, Eimeria magna, Eimeria marconii, Eimeria media, Eimeria melanuri, Eimeria myoxi, Eimeria nagpurensis, Eimeria ninakohlyakimovae, Eimeria ovinoidalis, Eimeria pallida, Eimeria palustris, Eimeria papillata, Eimeria perforans, Eimeria phocae, Eimeria pileata, Eimeria pipistrellu, Eimeria piriformis, Eimeria prionotemni, Eimeria punctate, Eimeria roobroucki, Eimeria saudiensis, Eimeria sealanderi, Eimeria separate, Eimeria stiedae, Eimeria ursini, Eimeria vermiformis, Eimeria weybridgensis, Eimeria wobati*, and *Eimeria zuernii*. In another embodiment, infected mammals may be treated by providing a therapeutically effective amount of one or more of compounds of the disclosure to treat coccidiosis.

The usual age range for animals suffering from coccidiosis or eimeriosis is from three weeks to one year of age, but cattle remain susceptible to coccidiosis or eimeriosis throughout their lives or until they develop acquired immunity. The susceptibility of the animals is influenced by nutritional status (colostrum supply), stress (overstocking, transport, climate, hygiene, etc.), immune status and the occurrence of concurrent diseases.

Infections with multiple *Eimeria* species (pathogenic and non-pathogenic) are common in real life situations. The most important species related to the clinical manifestation of the disease in the stable are *Eimeria bovis* and *Eimeria zuernii*, although other pathogenic coccidia species may also affect the cattle in the stables, such as *Eimeria alabamensis* (animals fed on contaminated hay), which is commonly associated with diarrheic problems in animals that are released to pasture.

"Carrier hosts" shed relatively fewer oocysts and the susceptible "multiplier hosts" pick up the infection and shed many-fold oocysts into the environment. Exposure to multiplier hosts leads to subclinical or mildly clinical infection in animals exposed to a large number of oocysts in the environment. Calves exposed to a large number of oocysts are likely to develop severe coccidiosis. In feedlots where few oocysts are present, stress factors such as weaning, diet, temperature extremes and other variables may make the calves more susceptible to infection and under such conditions the reproductive potential of coccidia in the gut greatly increases.

In goats, although the infection can occur in any goat herd raised under semi and intensive management practices, it is most frequently observed in kids 2 to 4 weeks postweaning. The infection occurs by ingesting the pathogenic sporulated oocyst (sporulated is a form of resistance of the Coccidia). Oocysts can be found in the water or in feed supplies contaminated with feces. Once ingested, oocysts penetrate the cells lining the intestine where they go through several stages of development and cause inflammation and destruction of intestinal cells. Stress is the predisposing factor in kids during the postweaning period. Outbreaks can occur during stressful conditions such as after shipping or when animals are relocated. Outbreaks can also occur during sudden weather changes, after a change in concentrated feed practices, when animals are recovering from a disease, or in worm burden cases. Although coccidiosis can occur year around, a higher incidence occurs during postweaning.

The compounds disclosed herein can be used to treat coccidiosis in combination with standard treatments such as, but not limited to, replacing fluids by administering liquid nutritional supplement orally by nipple bottle until the animal is rehydrated. Animals that have lost 5 percent of their body weight may require intravenous (IV) and/or electrolyte therapy. Treatment may include IV or subcutaneously (SC) fluid therapy with a physiologically balanced electrolyte such as Ringer's, Plasmalyte-A, or Normosol-R. Administer the solution (2 to 5 milliliters per pound) one to three times daily until the animal is rehydrated. Sulfas such as Albon™, Sulmet™, or Di-Methox™, can also be mixed in the drinking water or as a drench for individual goats. An alternative is CORID™ (amprolium).

As used herein, the phrase "therapeutically effective amount" refers to the amount of active compound or pharmaceutical agent that elicits the biological or medicinal response that is being sought in a tissue, system, animal, individual or human by a researcher, veterinarian, medical doctor or other clinician, which includes one or more of the following: (1) preventing the disease; for example, preventing a disease, condition or disorder in an individual who may be predisposed to the disease, condition or disorder but does not yet experience or display the pathology or symptomatology of the disease; (2) inhibiting the disease; for example, inhibiting a disease, condition or disorder in an individual who is experiencing or displaying the pathology or symptomatology of the disease, condition or disorder; and (3) ameliorating the disease; for example, ameliorating a disease, condition or disorder in an individual who is experiencing or displaying the pathology or symptomatology of the disease, condition or disorder (i.e., reversing the pathology and/or symptomatology) such as decreasing the severity of disease.

The pharmaceutical compositions described herein generally comprise a combination of one or more of compounds described herein and a pharmaceutically acceptable carrier, diluent, or excipient. Such compositions are substantially free of non-pharmaceutically acceptable components, i.e., contain amounts of non-pharmaceutically acceptable components lower than permitted by US regulatory requirements at the time of filing this application. In some embodiments of this aspect, if the compound is dissolved or suspended in water, the composition further optionally comprises an additional pharmaceutically acceptable carrier, diluent, or excipient. In one embodiment, the pharmaceutical compositions described herein are solid pharmaceutical compositions (e.g., tablet, capsules, etc.).

These compositions can be prepared in a manner well known in the pharmaceutical art, and can be administered by a variety of routes, depending upon whether local or systemic treatment is desired and upon the area to be treated. Administration may be topical (including ophthalmic and to mucous membranes including intranasal, vaginal and rectal delivery), pulmonary (e.g., by inhalation or insufflation of powders or aerosols, including by nebulizer; intratracheal, intranasal, epidermal and transdermal), ocular, oral or parenteral. Methods for ocular delivery can include topical administration (eye drops), subconjunctival, periocular or intravitreal injection or introduction by balloon catheter or ophthalmic inserts surgically placed in the conjunctival sac. Parenteral administration includes intravenous, intraarterial, subcutaneous, intraperitoneal or intramuscular injection or infusion; or intracranial, e.g., intrathecal or intraventricular, administration. Parenteral administration can be in the form of a single bolus dose, or may be, for example, by a continuous perfusion pump. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

Also, pharmaceutical compositions can contain, as the active ingredient, one or more of the compounds described herein above in combination with one or more pharmaceutically acceptable carriers. In making the compositions described herein, the active ingredient is typically mixed with an excipient, diluted by an excipient or enclosed within such a carrier in the form of, for example, a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

In preparing a formulation, the active compound can be milled to provide the appropriate particle size prior to combining with the other ingredients. If the active compound is substantially insoluble, it can be milled to a particle size of less than 200 mesh. If the active compound is substantially water soluble, the particle size can be adjusted by milling to provide a substantially uniform distribution in the formulation, e.g. about 40 mesh.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions described herein can be formulated so as to provide quick, sustained or delayed release of the active ingredient after administration to the patient by employing procedures known in the art.

The compositions can be formulated in a unit dosage form, each dosage containing from about 5 to about 100 mg, more usually about 10 to about 30 mg, of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

The active compound can be effective over a wide dosage range and is generally administered in a pharmaceutically effective amount. It will be understood, however, that the amount of the compound actually administered will usually be determined by a physician, according to the relevant circumstances, including the condition to be treated, the chosen route of administration, the actual compound administered, the age, weight, and response of the individual patient, the severity of the patient's symptoms, and the like.

For preparing solid compositions such as tablets, the principal active ingredient is mixed with a pharmaceutical excipient to form a solid preformulation composition containing a homogeneous mixture of a compound described herein. When referring to these preformulation compositions as homogeneous, the active ingredient is typically dispersed evenly throughout the composition so that the composition can be readily subdivided into equally effective unit dosage forms such as tablets, pills and capsules. This solid preformulation is then subdivided into unit dosage forms of the type described above containing from, for example, 0.1 to about 500 mg of the active ingredient of a compound described herein.

The tablets or pills can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the compounds and compositions can be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. In some embodiments, the compositions are administered by the oral or nasal respiratory route for local or systemic effect. Compositions in can be nebulized by use of inert gases. Nebulized solutions may be breathed directly from the nebulizing device or the nebulizing device can be attached to a face masks tent, or intermittent positive pressure breathing machine. Solution, suspension, or powder compositions can be administered orally or nasally from devices which deliver the formulation in an appropriate manner.

The amount of compound or composition administered to a patient will vary depending upon what is being administered, the purpose of the administration, such as prophylaxis or therapy, the state of the patient, the manner of administration, and the like. In therapeutic applications, compositions can be administered to a patient already suffering from a disease in an amount sufficient to cure or at least partially arrest the symptoms of the disease and its complications. Effective doses will depend on the disease condition being treated as well as by the judgment of the attending clinician depending upon factors such as the severity of the disease, the age, weight and general condition of the patient, and the like.

The compositions administered to a patient can be in the form of pharmaceutical compositions described above. These compositions can be sterilized by conventional sterilization techniques, or may be sterile filtered. Aqueous solutions can be packaged for use as is, or lyophilized, the lyophilized preparation being combined with a sterile aqueous carrier prior to administration. The pH of the compound preparations typically will be between 3 and 11, more preferably from 5 to 9 and most preferably from 7 to 8. It will be understood that use of certain of the foregoing excipients, carriers, or stabilizers will result in the formation of pharmaceutical salts.

The therapeutic dosage of the compounds can vary according to, for example, the particular use for which the treatment is made, the manner of administration of the compound, the health and condition of the patient, and the judgment of the prescribing physician. The proportion or concentration of a compound described herein in a pharmaceutical composition can vary depending upon a number of factors including dosage, chemical characteristics (e.g., hydrophobicity), and the route of administration. For example, the compounds described herein can be provided in an aqueous physiological buffer solution containing about 0.1 to about 10% w/v of the compound for parenteral administration. Some typical dose ranges are from about 1 µg/kg to about 1 g/kg of body weight per day. In some embodiments, the dose range is from about 0.01 mg/kg to about 100 mg/kg of body weight per day. The dosage is likely to depend on such variables as the type and extent of progression of the disease or disorder, the overall health status of the particular patient, the relative biological efficacy of the compound selected, formulation of the excipient, and its route of administration. Effective doses can be extrapolated from dose-response curves derived from in vitro or animal model test systems.

The compounds described herein can also be formulated in combination with one or more additional active ingredients which can include any pharmaceutical agent such as anti-viral agents, vaccines, antibodies, immune enhancers, immune suppressants, anti-inflammatory agents and the like.

DEFINITIONS

Unless the context clearly requires otherwise, throughout the description and the claims, the words 'comprise', 'comprising', and the like are to be construed in an inclusive sense as opposed to an exclusive or exhaustive sense; that is to say, in the sense of "including, but not limited to". Words using the singular or plural number also include the plural or singular number, respectively. Additionally, the words "herein," "above" and "below" and words of similar import, when used in this application, shall refer to this application as a whole and not to any particular portions of this application.

Terms used herein may be preceded and/or followed by a single dash, "—", or a double dash, "=", to indicate the bond order of the bond between the named substituent and its parent moiety; a single dash indicates a single bond and a double dash indicates a double bond. In the absence of a single or double dash it is understood that a single bond is formed between the substituent and its parent moiety; further, substituents are intended to be read "left to right" unless a dash indicates otherwise. For example, $C_1$-$C_6$alkoxycarbonyloxy and —OC(O)$C_1$-$C_6$alkyl indicate the same functionality; similarly arylalkyl and alkylaryl indicate the same functionality.

The term "alkenyl" as used herein, means a straight or branched chain hydrocarbon containing from 2 to 10 carbons, unless otherwise specified, and containing at least one carbon-carbon double bond. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, 3-decenyl, and 3,7-dimethylocta-2,6-dienyl.

The term "alkyl" as used herein, means a straight or branched chain hydrocarbon containing from 1 to 10 carbon atoms, unless otherwise specified. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl. When an "alkyl" group is a linking group between two other moieties, then it may also be a straight or branched chain; examples include, but are not limited to —CH$_2$—, —CH$_2$CH$_2$—, —CH$_2$CH$_2$CHC(CH$_3$)—, —CH$_2$CH(CH$_2$CH$_3$)CH$_2$—.

The term "alkynyl" as used herein, means a straight or branched chain hydrocarbon group containing from 2 to 10 carbon atoms and containing at least one carbon-carbon triple bond. Representative examples of alkynyl include, but are not limited, to acetylenyl, 1-propynyl, 2-propynyl, 3-butyryl, 2-pentynyl, and 1-butyryl.

The term "aryl," as used herein, means a phenyl (i.e., monocyclic aryl), a bicyclic ring system containing at least one phenyl ring or an aromatic bicyclic ring containing only carbon atoms in the aromatic bicyclic ring system or a multicyclic aryl ring system, provided that the bicyclic or multicyclic aryl ring system does not contain a heteroaryl ring when fully aromatic. The bicyclic aryl can be azulenyl, naphthyl, or a phenyl fused to a monocyclic cycloalkyl, a monocyclic cycloalkenyl, or a monocyclic heterocyclyl. The bicyclic aryl is attached to the parent molecular moiety through any carbon atom contained within the phenyl portion of the bicyclic system, or any carbon atom with the napthyl or azulenyl ring. The fused monocyclic cycloalkyl or monocyclic heterocyclyl portions of the bicyclic aryl are optionally substituted with one or two oxo and/or thia groups. Representative examples of the bicyclic aryls include, but are not limited to, azulenyl, naphthyl, dihydroinden-1-yl, dihydroinden-2-yl, dihydroinden-3-yl, dihydroinden-4-yl, 2,3-dihydroindol-4-yl, 2,3-dihydroindol-5-yl, 2,3-dihydroindol-6-yl, 2,3-dihydroindol-7-yl, inden-1-yl, inden-2-yl, inden-3-yl, inden-4-yl, dihydronaphthalen-2-yl, dihydronaphthalen-3-yl, dihydronaphthalen-4-yl, dihydronaphthalen-1-yl, 5,6,7,8-tetrahydronaphthalen-1-yl, 5,6,7,8-tetrahydronaphthalen-2-yl, 2,3-dihydrobenzofuran-4-yl, 2,3-dihydrobenzofuran-5-yl, 2,3-dihydrobenzofuran-6-yl, 2,3-dihydrobenzofuran-7-yl, benzo[d][1,3]dioxol-4-yl, benzo[d][1,3]dioxol-5-yl, 2H-chromen-2-on-5-yl, 2H-chromen-2-on-6-yl, 2H-chromen-2-on-7-yl, 2H-chromen-2-on-8-yl, isoindoline-1,3-dion-4-yl, isoindoline-1,3-dion-5-yl, inden-1-on-4-yl, inden-1-on-5-yl, inden-1-on-6-yl, inden-1-on-7-yl, 2,3-dihydrobenzo[b][1,4]dioxan-5-yl, 2,3-dihydrobenzo[b][1,4]dioxan-6-yl, 2H-benzo[b][1,4]oxazin3 (4H)-on-5-yl, 2H-benzo[b][1,4]oxazin3 (4H)-on-6-yl, 2H-benzo[b][1,4]oxazin3 (4H)-on-7-yl, 2H-benzo[b][1,4]oxazin3 (4H)-on-8-yl, benzo[d]oxazin-2 (3H)-on-5-yl, benzo[d]oxazin-2(3H)-on-6-yl, benzo[d]oxazin-2 (3H)-on-7-yl, benzo[d]oxazin-2 (3H)-on-8-yl, quinazolin-4 (3H)-on-5-yl, quinazolin-4(3H)-on-6-yl, quinazolin-4(3H)-on-7-yl, quinazolin-4(3H)-on-8-yl, quinoxalin-2(1H)-on-5-yl, quinoxalin-2(1H)-on-6-yl, quinoxalin-2(1H)-on-7-yl, quinoxalin-2(1H)-on-8-yl, benzo[d]thiazol-2 (3H)-on-4-yl, benzo[d]thiazol-2 (3H)-on-5-yl, benzo[d]thiazol-2(3H)-on-6-yl, and, benzo[d]thiazol-2(3H)-on-7-yl. In certain embodiments, the bicyclic aryl is (i) naphthyl or (ii) a phenyl ring fused to either a 5 or 6 membered monocyclic cycloalkyl, a 5 or 6 membered monocyclic cycloalkenyl, or a 5 or 6 membered monocyclic heterocyclyl, wherein the fused cycloalkyl, cycloalkenyl, and heterocyclyl groups are optionally substituted with one or two groups which are independently oxo or thia. Multicyclic aryl groups are a phenyl ring (base ring) fused to either (i) one ring system selected from the group consisting of a bicyclic aryl, a bicyclic cycloalkyl, a bicyclic cycloalkenyl, and a bicyclic heterocyclyl; or (ii) two other ring systems independently selected from the group consisting of a phenyl, a bicyclic aryl, a monocyclic or bicyclic cycloalkyl, a monocyclic or bicyclic cycloalkenyl, and a monocyclic or bicyclic heterocyclyl, provided that when the base ring is fused to a bicyclic cycloalkyl, bicyclic cycloalkenyl, or bicyclic heterocyclyl, then the base ring is fused to the base ring of the a bicyclic cycloalkyl, bicyclic cycloalkenyl, or bicyclic heterocyclyl. The multicyclic aryl is attached to the parent molecular moiety through any carbon atom contained within the base ring. In certain embodiments, multicyclic aryl groups are a phenyl ring (base ring) fused to either (i) one ring system selected from the group consisting of a bicyclic aryl, a bicyclic cycloalkyl, a bicyclic cycloalkenyl, and a bicyclic heterocyclyl; or (ii) two other ring systems independently selected from the group consisting of a phenyl, a monocyclic cycloalkyl, a monocyclic cycloalkenyl, and a monocyclic heterocyclyl, provided that when the base ring is fused to a bicyclic cycloalkyl, bicyclic cycloalkenyl, or bicyclic heterocyclyl, then the base ring is fused to the base ring of the a bicyclic cycloalkyl, bicyclic cycloalkenyl, or bicyclic heterocyclyl. Examples of multicyclic aryl groups include but are not limited to anthracen-9-yl and phenanthren-9-yl.

The term "arylalkyl" and "-alkylaryl" as used herein, means an aryl group, as defined herein, appended to the parent molecular moiety through an alkyl group, as defined herein. Representative examples of arylalkyl include, but are not limited to, benzyl, 2-phenylethyl, 3-phenylpropyl, and 2-naphth-2-ylethyl.

The terms "cyano" and "nitrile" as used herein, mean a —CN group.

The term "cycloalkyl" as used herein, means a monocyclic, bicyclic, or a multicyclic cycloalkyl ring system. Monocyclic ring systems are cyclic hydrocarbon groups containing from 3 to 8 carbon atoms, where such groups can be saturated or unsaturated, but not aromatic. In certain embodiments, cycloalkyl groups are fully saturated. Examples of monocyclic cycloalkyls include cyclopropyl, cyclobutyl, cyclopentyl, cyclopentenyl, cyclohexyl, cyclohexenyl, cycloheptyl, and cyclooctyl. Bicyclic cycloalkyl ring systems are bridged monocyclic rings or fused bicyclic rings. Bridged monocyclic rings contain a monocyclic cycloalkyl ring where two non-adjacent carbon atoms of the monocyclic ring are linked by an alkylene bridge of between one and three additional carbon atoms (i.e., a bridging group of the form —(CH$_2$)$_w$—, where w is 1, 2, or 3). Representative examples of bicyclic ring systems include, but are not limited to, bicyclo[3.1.1]heptane, bicyclo[2.2.1]heptane, bicyclo[2.2.2]octane, bicyclo[3.2.2]nonane, bicyclo[3.3.1]nonane, and bicyclo[4.2.1]nonane. Fused bicyclic cycloalkyl ring systems contain a monocyclic cycloalkyl ring fused to either a phenyl, a monocyclic cycloalkyl, a monocyclic cycloalkenyl, a monocyclic heterocyclyl, or a monocyclic heteroaryl. The bridged or fused bicyclic cycloalkyl is attached to the parent molecular moiety through any carbon atom contained within the monocyclic cycloalkyl ring. Cycloalkyl groups are optionally substituted with one or two groups which are independently oxo or thia. In certain embodiments, the fused bicyclic cycloalkyl is a 5 or 6 membered monocyclic cycloalkyl ring fused to either a phenyl ring, a 5 or 6 membered monocyclic cycloalkyl, a 5 or 6 membered monocyclic cycloalkenyl, a 5 or 6 membered monocyclic heterocyclyl, or a 5 or 6 membered monocyclic heteroaryl, wherein the fused bicyclic cycloalkyl is optionally substituted by one or two groups which are independently oxo or thia. Multicyclic cycloalkyl ring systems are a monocyclic cycloalkyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two other rings systems independently selected from the group consisting of a phenyl, a bicyclic aryl, a monocyclic or bicyclic heteroaryl, a monocyclic or bicyclic cycloalkyl, a monocyclic or bicyclic cycloalkenyl, and a monocyclic or bicyclic heterocyclyl. The multicyclic cycloalkyl is attached to the parent molecular moiety through any carbon atom contained within the base ring. In certain embodiments, multicyclic cycloalkyl ring systems are a monocyclic cycloalkyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two other rings systems independently selected from the group consisting of a phenyl, a monocyclic heteroaryl, a monocyclic cycloalkyl, a monocyclic cycloalkenyl, and a monocyclic heterocyclyl. Examples of multicyclic cycloalkyl groups include, but are not limited to tetradecahydrophenanthrenyl, perhydrophenothiazin-1-yl, and perhydrophenoxazin-1-yl.

"Cycloalkenyl" as used herein refers to a monocyclic, bicyclic, or a multicyclic cycloalkenyl ring system. Monocyclic ring systems are cyclic hydrocarbon groups containing from 3 to 8 carbon atoms, where such groups are unsaturated (i.e., containing at least one annular carbon-carbon double bond), but not aromatic. Examples of monocyclic ring systems include cyclopentenyl and cyclohexenyl. Bicyclic cycloalkenyl rings are bridged monocyclic rings or a fused bicyclic rings. Bridged monocyclic rings contain a monocyclic cycloalkenyl ring where two non-adjacent carbon atoms of the monocyclic ring are linked by an alkylene bridge of between one and three additional carbon atoms (i.e., a bridging group of the form —$(CH_2)_w$—, where w is 1, 2, or 3). Representative examples of bicyclic cycloalkenyls include, but are not limited to, norbornenyl and bicyclo[2.2.2]oct-2-enyl. Fused bicyclic cycloalkenyl ring systems contain a monocyclic cycloalkenyl ring fused to either a phenyl, a monocyclic cycloalkyl, a monocyclic cycloalkenyl, a monocyclic heterocyclyl, or a monocyclic heteroaryl. The bridged or fused bicyclic cycloalkenyl is attached to the parent molecular moiety through any carbon atom contained within the monocyclic cycloalkenyl ring. Cycloalkenyl groups are optionally substituted with one or two groups which are independently oxo or thia. Multicyclic cycloalkenyl rings contain a monocyclic cycloalkenyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two rings systems independently selected from the group consisting of a phenyl, a bicyclic aryl, a monocyclic or bicyclic heteroaryl, a monocyclic or bicyclic cycloalkyl, a monocyclic or bicyclic cycloalkenyl, and a monocyclic or bicyclic heterocyclyl. The multicyclic cycloalkenyl is attached to the parent molecular moiety through any carbon atom contained within the base ring. IN certain embodiments, multicyclic cycloalkenyl rings contain a monocyclic cycloalkenyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two rings systems independently selected from the group consisting of a phenyl, a monocyclic heteroaryl, a monocyclic cycloalkyl, a monocyclic cycloalkenyl, and a monocyclic heterocyclyl.

The term "halo" or "halogen" as used herein, means —Cl, —Br, —I or —F.

The term "haloalkyl" as used herein, means at least one halogen, as defined herein, appended to the parent molecular moiety through an alkyl group, as defined herein. Representative examples of haloalkyl include, but are not limited to, chloromethyl, 2-fluoroethyl, trifluoromethyl, pentafluoroethyl, and 2-chloro-3-fluoropentyl.

The term "heteroaryl," as used herein, means a monocyclic, bicyclic, or a multicyclic heteroaryl ring system. The monocyclic heteroaryl can be a 5 or 6 membered ring. The 5 membered ring consists of two double bonds and one, two, three or four nitrogen atoms and optionally one oxygen or sulfur atom. The 6 membered ring consists of three double bonds and one, two, three or four nitrogen atoms. The 5 or 6 membered heteroaryl is connected to the parent molecular moiety through any carbon atom or any nitrogen atom contained within the heteroaryl. Representative examples of monocyclic heteroaryl include, but are not limited to, furyl, imidazolyl, isoxazolyl, isothiazolyl, oxadiazolyl, oxazolyl, pyridinyl, pyridazinyl, pyrimidinyl, pyrazinyl, pyrazolyl, pyrrolyl, tetrazolyl, thiadiazolyl, thiazolyl, thienyl, triazolyl, and triazinyl. The bicyclic heteroaryl consists of a monocyclic heteroaryl fused to a phenyl, a monocyclic cycloalkyl, a monocyclic cycloalkenyl, a monocyclic heterocyclyl, or a monocyclic heteroaryl. The fused cycloalkyl or heterocyclyl portion of the bicyclic heteroaryl group is optionally substituted with one or two groups which are independently oxo or thia. When the bicyclic heteroaryl contains a fused cycloalkyl, cycloalkenyl, or heterocyclyl ring, then the bicyclic heteroaryl group is connected to the parent molecular moiety through any carbon or nitrogen atom contained within the monocyclic heteroaryl portion of the bicyclic ring system. When the bicyclic heteroaryl is a monocyclic heteroaryl fused to a phenyl ring or a monocyclic heteroaryl, then the bicyclic heteroaryl group is connected to the parent molecular moiety through any carbon atom or nitrogen atom within the bicyclic ring system. Representative examples of bicyclic heteroaryl include, but are not limited to, benzimidazolyl, benzofuranyl, benzothienyl, benzoxadiazolyl, benzoxathiadiazolyl, benzothiazolyl, cinnolinyl, 5,6-dihydroquinolin-2-yl, 5,6-dihydroisoquinolin-1-yl, furopyridinyl, indazolyl, indolyl, isoquinolinyl, naphthyridinyl, quinolinyl, purinyl, 5,6,7,8-tetrahydroquinolin-2-yl, 5,6,7,8-tetrahydroquinolin-3-yl, 5,6,7,8-tetrahydroquinolin-4-yl, 5,6,7,8-tetrahydroisoquinolin-1-yl, thienopyridinyl, 4,5,6,7-tetrahydrobenzo[c][1,2,5]oxadiazolyl, and 6,7-dihydrobenzo[c][1,2,5]oxadiazol-4 (5H)-onyl. In certain embodiments, the fused bicyclic heteroaryl is a 5 or 6 membered monocyclic heteroaryl ring fused to either a phenyl ring, a 5 or 6 membered monocyclic cycloalkyl, a 5 or 6 membered monocyclic cycloalkenyl, a 5 or 6 membered monocyclic heterocyclyl, or a 5 or 6 membered monocyclic heteroaryl, wherein the fused cycloalkyl, cycloalkenyl, and heterocyclyl groups are optionally substituted with one or two groups which are independently oxo or thia. The multicyclic heteroaryl group is a monocyclic heteroaryl ring (base ring) fused to either (i) one ring system selected from the group consisting of a bicyclic aryl, a bicyclic heteroaryl, a bicyclic heterocyclyl, a bicyclic cycloalkenyl, and a bicyclic cycloalkyl; or (ii) two ring systems selected from the group consisting of a phenyl, a bicyclic aryl, a monocyclic or bicyclic heteroaryl, a monocyclic or bicyclic heterocyclyl, a monocyclic or bicyclic cycloalkenyl, and a monocyclic or bicyclic cycloalkyl. The multicyclic heteroaryl group is connected to the parent molecular moiety through any carbon atom or nitrogen atom contained within the base ring. In certain embodiments, multicyclic heteroaryl groups are a monocyclic heteroaryl ring (base ring) fused to either (i) one ring system selected from the group consisting of a bicyclic aryl, a bicyclic heteroaryl, a bicyclic heterocyclyl, a bicyclic cycloalkenyl, and a bicyclic cycloalkyl; or (ii) two ring systems selected from the group consisting of a phenyl, a monocyclic heteroaryl, a monocyclic heterocyclyl, a monocyclic cycloalkenyl, and a monocyclic cycloalkyl. Examples of multicyclic heteroaryls include, but are not limited to 5H-[1,2,4]triazino[5,6-b]indol-5-yl, 2,3,4,9-tetrahydro-1H-carbazol-9-yl, 9H-pyrido[3,4-b]indol-9-yl, 9H-carbazol-9-yl, and acridin-9-yl.

The term "heteroarylalkyl" and "-alkylheteroaryl" as used herein, means a heteroaryl, as defined herein, appended to the parent molecular moiety through an alkyl group, as defined herein. Representative examples of heteroarylalkyl include, but are not limited to, fur-3-ylmethyl, 1H-imidazol-2-ylmethyl, 1H-imidazol-4-ylmethyl, 1-(pyridin-4-yl)ethyl, pyridin-3-ylmethyl, pyridin-4-ylmethyl, pyrimidin-5-ylmethyl, 2-(pyrimidin-2-yl)propyl, thien-2-ylmethyl, and thien-3-ylmethyl.

The term "heterocyclyl" as used herein, means a monocyclic, bicyclic, or multicyclic heterocycle. The monocyclic heterocycle is a 3, 4, 5, 6 or 7 membered ring containing at least one heteroatom independently selected from the group consisting of O, N, and S where the ring is saturated or unsaturated, but not aromatic. The 3 or 4 membered ring contains 1 heteroatom selected from the group consisting of O, N and S. The 5 membered ring can contain zero or one double bond and one, two or three heteroatoms selected from the group consisting of O, N and S. The 6 or 7 membered ring contains zero, one or two double bonds and one, two or three heteroatoms selected from the group consisting of O, N and S. The monocyclic heterocycle is connected to the parent molecular moiety through any carbon atom or any nitrogen atom contained within the monocyclic heterocycle. Representative examples of monocyclic heterocycle include, but are not limited to, azetidinyl, azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, piperazinyl, piperidinyl, pyranyl, pyrazolinyl, pyrazolidinyl, pyrrolinyl, pyrrolidinyl, tetrahydrofuranyl, tetrahydrothienyl, thiadiazolinyl, thiadiazolidinyl, thiazolinyl, thiazolidinyl, thiomorpholinyl, 1,1-dioxidothiomorpholinyl (thiomorpholine sulfone), thiopyranyl, and trithianyl. The bicyclic heterocycle is a monocyclic heterocycle fused to either a phenyl, a monocyclic cycloalkyl, a monocyclic cycloalkenyl, a monocyclic heterocycle, or a monocyclic heteroaryl. The bicyclic heterocycle is connected to the parent molecular moiety through any carbon atom or any nitrogen atom contained within the monocyclic heterocycle portion of the bicyclic ring system. Representative examples of bicyclic heterocyclyls include, but are not limited to, 2,3-dihydrobenzofuran-2-yl, 2,3-dihydrobenzofuran-3-yl, indolin-1-yl, indolin-2-yl, indolin-3-yl, 2,3-dihydrobenzothien-2-yl, decahydroquinolinyl, decahydroisoquinolinyl, octahydro-1H-indolyl, and octahydrobenzofuranyl. Heterocyclyl groups are optionally substituted with one or two groups which are independently oxo or thia. In certain embodiments, the bicyclic heterocyclyl is a 5 or 6 membered monocyclic heterocyclyl ring fused to phenyl ring, a 5 or 6 membered monocyclic cycloalkyl, a 5 or 6 membered monocyclic cycloalkenyl, a 5 or 6 membered monocyclic heterocyclyl, or a 5 or 6 membered monocyclic heteroaryl, wherein the bicyclic heterocyclyl is optionally substituted by one or two groups which are independently oxo or thia. Multicyclic heterocyclyl ring systems are a monocyclic heterocyclyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two other rings systems independently selected from the group consisting of a phenyl, a bicyclic aryl, a monocyclic or bicyclic heteroaryl, a monocyclic or bicyclic cycloalkyl, a monocyclic or bicyclic cycloalkenyl, and a monocyclic or bicyclic heterocyclyl. The multicyclic heterocyclyl is attached to the parent molecular moiety through any carbon atom or nitrogen atom contained within the base ring. In certain embodiments, multicyclic heterocyclyl ring systems are a monocyclic heterocyclyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two other rings systems independently selected from the group consisting of a phenyl, a monocyclic heteroaryl, a monocyclic cycloalkyl, a monocyclic cycloalkenyl, and a monocyclic heterocyclyl. Examples of multicyclic heterocyclyl groups include, but are not limited to 10H-phenothiazin-10-yl, 9,10-dihydroacridin-9-yl, 9,10-dihydroacridin-10-yl, 10H-phenoxazin-10-yl, 10,11-dihydro-5H-dibenzo[b,f]azepin-5-yl, 1,2,3,4-tetrahydropyrido[4,3-g]isoquinolin-2-yl, 12H-benzo[b]phenoxazin-12-yl, and do decahydro-1H-carbazol-9-yl.

The term "nitro" as used herein, means a —NO$_2$ group.

The term "oxo" as used herein means a =O group.

The term "saturated" as used herein means the referenced chemical structure does not contain any multiple carbon-carbon bonds. For example, a saturated cycloalkyl group as defined herein includes cyclohexyl, cyclopropyl, and the like.

The term "thia" as used herein means a =S group.

The term "unsaturated" as used herein means the referenced chemical structure contains at least one multiple carbon-carbon bond, but is not aromatic. For example, a unsaturated cycloalkyl group as defined herein includes cyclohexenyl, cyclopentenyl, cyclohexadienyl, and the like.

As used herein, the phrase "pharmaceutically acceptable salt" refers to both pharmaceutically acceptable acid and base addition salts and solvates. Such pharmaceutically acceptable salts include salts of acids such as hydrochloric, phosphoric, hydrobromic, sulfuric, sulfinic, formic, toluenesulfonic, methanesulfonic, nitric, benzoic, citric, tartaric, maleic, hydroiodic, alkanoic such as acetic, HOOC—(CH$_2$)$_n$—COOH where n is 0-4, and the like. Non-toxic pharmaceutical base addition salts include salts of bases such as sodium, potassium, calcium, ammonium, and the like. Those skilled in the art will recognize a wide variety of non-toxic pharmaceutically acceptable addition salts.

EXAMPLES

Unless otherwise stated, all chemicals were purchased from commercial suppliers and used without further purification. The microwave irradiation was performed in a CEM Discover System. The final purity of all compounds was determined by analytical LCMS with Phenomenex Onyx Monolithic C18 column (4.6 mm×100 mm). The products were detected by UV at 220 nm. All compounds were determined to be >95% pure by this method. The purification by preparative HPLC was performed on Waters Xterra Prep RP18 OBD 5 μM (19 mm×50 mm) with CH$_3$CN/H$_2$O and 0.1% TFA as eluent. The mass spectra were recorded with an Agilent Ion Trap Mass Spectrometer. NMR spectra were recorded on either a Bruker 500 MHz spectrometer or a Bruker 300 MHz spectrometer at ambient temperature. Inhibitors were synthesized through several different routes, as represented in Schemes 1-3. Syntheses of compounds 2, 4, 7 and 9 have been previously reported in Johnson et al., *J. Med. Chem.* 55, 2416-2426 (2012), incorporated by reference. All other syntheses and compound characterization data are presented below.

Scheme 1

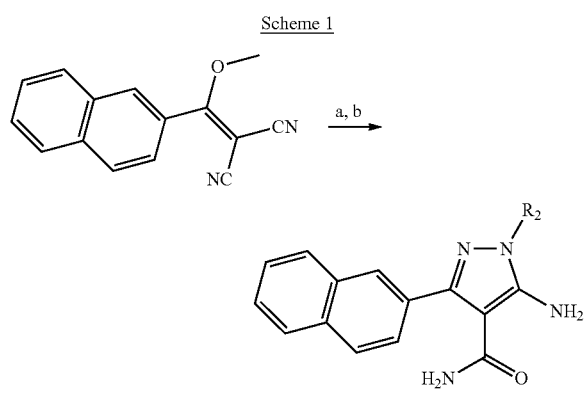

Reagents and conditions
(a) R$_1$—NHNH$_2$, EtOH, microwave, 100° C., 30 min;
(b) NaOH, EtOH, microwave, 110° C., 10 min.

General Procedure A (Examples 1, 12-23):

A mixture of 2-(methoxy(naphthalene-7-yl)methylene)malononitrile (50 mg, 0.21 mmol) prepared as previously reported and the appropriate alkyl hydrazine (1.2 equiv) were dissolved in ethanol (1 ml) in an capped microwave tube. The reaction mixture was microwave irradiated at 100° C. for 30 min. After cooling down, 0.2 ml of saturated aqueous NaOH was added in situ and the solution was microwave irradiated at 110° C. for 20 min. After cooling down to 0° C., concentrated HCl was added slowly to neutralize the solution. The solution was extracted with ethyl acetate, washed with water twice. The solvent was removed and the residue was dissolved in methanol and purified by preparative HPLC with an acetonitrile/water gradient with 0.1% TFA to yield the final products. Using this procedure, only one regioisomer as indicated in the scheme was isolated from the reaction.

Scheme 2

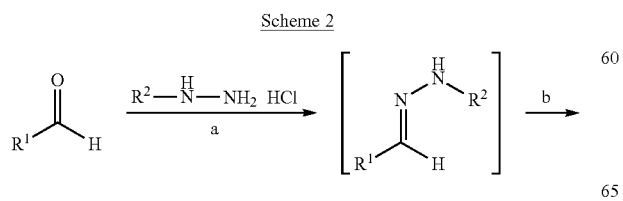

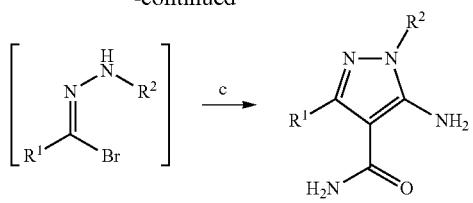

Reagents and conditions
(a) t-butylhydrazine, DMF or (a) DIPEA, EtOH, Microwave, 70° C., DMF;
(b) NBS, DMF, 0° C.;
(c) EtONa, cyanoacetamide, EtOH, or (c) NaH, cyanoacetamide, DMF.

General Procedure B (Examples 3, 24, 25, 27, 30, 34-39):

A mixture of the appropriate aromatic aldehyde (1.5 mmole) and powder t-butylhydrazine HCl salt (1.1 equiv) with DIPEA (1.1 equiv) were dissolved in 3 ml of anhydrous DMF in a capped microwave tube. The mixture was microwave irradiated at 80° C. for 20 min or stirred at room temperature for 2 h. After cooling down to 0° C., to the solution was slowly added NBS (1.1 equiv) in 0.5 ml DMF. The mixture was kept at 0° C. and stirred for 2 h. Cyanoacetamide anion was generated by treatment of cyanoacetamide (1.1 equiv) in 3 ml of anhydrous ethanol with 2.5 equiv of sodium ethoxide. This mixture was mixed with the above bromohydrazone DMF solution. The reaction was stirred overnight at room temperature. After most solvents were removed, the residue was diluted with ethyl acetate and washed with water, brine, dried over Na$_2$SO$_4$ and concentrated under reduced pressure. Purification via flash chromatography on silica gel eluted with MeOH-DCM and further with preparative HPLC gave the HPLC pure final products.

Scheme 3

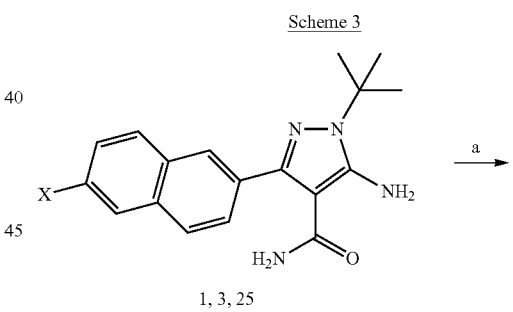

1, 3, 25

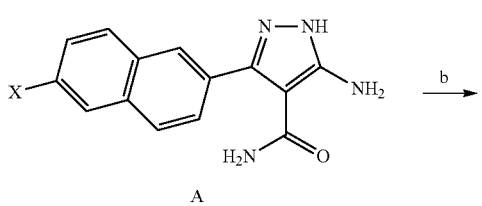

A

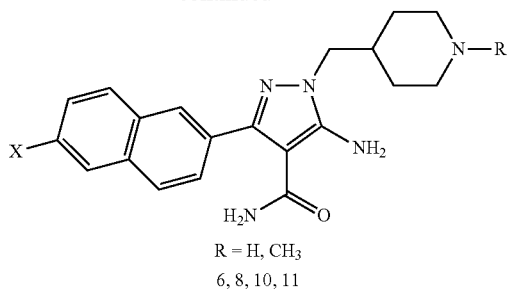

R = H, CH₃
6, 8, 10, 11

Reagents and conditions
(a) concentrated H₂SO₄, 1 h;
(b) 4-Methylsulfonyloxypiperidine, DMF, K₂CO₃, microwave, 90° C., 30 min.

General Procedure C (Examples 6, 8, 10, 11):

1, 3 and 25 were treated with 1 ml of concentrated sulfuric acid respectively for 1 h at room temperature. After cooling down to 0° C., solid NaOH was added in small portions until the solution became neutral or basic. The slurry mixture was slowly diluted with water and extracted with ethyl acetate twice. The organic extract was washed with water, brine, dried over Na₂SO₄ and concentrated under reduced pressure to give intermediate A. 4-Methylsulfonyloxypiperidine (0.8 mmol) and A (0.08 mmol) in 1 ml of DMF containing K₂CO₃ (1.0 mmol) was microwave irradiated at 90° C. for 30 min. After solvent was removed, the residues were extracted with ethyl acetate, washed with water, brine, dried over Na₂SO₄ and concentrated under reduced pressure. The mixture was Boc deprotected if necessary before HPLC purification. The preparative HPLC purification can separate the isomers in N-1 and N-2 positions and the N-1 position product was collected and confirmed by ¹H NMR in d6-DMSO.

Example 1

Compound 1, Also 1439

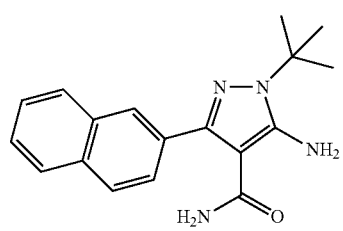

1: 5-amino-1-tert-butyl-3-(naphthalen-2-yl)-1H-pyrazole-4-carboxamide was synthesized using t-butyl hydrazine following General Procedure A. ¹H NMR (500 MHz, CDCl₃) δ 8.05 (1H, s), 7.92 (1H, d, J 8.6), 7.88 (2H, dd, J 8.7, 4.6), 7.65 (1H, d, J 1.8), 7.56-7.48 (2H, m), 5.72 (2H, s), 1.70 (9H, s). MS (ESI) (M+H)⁺=309.6.

Comparative Example 2

Compound 2

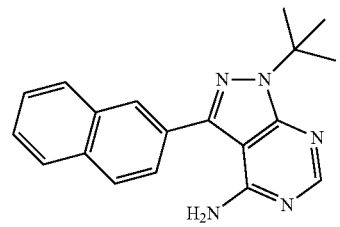

2: 1-tert-butyl-3-(naphthalen-2-yl)-1H-pyrazolo[3,4-d]pyrimidin-4-amine

Example 3

Compound 3, Also 1473

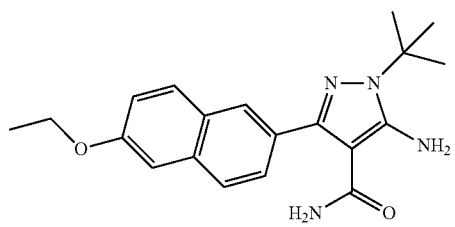

3: 5-amino-1-tert-butyl-3-(6-ethoxynaphthalen-2-yl)-1H-pyrazole-4-carboxamide was synthesized using 6-ethoxynaphthalene-2-carboxaldehyde following General Procedure B.

¹H NMR (500 MHz, CDCl₃) δ 7.94 (1H, s), 7.78 (2H, dd, J 12.5, 8.7), 7.58 (1H, dd, J 8.0, 1.1), 7.18 (1H, dd, J 8.8, 2.5), 7.14 (1H, d, J 2.4), 5.41 (2H, s), 4.23-4.11 (2H, m), 1.69 (9H, s), 1.49 (3H, t, J 5.8). MS (ESI) (M+H)⁺=353.6.

Comparative Example 4

Compound 4, Also 1281

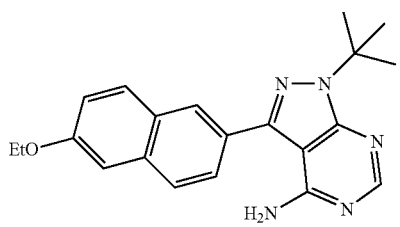

4: 1-tert-butyl-3-(6-ethoxynaphthalen-2-yl)-1H-pyrazolo[3,4-d]pyrimidin-4-amine

Example 5

Compound 5, Also 1503

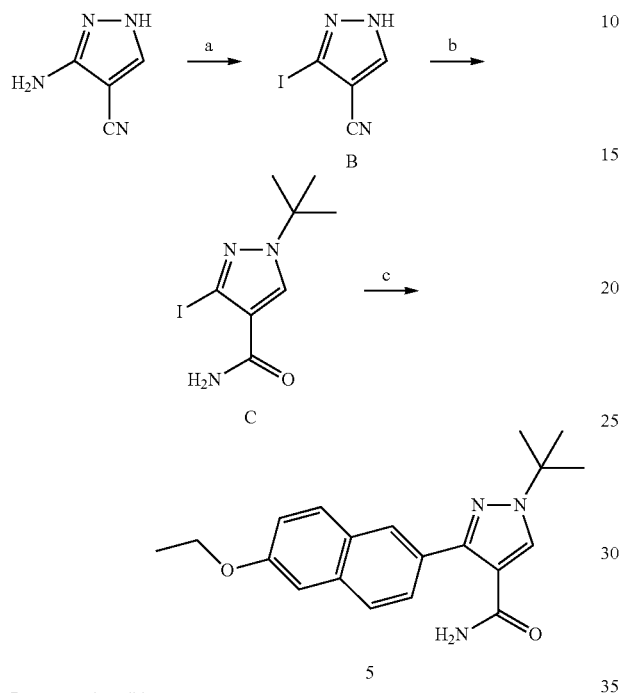

Reagents and conditions
(a) NaNO₂, KI, HCl, H₂O;
(b) ᵗBuOH, H₂SO₄;
(c) DME, H₂O, K₂CO₃, Pd(PPh₃)₄, (6-ethoxynaphthalen-2yl)boronic acid, microwave, 85° C., 20 min.

Intermediate B: To a stirred suspension of 1H 3-amino-1H-pyrazole-4-carbonitrile (1.08 g, 10 mmol) in concentrated HCl (13.0 ml) was added a solution of sodium nitrite (1.38 g, 20 mmol) in water (3.0 ml) over 5 min at 0° C. To the resulting reaction mixture was added a solution of KI (4.1 g, 25 mmol) in water (7.0 ml) over 10 min. The reaction mixture was stirred for 5 min further, then extracted with ether (3×30 ml) and the combined organic extracts were washed with Na₂S₂O₃ (2×30 ml), dried over Na₂SO₄ and concentrated under reduced pressure to give 1.63 g of B as light yellow solid, yield: 74.6%. MS (ESI) (M+H)⁺=220.9.

Intermediate C: To a solution of B (110 mg, 0.5 mmol) in tert-butanol (5 ml) was added sulfuric acid (0.110 ml). The reaction mixture was heated at 100° C. for 3 h. After cooling down to 0° C., solid NaOH was added in small portions until the solution became neutral or basic. The slurry mixture was slowly diluted with water and extracted with ethyl acetate twice. The organic extract was washed with water, brine, dried over Na₂SO₄ and concentrated under reduced pressure. Purification via flash chromatography on silica gel gave 50 mg of intermediate C as a white solid, yield: 34.1%. MS (ESI) (M+H)⁺=294.8.

1-tert-butyl-3-(6-ethoxynaphthalen-2-yl)-1H-pyrazole-4-carboxamide (5): To a solution of C (20 mg, 0.068 mmol) in a mixture of DME:H₂O=3:1 (4 ml) was added K₂CO₃ (28 mg, 0.2 mmol), Pd(PPh₃)₄ (8 mg, 0.007 mmol) and (6-ethoxynaphthalen-2yl)boronic acid (16 mg, 0.075 mmol). The mixture was microwave irradiated at 85° C. for 20 min. After cooling down to room temperature, ethyl acetate was added and organic layer was washed with water, brine, dried over Na₂SO₄ and concentrated under reduced pressure. Purification via flash chromatography on silica gel eluted with MeOH-DCM and further with preparative HPLC gave the HPLC pure final product, 1-tert-butyl-3-(6-ethoxynaphthalen-2-yl)-1H-pyrazole-4-carboxamide. ¹H NMR (300 MHz, DMSO) δ 8.36 (1H, s), 8.23 (1H, s), 7.81 (3 H, m), 7.42 (1H, s), 7.32 (1H, s), 7.16 (1H, d, J 8.9), 7.01 (1H, s), 4.17 (2H, q, J 7.1), 1.60 (9H, s), 1.42 (3H, t, J 6.9). MS (ESI) (M+H)⁺=338.8.

Example 6

Compound 6, Also 1447

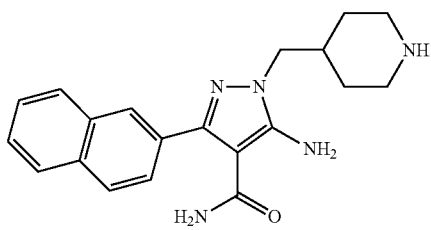

6: 5-amino-3-(naphthalen-2-yl)-1-(piperidin-4-ylmethyl)-1H-pyrazole-4-carboxamide was synthesized using 1-Boc-4-Methanesulfonyloxymethyl-piperidine and 1 which was pre-treated with sulfuric acid following General Procedure C or using 4-(hydrazinylmethyl)-piperidine following General Procedure A. ¹H NMR (500 MHz, MeOD) δ 8.19 (1H, s), 8.04 (1H, d, J 8.4), 7.95 (2H, m), 7.65 (1H, d, J 8.4), 7.62-7.54 (2H, m), 4.13 (2H, d, J 7.0), 3.41 (2H, d, J 13.6), 2.99 (2H, m), 2.30 (1H, s), 1.92 (2H, d, J 12.6), 1.63 (2H, m). MS (ESI) (M+H)⁺=350.5.

Comparative Example 7

Compound 7, Also 1291

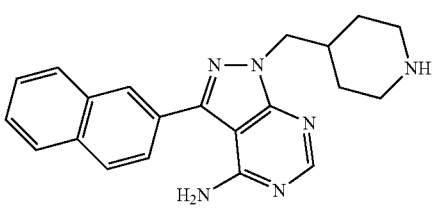

7: 3-(naphthalen-2-yl)-1-(piperidin-4-ylmethyl)-1H-pyrazolo[3,4-d]pyrimidin-4-amine Example 8

Compound 8, Also 1516

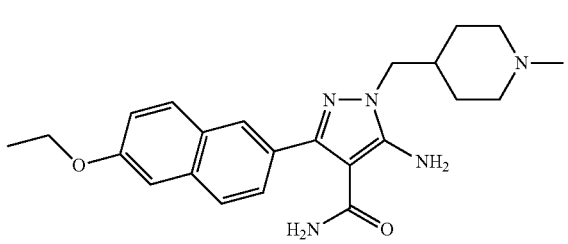

8: 5-amino-3-(6-ethoxynaphthalen-2-yl)-1-((1-methylpiperidin-4-yl)methyl)-1H-pyrazole-4-carboxamide was synthesized using 1-methyl-4-methanesulfonyloxymethylpiperidine and 3, which was pre-treated with sulfuric acid following General Procedure C. $^1$H NMR (500 MHz, MeOD) δ 8.09 (1H, d, J 7.4), 7.93 (1H, d, J 8.6), 7.86 (1H, dd, J 8.4, 3.9), 7.60 (1H, d, J 8.6), 7.30 (1H, d, J 2.0), 7.21 (1H, dd, J 8.6, 2.0), 4.27-4.10 (4H, m), 3.71 (2H, m), 3.06 (2H, m), 2.99-2.86 (3H, m), 2.83 (1 H, m), 2.26 (1H, m), 1.99 (2H, m), 1.72 (1H, m), 1.44 (3H, t, J 7.0). MS (ESI) (M+H)$^+$=408.6.

Comparative Example 9

Compound 9, Also 1294

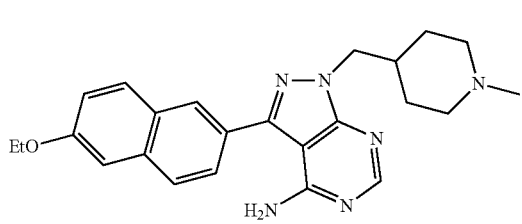

9: 3-(6-ethoxynaphthalen-2-yl)-1-((1-methylpiperidin-4-yl)methyl)-1H-pyrazolo[3,4-d]pyrimidin-4-amine.

Example 10

Compound 10, Also 1501

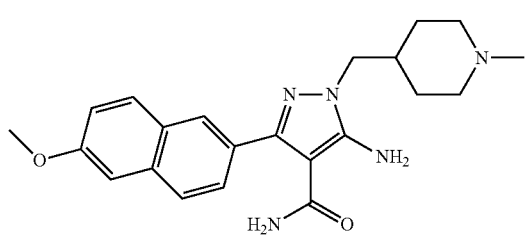

10: 5-amino-3-(6-methoxynaphthalen-2-yl)-1-((1-methylpiperidin-4-yl)methyl)-1H-pyrazole-4-carboxamide was synthesized using compound 11 and 1-methyl-4-Methanesulfonyloxymethylpiperidine following General Procedure C. $^1$H NMR (500 MHz, MeOD) δ 8.11 (1H, s), 7.95 (1H, d, J 8.5), 7.87 (1H, m), 7.61 (1H, d, J 8.5), 7.32 (1H, d, J 2.2), 7.22 (1H, m), 4.20 (2H, m), 3.91 (3H, s), 3.73-3.60 (1H, m), 3.54 (1H, m), 3.19 (1H, m), 3.13-2.99 (1H, m), 2.91 (3H, s), 2.41 (1H, m), 2.28 (1H, m), 2.05 (2H, m), 1.74 (1H, m). MS (ESI) (M+H)$^+$=394.5.

Example 11

Compound 11, Also 1504

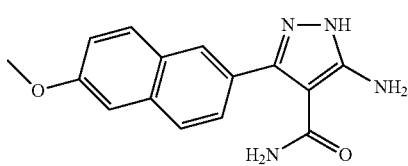

11: 5-amino-3-(6-methoxynaphthalen-2-yl)-1H-pyrazole-4-carboxamide was synthesized from 25 following General Procedure C as one of the intermediate A. $^1$H NMR (500 MHz, MeOD) δ 7.96 (1H, s), 7.90 (1H, d, J 8.5), 7.83 (1H, d, J 9.0), 7.56 (1H, m), 7.30 (1H, t, J 3.7), 7.20 (1H, m), 3.30 (3H, s). MS (ESI) (M+H)$^+$=283.6.

Example 12

Compound 12, Also 1491

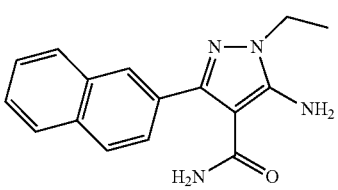

12: 5-amino-1-ethyl-3-(naphthalen-2-yl)-1H-pyrazole-4-carboxamide was synthesized using ethyl hydrazine following General Procedure A. $^1$H NMR (500 MHz, CDCl$_3$) δ 8.06 (1H, d, J 1.2), 7.93 (1H, d, J 8.4), 7.88 (2H, dd, J 6.0, 3.4), 7.66 (1H, dd, J 8.4, 1.6), 7.57-7.48 (2H, m), 5.44 (2H, s), 4.01 (2H, q, J 7.3), 1.46 (3H, t, J 7.3). MS (ESI) (M+H)$^+$=281.8.

Example 13

Compound 13, Also 1492

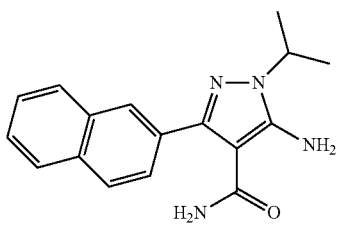

13: 5-amino-1-isopropyl-3-(naphthalen-2-yl)-1H-pyrazole-4-carboxamide was synthesized using isopropylhydrazine following General Procedure A. $^1$H NMR (500 MHz, CDCl$_3$) δ 8.05 (1H, s), 7.93 (1H, d, J 8.5), 7.88 (2H, dd, J 8.5, 5.2), 7.66 (1H, d, J 3.4), 7.56-7.48 (2H, m), 5.45 (2H, s), 5.30 (2H, s), 4.35-4.22 (1H, m), 1.53 (6H, d, J 6.6). MS (ESI) (M+H)$^+$=295.7.

Example 14

Compound 14, Also 1493

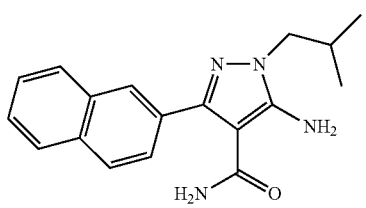

14: 5-amino-1-isobutyl-3-(naphthalen-2-yl)-1H-pyrazole-4-carboxamide was synthesized using isobutylhydrazine following General Procedure A. $^1$H NMR (500 MHz, CDCl$_3$) δ 8.05 (1H, s), 7.93 (1H, d, J 8.4), 7.90-7.83 (2H, m), 7.65 (1H, dd, J 8.4, 1.7), 7.57-7.48 (2H, m), 5.45 (2H, s), 5.32 (2H, s), 3.75 (2H, d, J 7.4), 2.38-2.23 (1H, m), 0.98 (6H, m). MS (ESI) (M+H)$^+$=309.7.

Example 15

Compound 15, Also 1495

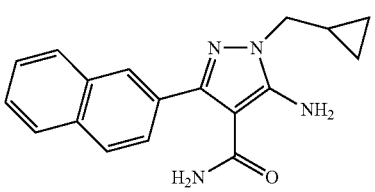

15: 5-amino-1-(cyclopropylmethyl)-3-(naphthalen-2-yl)-1H-pyrazole-4-carboxamide was synthesized using cyclopropylmethylhydrazine following General Procedure A. $^1$H NMR (500 MHz, CDCl$_3$) δ 8.06 (1H, s), 7.94 (1H, d, J 8.3), 7.91-7.86 (2H, m), 7.66 (1H, dd, J 8.4, 1.7), 7.56-7.51 (2H, m), 5.48 (2H, s), 3.91 (2H, d, J 6.6), 1.36-1.23 (1H, m), 0.66 (2H, m), 0.47-0.40 (2H, m). MS (ESI) (M+H)$^+$=307.8.

Example 16

Compound 16, Also 1496

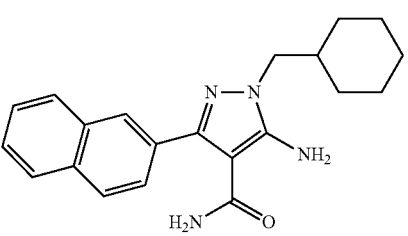

16: 5-amino-1-(cyclohexylmethyl)-3-(naphthalen-2-yl)-1H-pyrazole-4-carboxamide was synthesized using 1-(cyclohexylmethyl)hydrazine following General Procedure A. $^1$H NMR (500 MHz, CDCl$_3$) δ 8.04 (1H, s), 7.98-7.82 (3H, m), 7.64 (1H, m), 7.59-7.47 (2H, m), 3.77 (2H, d, J 7.3), 2.09-1.90 (1H, m), 1.72 (5H, m), 1.23 (3H, m), 1.03 (2H, m). MS (ESI) (M+H)$^+$=349.7.

Example 17

Compound 17, Also 1497

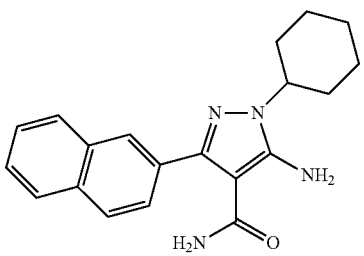

17: 5-amino-1-cyclohexyl-3-(naphthalen-2-yl)-1H-pyrazole-4-carboxamide was synthesized using cyclohexylhydrazine following General Procedure A. $^1$H NMR (500 MHz, CDCl$_3$) δ 8.03 (1H, s), 7.95 (1H, d, J 8.4), 7.93-7.83 (2H, m), 7.64-7.51 (3H, m), 3.91-3.77 (1H, m), 2.08-1.89 (6H, m), 1.73 (1H, m), 1.41 (2H, m), 1.27 (1H, m). MS (ESI) (M+H)$^+$=335.7.

Example 18

Compound 18, Also 1499

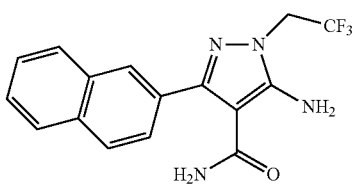

18: 5-amino-3-(naphthalen-2-yl)-1-(2,2,2-trifluoroethyl)-1H-pyrazole-4-carboxamide was synthesized using 2,2,2-trifluoromethylhydrazine following General Procedure A except using different hydrolytic condition. Hydrolysis of cyano group to amide was performed by using 30% $H_2O_2$ (0.2 ml), $NH_4OH$ (0.6 ml) and ethanol (0.6 ml) at room temperature for 5 days. $^1H$ NMR (500 MHz, $CDCl_3$) δ 8.06 (1H, s), 7.95 (1H, d, J 8.3), 7.89 (2H, m), 7.64 (1H, m), 7.60-7.50 (2H, m), 5.57 (4H, broad), 4.62 (2H, m). MS (ESI) $(M+H)^+$=335.7.

Example 19

Compound 19, Also 1502

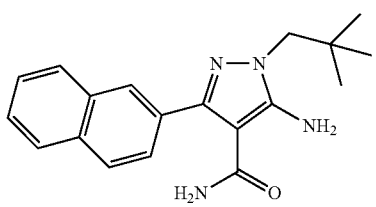

19: 5-amino-3-(naphthalen-2-yl)-1-neopentyl-1H-pyrazole-4-carboxamide was synthesized using neopentylhydrazine following General Procedure A. $^1H$ NMR (500 MHz, $CDCl_3$) δ 8.13 (1H, s), 7.99 (1H, s), 7.92 (2H, s), 7.70-7.64 (1H, m), 7.59 (2H, s), 3.99 (2H, d, J 12.1), 1.14 (9H, s). MS (ESI) $(M+H)^+$=323.8.

Example 20

Compound 20, Also 1498

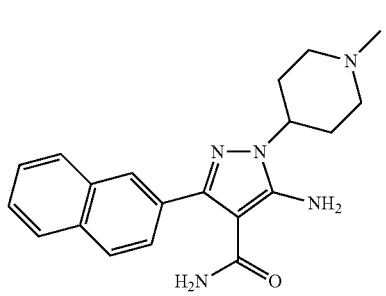

20: 5-amino-1-(1-methylpiperidin-4-yl)-3-(naphthalen-2-yl)-1H-pyrazole-4-carboxamide was synthesized using 1-(1-methylpiperidin-4-yl)hydrazine following General Procedure A. $^1H$ NMR (500 MHz, MeOD) δ 8.04 (1H, s), 7.99 (1H, d, J 8.6), 7.93 (2H, m), 7.60 (1H, dd, J 7.5, 1.5), 7.55 (2H, d, J 8.3), 4.60-4.49 (1H, m), 3.68 (2H, m), 3.27-3.21 (2H, m), 2.94 (3H, s), 2.39 (2H, m), 2.24 (2H, m). MS (ESI) $(M+H)^+$=350.6.

Example 21

Compound 21, Also 1500

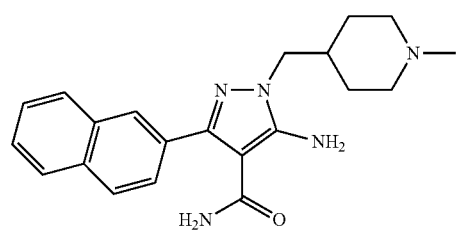

21: 5-amino-1-((1-methylpiperidin-4-yl)methyl)-3-(naphthalen-2-yl)-1H-pyrazole-4-carboxamide was synthesized using 1-methyl-4-(hydrazinylmethyl)piperidine following General Procedure A or General Procedure C by using 1 and 1-methyl-4-methanesulfonyloxymethylpiperidine. $^1H$ NMR (500 MHz, MeOD) δ 8.18 (1H, s), 8.05 (1H, d, J 8.6), 8.00-7.91 (2H, m), 7.65 (1H, d, J 8.9), 7.62-7.54 (2H, m), 4.12 (2H, d, J 7.0), 3.53 (2H, d, J 13.1), 3.02 (2H, t, J 12.0), 2.83 (3H, s), 2.28 (1H, m), 1.97 (2H, d, J 12.1), 1.71 (2H, m). MS (ESI) $(M+H)^+$=364.6.

Example 22

Compound 22, Also 1518

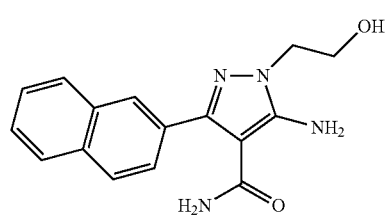

22: 5-amino-1-(2-hydroxyethyl)-3-(naphthalen-2-yl)-1H-pyrazole-4-carboxamide was synthesized using 2-hydrazinylethanol following General Procedure A. $^1H$ NMR (500 MHz, MeOD) δ 8.04 (1H, s), 7.96 (1H, d, J 8.5), 7.93-7.86 (2H, m), 7.60 (1H, m), 7.52 (2H, m), 4.09 (2H, t, J 5.3), 3.88 (2H, t, J 5.2). MS (ESI) $(M+H)^+$=297.5.

Example 23

Compound 23, Also 1519

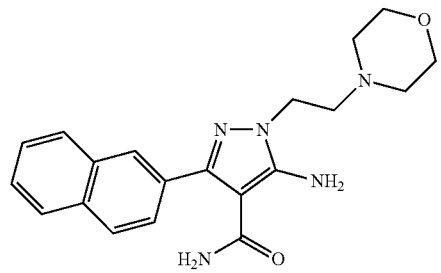

23: 5-amino-1-(2-morpholinoethyl)-3-(naphthalen-2-yl)-1H-pyrazole-4-carboxamide was synthesized using 4-(2-hydrazinoethyl)morpholine following General Procedure A. ¹H NMR (500 MHz, DMSO) δ 8.07 (1H, s), 8.04-7.91 (3H, m), 7.64 (1H, m), 7.56 (2H, dd, J 6.2, 3.3), 4.50 (2H, t, J 6.8), 3.97 (2H, m), 3.80 (2H, m), 3.55 (2H, t, J 6.7), 3.48 (2H, m), 3.17 (2H, m). MS (ESI) (M+H)⁺=366.6.

Example 24

Compound 24, Also 1457

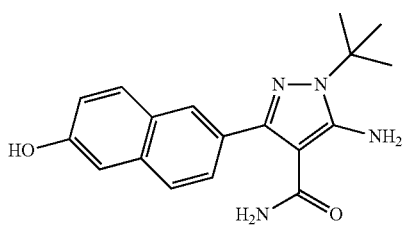

24: 5-amino-1-(tert-butyl)-3-(6-hydroxynaphthalen-2-yl)-1H-pyrazole-4-carboxamide was synthesized using 6-hydroxynaphthalene-2-carbaldehyde following General Procedure B. ¹H NMR (500 MHz, CDCl₃) δ 7.89 (1H, s), 7.71 (2H, d, J 8.1), 7.50 (1H, m), 7.12-7.07 (2H, m), 5.72 (2H, s), 1.71 (28H, s). MS (ESI) (M+H)⁺=325.6.

Example 25

Compound 25, Also 1458

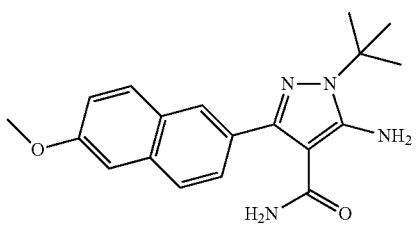

25: 5-amino-1-(tert-butyl)-3-(6-methoxynaphthalen-2-yl)-1H-pyrazole-4-carboxamide was synthesized using 6-methoxynaphthalene-2-carbaldehyde following General Procedure B. ¹H NMR (500 MHz, CDCl₃) δ 7.96 (1H, s), 7.79 (2H, m), 7.60 (1H, m), 7.18 (2H, m), 3.94 (3H, s), 1.69 (9H, s). MS (ESI) (M+H)⁺=340.0.

Example 26

Compound 26, Also 1474

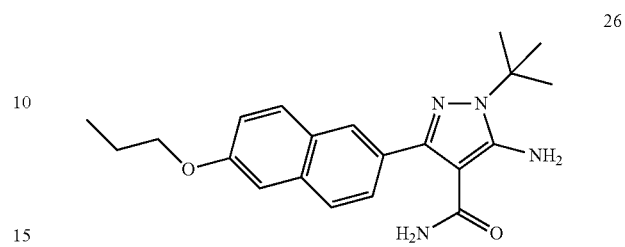

26: 5-amino-1-(tert-butyl)-3-(6-propoxynaphthalen-2-yl)-1H-pyrazole-4-carboxamide To a solution of 24 (20 mg) in DMF (0.5 ml) was added K₂CO₃ (20 equiv), 1-bromopropane (20 equiv). The mixture was microwave irradiated at 75° C. for 40 min. After cooling down to room temperature, ethyl acetate was added and the organic layer was washed with water, brine, dried over Na₂SO₄ and concentrated under reduced pressure. Purification via preparative HPLC gave the HPLC pure final product. ¹H NMR (500 MHz, CDCl₃) δ 7.97 (1H, s), 7.80 (2H, d, J 13.3), 7.57 (1H, s), 7.20 (1H, d, J 7.2), 7.15 (1H, s), 4.05 (2H, t, J 6.3), 1.88 (2H, m), 1.78 (9H, s), 1.09 (3H, t, J 7.4). MS (ESI) (M+H)⁺=367.6.

Example 27

Compound 27, Also 1480

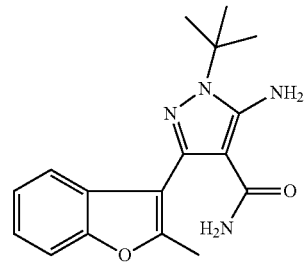

27: 5-amino-1-(tert-butyl)-3-(2-methylbenzofuran-3-yl)-1H-pyrazole-4-carboxamide was synthesized using 2-methylbenzofuran-3-carbaldehyde following General Procedure B. ¹H NMR (500 MHz, CDCl₃) δ 7.46 (1H, d, J 8.1), 7.40 (1H, d, J 7.3), 7.28 (1H, t, J 7.1), 7.23 (1H, t, J 7.0), 2.50 (3H, s), 1.70 (9H, s). MS (ESI) (M+H)⁺=313.7.

Examples 28 and 29

Compound 28 (Also 1459) and 29 (Also 1460)

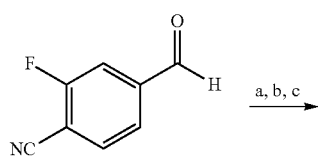

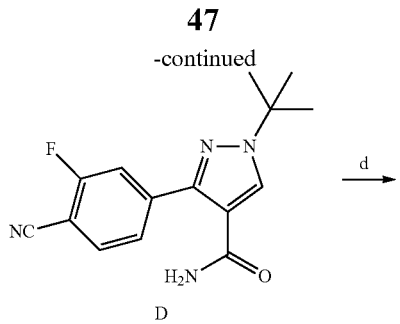

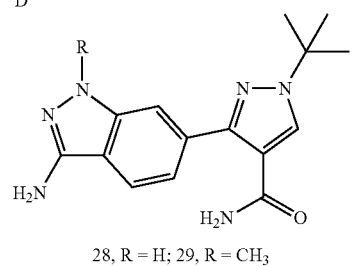

28, R = H; 29, R = CH₃

Reagents and conditions
(a) t-butylhydrazine, DMF;
(b) NBS, DMF, 0° C.;
(c) EtONa, cyanoacetamide, EtOH;
(d) R—NHNH₂, EtOH, heating.

General Procedure D (28, 29)

Intermediate D was synthesized using 2-fluoro-4-formyl-benzonitrile following General Procedure B. H¹NMR (500 MHz, MeOD) δ 7.81 (1H, t, J 7.3), 7.59 (2H, t, J 9.7), 1.67 (9H, s). MS (ESI) (M+H)⁺=302.7.

A solution of D (20 mg) in ethanol (0.5 ml) and hydrazine monohydrate or methylhydrazine (60 μl) was microwave irradiated at 120° C. for 40 min. After cooling down to room temperature, ethyl acetate was added and the organic layer was washed with water three times, brine, dried over Na₂SO₄ and concentrated under reduced pressure. Purification via preparative HPLC gave the HPLC pure final product.

28: 3-(3-amino-1H-indazol-6-yl)-1-(tert-butyl)-1H-pyrazole-4-carboxamide was synthesized using hydrazine monohydrate following General Procedure D. ¹H NMR (500 MHz, DMSO) δ 7.72 (1H, d, J 8.2), 7.26 (1H, s), 6.98 (1H, d, J 8.2), 6.29 (2H, s), 5.39 (2H, s), 1.55 (9H, s). MS (ESI) (M+H)⁺=314.6.

29: 3-(3-amino-1-methyl-1H-indazol-6-yl)-1-(tert-butyl)-1H-pyrazole-4-carboxamide was synthesized using methylhydrazine following General Procedure D. ¹H NMR (500 MHz, DMSO) δ 7.71 (1H, d, J 8.2), 7.36 (1H, s), 6.94 (1H, d, J 8.2), 6.32 (2H, s), 5.46 (2H, s), 3.72 (3H, s), 1.56 (9H, s). MS (ESI) (M+H)⁺=328.6.

Example 30

Compound 30, Also 1472

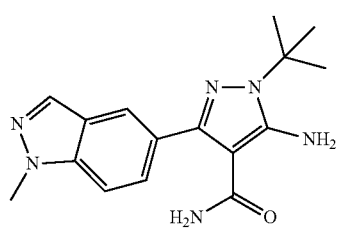

30: 5-amino-1-(tert-butyl)-3-(1-methyl-1H-indazol-5-yl)-1H-pyrazole-4-carboxamide was synthesized using 1-methyl-1H-indazole-5-carbaldehyde following General Procedure B. B. ¹H NMR (500 MHz, DMSO) δ8.72 (1H, s), 7.57 (1H, d, J 8.3), 7.45 (1H, s), 7.39 (1H, d, J 6.9), 3.65 (3H, s), 1.58 (9H, s). MS (ESI) (M+H)⁺=313.8.

Example 31

Compound 31, Also 1482

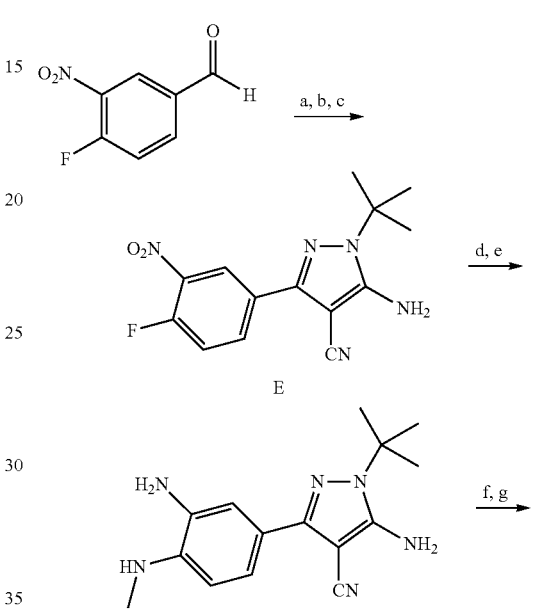

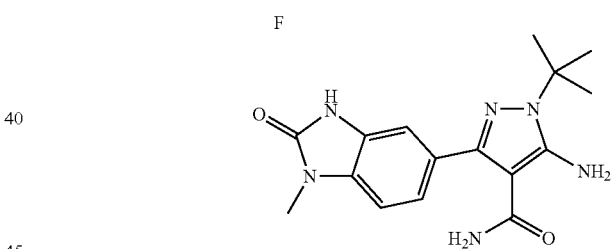

Reagents and conditions
(a) t-butylhydrazine, DMF;
(b) NBS, DMF, 0° C.;
(c) EtONa, malononitrile, EtOH;
(d) CH₃NH₂;
(e) Zn, HCONH₂;
(f) CDI, microwave, 70° C., 30 min;
(g) NaOH, EtOH, microwave, 110° C., 10 min.

Intermediate E was synthesized using 3-nitro-4-fluorobenzaldehyde following General Procedure B except using malononitrile instead of cyanoacetamide. ¹H NMR (500 MHz, CDCl₃) δ 8.59 (1H, m), 8.21-8.13 (1H, m), 7.37-7.27 (1H, m), 1.69 (9H, s). MS (ESI) (M+H)⁺=304.8.

Intermediate F: A solution of E (160 mg, 0.53 mmol) in ethanol (1.0 ml) and methylamine (4 ml, 33% wt in EtOH) was stirred at room temperature for 30 min. After solvents were removed, the residue was diluted with ethyl acetate. The organic extract was washed with water, brine, dried over Na₂SO₄ and concentrated under reduced pressure. The residue was dissolved in 5 ml of methanol. To the solution, ammonium formate (5 equiv) was added with stirring, then powder Zn (5 equiv) was added slowly with strong stirring. After 10 min, the solvent was removed and 20 ml of ethyl acetate was added. The organic extract was purified via flash chromatography on silica gel to obtain 96 mg of F in brownish solid. $^1$H NMR (500 MHz, MeOD) δ 7.32-7.18 (2H, m), 6.60 (1H, d, J 8.2), 2.86 (3H, s), 1.64 (9H, s). MS (ESI) (M+H)$^+$=285.6.

31: 5-amino-1-(tert-butyl)-3-(1-methyl-2-oxo-2,3-dihydro-1H-benzo[d]imidazol-5-yl)-1H-pyrazole-4-carboxamide. A solution of F (12 mg) in anhydrous THF (1.0 ml) was added 1,1'-carbonyldiimidazole (2.5 equiv). The mixture was microwave irradiated at 70° C. for 30 min. After cooling down to room temperature, ethyl acetate was added and the organic layer was washed with water, brine, dried over Na$_2$SO$_4$ and concentrated under reduced pressure. The residue was dissolved in 1 ml of ethanol, 0.2 ml of saturated aqueous NaOH was added and the solution was microwave irradiated at 110° C. for 20 min. After cooling down to 0° C., concentrated HCl was added slowly to neutralize the solution. The solution was extracted with ethyl acetate, washed with water twice. The solvent was removed and the residue was dissolved in methanol and purified by preparative HPLC with an acetonitrile/water gradient with 0.1% TFA to yield the final product. $^1$H NMR (500 MHz, DMSO) δ 10.94 (1H, s), 7.15 (2H, m), 7.05 (1H, s), 2.53 (3H, s), 1.59 (9H, s). MS (ESI) (M+H)$^+$=329.5.

Example 32

Example 32, Also 1487

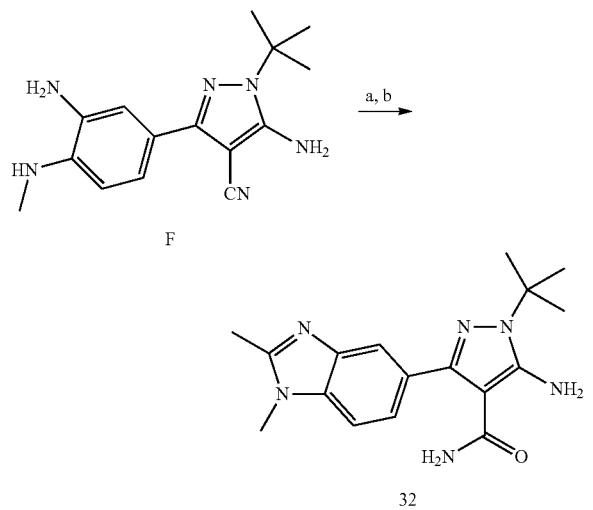

Reagents and conditions
(a) acetaldehyde, NaHSO$_3$, microwave, 70° C., 15 min;
(b) NaOH, EtOH, microwave, 110° C., 10 min.

32: 5-amino-1-(tert-butyl)-3-(1,2-dimethyl-1H-benzo[d]imidazol-5-yl)-1H-pyrazole-4-carboxamide. To a solution of F (12 mg) in THF (1.0 ml) was added acetaldehyde (6 equiv) and sodium bisulfite (6 equiv). The mixture was microwave irradiated at 70° C. for 15 min. After cooling down to room temperature, ethyl acetate was added and the organic layer was washed with brine, dried over Na$_2$SO$_4$ and concentrated under reduced pressure. The residue was dissolved in 1 ml of ethanol, 0.2 ml of saturated aqueous NaOH was added and the solution was microwave irradiated at 110° C. for 20 min. After cooling down to 0° C., concentrated HCl was added slowly to neutralize the solution. The solution was extracted with ethyl acetate, washed with water twice. The solvent was removed and the residue was dissolved in methanol and purified by preparative HPLC with an acetonitrile/water gradient with 0.1% TFA to yield the final product. H$^1$NMR (500 MHz, CDCl$_3$) δ 8.22 (1H, s), 7.81 (1H, dd, J 8.4, 1.5), 7.27 (1H, d, J 8.4), 4.45 (2H, s), 3.71 (3H, s), 2.61 (3H, s), 1.67 (9H, s). MS (ESI) (M+H)$^+$=327.7.

Example 33

Compound 33, Also 1488

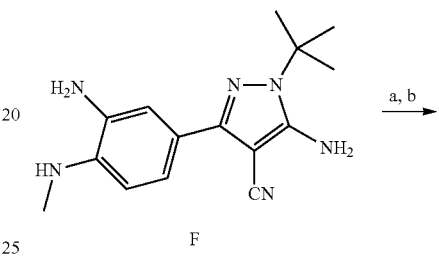

Reagents and conditions
(a) EtOH, BrCN;
(b) NaOH, EtOH, microwave, 110° C., 10 min.

33: 5-amino-3-(2-amino-1-methyl-1H-benzo[d]imidazol-5-yl)-1-(tert-butyl)-1H-pyrazole-4-carboxamide. To a solution of F (12 mg) in anhydrous ethanol (0.5 ml) was added BrCN (2.5 equiv). The mixture was stirred at room temperature overnight. Ethyl acetate was added and washed with saturated NaHCO$_3$, brine, dried over Na$_2$SO$_4$ and concentrated under reduced pressure. The residue was dissolved in 1 ml of ethanol, 0.2 ml of saturated aqueous NaOH was added and the solution was microwave irradiated at 110° C. for 20 min. After cooling down to 0° C., concentrated HCl was added slowly to neutralize the solution. The solution was extracted with ethyl acetate, washed with water twice. The solvent was removed and the residue was dissolved in methanol and purified by preparative HPLC with an acetonitrile/water gradient with 0.1% TFA to yield the final product. H$^1$NMR (500 MHz, MeOD) δ 7.67-7.60 (2H, m), 7.55 (1H, d, J 7.2), 3.72 (3H, s), 3.32 (2H, s), 1.72 (9H, s). MS (ESI) (M+H)$^+$=328.6.

Example 34

Compound 34, Also 1489

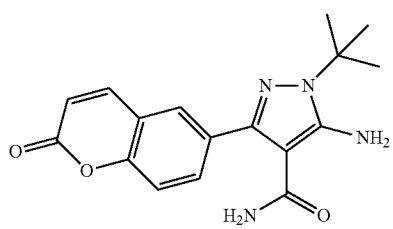

34: 5-amino-1-(tert-butyl)-3-(2-oxo-2H-chromen-6-yl)-1H-pyrazole-4-carboxamide was synthesized using coumarin-6-carbaldehyde following General Procedure B. $^1$H NMR (500 MHz, CDCl$_3$) δ 7.73 (3H, m), 7.41 (1H, d, J 8.5), 6.48 (1H, d, J 9.5), 5.70 (2H, s), 5.13 (2H, s), 1.68 (9H, s). MS (ESI) (M+H)$^+$=327.7.

Example 35

Compound 35, Also 1455

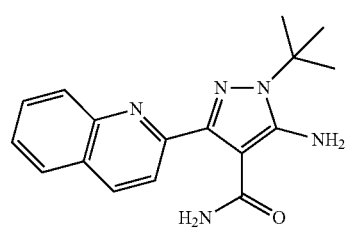

35: 5-amino-1-(tert-butyl)-3-(quinolin-2-yl)-1H-pyrazole-4-carboxamide was synthesized using quinoline-2-carbaldehyde following General Procedure B. $^1$H NMR (500 MHz, CDCl$_3$) δ 8.39 (1H, d, J 8.8), 8.17 (1H, d, J 8.9), 7.95 (1H, d, J 8.4), 7.82 (1H, d, J 6.9), 7.74-7.66 (1H, m), 7.57-7.50 (1H, m), 6.08 (2H, s), 1.73 (9H, s). MS (ESI) (M+H)$^+$=310.6.

Example 36

Compound 36, Also 1481

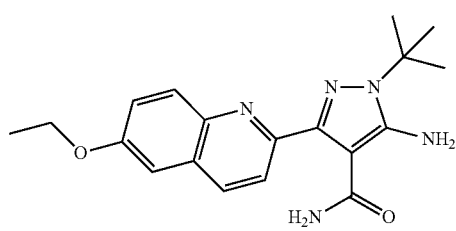

36: 5-amino-1-(tert-butyl)-3-(6-ethoxyquinolin-2-yl)-1H-pyrazole-4-carboxamide was synthesized using 6-ethoxyquinoline-2-carbaldehyde following General Procedure B. $^1$H NMR (500 MHz, CDCl$_3$) δ 8.33 (1H, d, J 8.8), 8.05 (1H, d, J 8.9), 7.84 (1H, d, J 9.1), 7.34 (1H, dd, J 9.1, 2.7), 7.08 (1H, d, J 2.7), 6.04 (2H, s), 4.17 (2H, m), 1.72 (9H, s), 1.50 (3H, t, J 7.0). MS (ESI) (M+H)$^+$=354.6.

Example 37

Compound 37, Also 1471

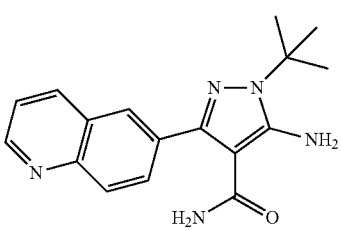

37: 5-amino-1-(tert-butyl)-3-(quinolin-6-yl)-1H-pyrazole-4-carboxamide was synthesized using quinoline-6-carbaldehyde following General Procedure B. $^1$H NMR (500 MHz, CDCl$_3$) δ 8.95 (1H, d, J 4.5), 8.18 (2H, m), 8.05 (1H, s), 7.91 (1H, d, J 5.6), 7.50-7.40 (1H, m), 5.73 (2H, s), 1.68 (9H, s). MS (ESI) (M+H)$^+$=310.8.

Example 38

Compound 38, Also 1456

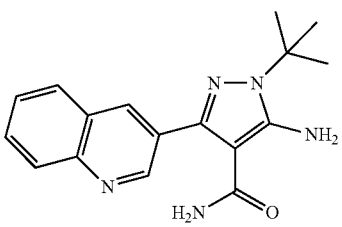

38: 5-amino-1-(tert-butyl)-3-(quinolin-3-yl)-1H-pyrazole-4-carboxamide was synthesized using quinoline-3-carbaldehyde prepared according to the literature procedure following General Procedure B. $^1$H NMR (500 MHz, DMSO) δ 9.01 (1H, s), 8.44 (1H, s), 8.06 (2H, d, J 9.0), 7.84-7.74 (1H, m), 7.68-7.60 (1H, m), 6.23 (2H, s), 1.61 (9H, s). MS (ESI) (M+H)$^+$=310.7.

Example 39

Compound 39, Also 1517

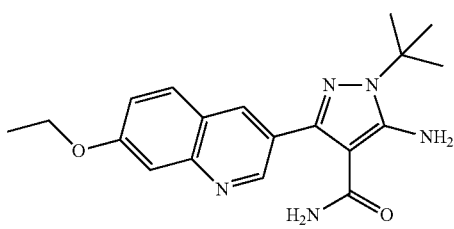

39: 5-amino-1-(tert-butyl)-3-(7-ethoxyquinolin-3-yl)-1H-pyrazole-4-carboxamide was synthesized using 7-ethoxyquinoline-3-carbaldehyde prepared according to the literature procedure following General Procedure B. $^1$H NMR (500 MHz, CDCl$_3$) δ 9.19 (1H, s), 8.84 (1H, s), 7.98 (1H, d, J 13.2), 7.77 (1H, s), 7.47 (1H, d, J 10.5), 6.10 (2H, s), 4.28 (2H, m), 1.68 (9H, s), 1.53 (3H, t, J 6.9). MS (ESI) (M+H)$^+$=354.5.

Example 40

Compound 1572

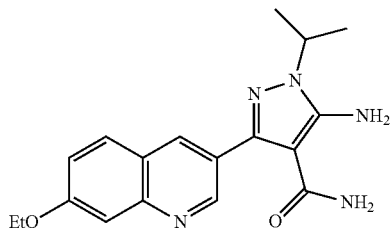 [SMILES: CCOc1ccc2cc(-c3nn(C(C)C)c(N)c3C(N)=O)cnc2c1]

1572: 5-amino-3-(7-ethoxyquinolin-3-yl)-1-isopropyl-1H-pyrazole-4-carboxamide. $^1$H NMR (500 MHz, CDCl$_3$) δ 9.08 (s, 1H), 8.44 (s, 1H), 7.81 (d, J=9.0 Hz, 1H), 7.53 (s, 1H), 7.31 (d, J=9.0 Hz, 1H), 5.45 (s, 2H), 5.21 (s, 2H), 4.39-4.30 (m, 1H), 4.26 (q, J=6.9 Hz, 2H), 1.64-1.49 (m, 9H); MS (ESI) (M+H)$^+$=340.5; HPLC analysis: 97.9% purity.

Example 41

Compound 1573

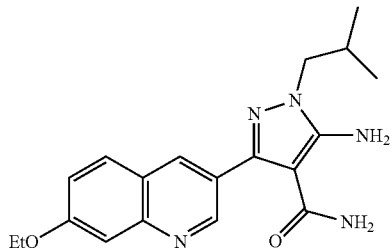 [SMILES: CCOc1ccc2cc(-c3nn(CC(C)C)c(N)c3C(N)=O)cnc2c1]

1573: 5-amino-3-(7-ethoxyquinolin-3-yl)-1-isobutyl-1H-pyrazole-4-carboxamide. $^1$H NMR (500 MHz, CDCl$_3$) δ 9.05 (s, 1H), 8.37 (s, 1H), 7.79 (d, J=8.8 Hz, 1H), 7.53 (s, 1H), 7.30 (d, J=8.8 Hz, 1H), 4.25 (q, J=6.8 Hz, 2H), 3.78 (d, J=7.4 Hz, 2H), 2.39-2.25 (m, 1H), 1.54 (t, J=6.9 Hz, 3H), 1.03 (d, J=6.6 Hz, 6H); MS (ESI) (M+H)$^+$=354.6; HPLC analysis: 96.9% purity.

Example 42

Compound 1591

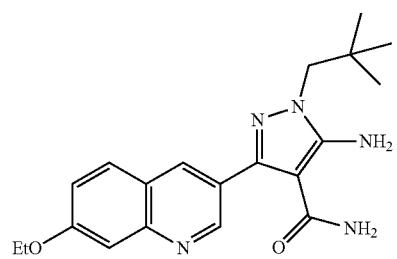 [SMILES: CCOc1ccc2cc(-c3nn(CC(C)(C)C)c(N)c3C(N)=O)cnc2c1]

1591: 5-amino-3-(7-ethoxyquinolin-3-yl)-1-neopentyl-1H-pyrazole-4-carboxamide. $^1$H NMR (300 MHz, CDCl$_3$) δ 9.06 (d, J=2.4 Hz, 1H), 8.39 (s, 1H), 7.80 (d, J=9.0 Hz, 1H), 7.57 (s, 1H), 7.31 (dd, J$_1$=9.0, 2.4 Hz, 1H), 5.48 (s, 2H), 5.21 (s, 2H), 4.25 (q, J=7.0 Hz, 2H), 3.77 (s, 2H), 1.54 (t, J=7.0 Hz, 3H), 1.10 (s, 9H); MS (ESI) (M+H)$^+$=368.6; HPLC analysis: 95.0% purity.

Example 43

Compound 1575

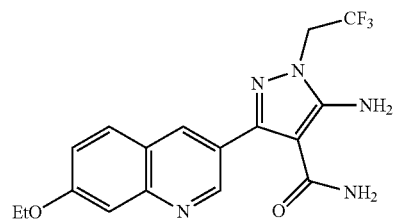 [SMILES: CCOc1ccc2cc(-c3nn(CC(F)(F)F)c(N)c3C(N)=O)cnc2c1]

1575: 5-amino-3-(7-ethoxyquinolin-3-yl)-1-(2,2,2-trifluoroethyl)-1H-pyrazole-4-carboxamide. $^1$H NMR (500 MHz, CDCl$_3$) δ 9.03 (s, 1H), 8.32 (s, 1H), 7.78 (d, J=9.0 Hz, 1H), 7.47 (s, 1H), 7.29 (dd, J=9.0, 2.2 Hz, 1H), 5.65 (s, 2H), 5.23 (s, 2H), 4.65 (t, J=6.9 Hz, 2H), 4.24 (q, J=6.9 Hz, 2H), 1.54 (t, J=6.9 Hz, 3H); MS (ESI) (M+H)$^+$=380.5; HPLC analysis: 96.8% purity.

Example 44

Compound 1598

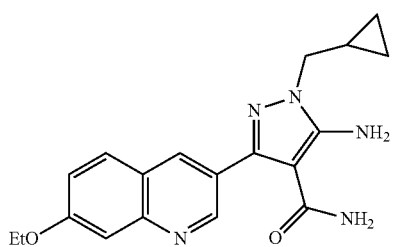 [SMILES: CCOc1ccc2cc(-c3nn(CC4CC4)c(N)c3C(N)=O)cnc2c1]

1598: 5-amino-1-(cyclopropylmethyl)-3-(7-ethoxyquinolin-3-yl)-1H-pyrazole-4-carboxamide. $^1$H NMR (500 MHz, CDCl$_3$) δ 9.06 (s, 1H), 8.37 (s, 1H), 7.79 (d, J=9.0 Hz, 1H), 7.52 (s, 1H), 7.30 (dd, J=9.0, 2.3 Hz, 1H), 5.50 (s, 2H), 5.24 (s, 2H), 4.24 (q, J=6.9 Hz, 2H), 3.93 (d, J=6.6 Hz, 2H), 1.53 (t, J=7.0 Hz, 3H), 1.31 (m, 1H), 0.69 (m, 2H), 0.46 (m, 2H); MS (ESI) (M+H)$^+$=352.6; HPLC analysis: 99.0% purity.

Example 45

Compound 1652

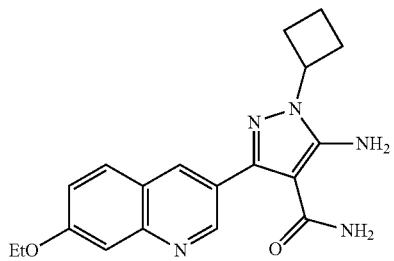 [SMILES: CCOc1ccc2cc(-c3nn(C4CCC4)c(N)c3C(N)=O)cnc2c1]

1652: 1-isobutyl-3-(2-(2,2,2-trifluoroethoxy)quinolin-6-yl)-1H-pyrazolo[3,4-d]pyrimidin-4-amine. $^1$H NMR (500 MHz, MeOD) δ 9.32 (s, 1H), 9.27 (s, 1H), 8.29 (d, J=8.5 Hz, 1H), 7.61 (d, J=8.5 Hz, 1H), 7.54 (s, 1H), 4.38 (q, J=6.2 Hz, 2H), 2.71 (m, 2H), 2.46 (m, 2H), 1.92 (m, 2H), 1.56 (t, J=6.2 Hz, 3H); MS (ESI) (M+H)$^+$=352.4; HPLC analysis: 98.7% purity.

Example 46

Compound 1605

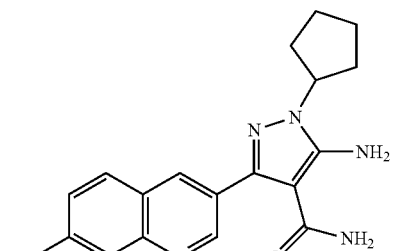

1605: 5-amino-1-cyclopentyl-3-(7-ethoxyquinolin-3-yl)-1H-pyrazole-4-carboxamide. $^1$H NMR (500 MHz, MeOD) δ 9.28 (s, 1H), 9.24 (s, 1H), 8.29 (d, J=9.2 Hz, 1H), 7.61 (dd, J=9.2, 2.1 Hz, 1H), 7.51 (s, 1H), 4.76-4.64 (m, 1H), 4.45-4.32 (q, J=7.0 Hz, 2H), 2.23-2.06 (m, 4H), 2.03-1.90 (m, 2H), 1.85-1.70 (m, 2H), 1.57 (t, J=7.0 Hz, 3H); MS (ESI) (M+H)$^+$=366.3; HPLC analysis: 95.0% purity.

Example 47

Compound 1571

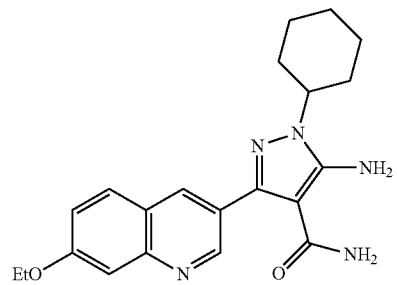 [SMILES: CCOc1ccc2cc(-c3nn(C4CCCCC4)c(N)c3C(N)=O)cnc2c1]

1571: 5-amino-1-cyclohexyl-3-(7-ethoxyquinolin-3-yl)-1H-pyrazole-4-carboxamide. $^1$H NMR (500 MHz, CDCl$_3$) δ 9.05 (s, 1H), 8.35 (s, 1H), 7.78 (d, J=9.0 Hz, 1H), 7.52 (s, 1H), 7.28 (dd, J=9.0, 2.3 Hz, 1H), 5.47 (s, 2H), 5.20 (s, 2H), 4.24 (q, J=6.9 Hz, 2H), 3.96-3.82 (m, 1H), 2.10-1.92 (m, 6H), 1.53 (t, J=6.9 Hz, 3H), 1.49-1.38 (m, 2H), 1.37-1.23 (m, 2H); MS (ESI) (M+H)$^+$=380.5; HPLC analysis: 96.8% purity.

Example 48

Compound 1606

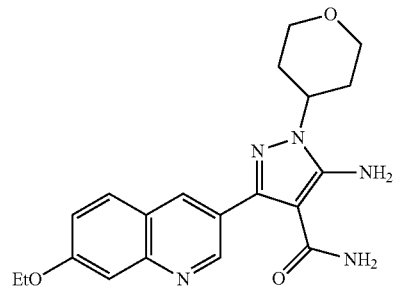 [SMILES: CCOc1ccc2cc(-c3nn(C4CCOCC4)c(N)c3C(N)=O)cnc2c1]

1606: 5-amino-3-(7-ethoxyquinolin-3-yl)-1-(tetrahydro-2H-pyran-4-yl)-1H-pyrazole-4-carboxamide. $^1$H NMR (500 MHz, DMSO) δ 9.21 (s, 1H), 9.06 (s, 1H), 8.30 (d, J=9.1 Hz, 1H), 7.65 (s, 1H), 7.56 (dd, J=9.1, 1.9 Hz, 1H), 4.51-4.43 (m, 1H), 4.29 (q, J=6.9 Hz, 2H), 4.03-3.96 (m, 2H), 2.10-1.97 (m, 2H), 1.86-1.78 (m, 2H), 1.46 (t, J=6.8 Hz, 3H); MS (ESI) (M+H)$^+$=382.4; HPLC analysis: 99.5% purity.

Example 49

Compound 1604

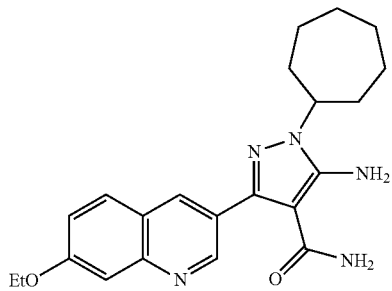 [SMILES: CCOc1ccc2cc(-c3nn(C4CCCCCC4)c(N)c3C(N)=O)cnc2c1]

1604: 5-amino-1-cycloheptyl-3-(7-ethoxyquinolin-3-yl)-1H-pyrazole-4-carboxamide. $^1$H NMR (500 MHz, CDCl$_3$) δ 9.03 (s, 1H), 8.31 (s, 1H), 7.76 (d, J=8.9 Hz, 1H), 7.48 (s, 1H), 7.26 (dd, J=8.9, 1.8 Hz, 1H), 5.47 (s, 2H), 5.23 (s, 2H), 4.23 (q, J=6.9 Hz, 2H), 4.14-4.02 (m, 1H), 2.21-2.03 (m, 4H), 1.94-1.83 (m, 2H), 1.74-1.61 (m, 4H), 1.60-1.48 (m, 5H); MS (ESI) (M+H)$^+$=394.6; HPLC analysis: 99.3% purity.

Example 50

Compound 1574

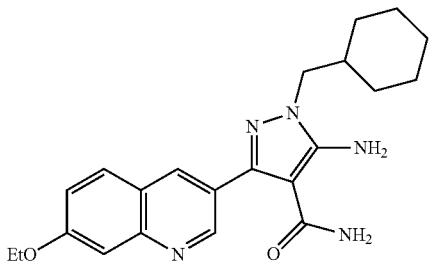 [SMILES: CCOc1ccc2cc(-c3nn(CC4CCCCC4)c(N)c3C(N)=O)cnc2c1]

1574: 5-amino-1-(cyclohexylmethyl)-3-(7-ethoxyquinolin-3-yl)-1H-pyrazole-4-carboxamide. $^1$H NMR (500 MHz, CDCl$_3$) δ 9.04 (s, 1H), 8.31 (d, J=1.8 Hz, 1H), 7.77 (d, J=9.0 Hz, 1H), 7.47 (d, J=2.0 Hz, 1H), 7.26 (dd, J=9.0, 2.0 Hz, 1H), 5.44 (s, 2H), 5.18 (s, 2H), 4.24 (q, J=7.0 Hz, 2H), 3.80 (d, J=7.3 Hz, 2H), 2.06-1.94 (m, 1H), 1.82-1.67 (m, 6H), 1.53 (t, J=7.0 Hz, 3H), 1.32-1.24 (m, 2H), 1.014-1.01 (m, 2H); MS (ESI) (M+H)$^+$=394.6; HPLC analysis: 97.2% purity.

Example 51

Compound 1627

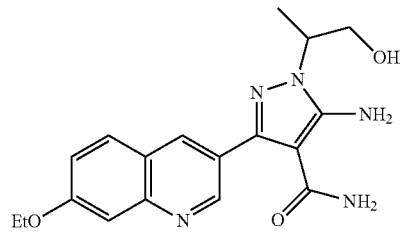 [SMILES: CCOc1ccc2cc(-c3nn(C(C)CO)c(N)c3C(N)=O)cnc2c1]

1627: 5-amino-3-(7-ethoxyquinolin-3-yl)-1-(1-hydroxypropan-2-yl)-1H-pyrazole-4-carboxamide. $^1$H NMR (500 MHz, MeOD) δ 9.31 (s, 1H), 9.26 (s, 1H), 8.29 (d, J=9.1 Hz, 1H), 7.62 (d, J=9.1 Hz, 1H), 7.54 (s, 1H), 4.55-4.44 (m, 1H), 4.38 (q, 6.9 Hz, 2H), 3.98-3.89 (m, 1H), 3.88-3.80 (m, 1H), 1.57 (t, J=6.9 Hz, 3H), 1.47 (d, J=6.8 Hz, 3H); MS (ESI) (M+H)$^+$=356.5; HPLC analysis: 99.0% purity.

Example 52

Compound 1641

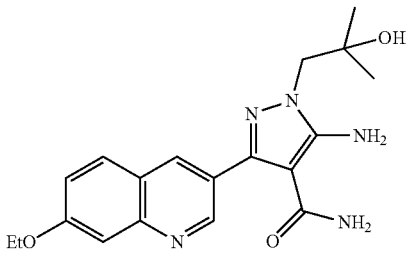 [SMILES: CCOc1ccc2cc(-c3nn(CC(C)(C)O)c(N)c3C(N)=O)cnc2c1]

1641: 5-amino-3-(7-ethoxyquinolin-3-yl)-1-(2-hydroxy-2-methylpropyl)-1H-pyrazole-4-carboxamide. $^1$H NMR (500 MHz, MeOD) δ 9.30 (s, 1H), 9.25 (s, 1H), 8.29 (d, J=8.9 Hz, 1H), 7.61 (d, J=8.9 Hz, 1H), 7.52 (s, 1H), 4.37 (q, J=6.8 Hz, 2H), 4.06 (s, 2H), 1.56 (t, J=6.8 Hz, 3H), 1.31 (s, 6H); MS (ESI) (M+H)$^+$=370.6; HPLC analysis: 95.0% purity.

Example 53

Compound 1608

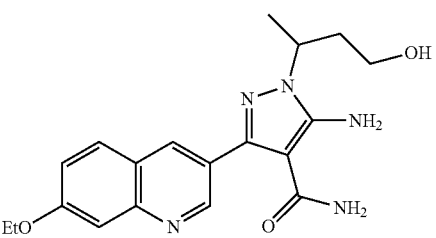 [SMILES: CCOc1ccc2cc(-c3nn(C(C)CCO)c(N)c3C(N)=O)cnc2c1]

1608: 5-amino-3-(7-ethoxyquinolin-3-yl)-1-(4-hydroxybutan-2-yl)-1H-pyrazole-4-carboxamide. $^1$H NMR (500 MHz, DMSO) δ 9.20 (d, J=1.8 Hz, 1H), 9.04 (s, 1H), 8.29 (d, J=9.1 Hz, 1H), 7.62 (s, 1H), 7.55 (dd, J=9.1, 1.8 Hz, 1H), 6.67 (s, 2H), 4.56-4.50 (m, 1H), 4.29 (q, 6.9 Hz, 2H), 2.12-1.99 (m, 2H), 1.94-1.80 (m, 2H), 1.45 (t, J=6.9 Hz, 3H), 1.38 (d, J=6.5 Hz, 3H); MS (ESI) (M+H)⁺=370.5; HPLC analysis: 97.3% purity.

Example 54

Compound 1596

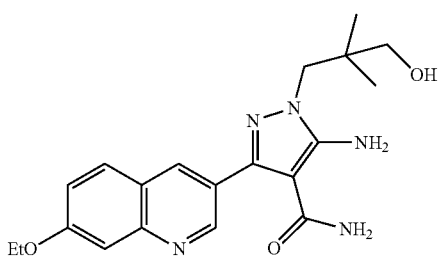 [SMILES: CCOc1ccc2cc(-c3nn(CC(C)(C)CO)c(N)c3C(N)=O)cnc2c1]

1596: 5-amino-3-(7-ethoxyquinolin-3-yl)-1-(3-hydroxy-2,2-dimethylpropyl)-1H-pyrazole-4-carboxamide. ¹H NMR (500 MHz, CDCl₃) δ 9.10 (s, 1H), 8.56 (d, J=9.7 Hz, 1H), 7.87 (s, 1H), 7.71 (s, 1H), 7.36 (d, J=9.7 Hz, 1H), 6.04 (s, 2H), 5.36 (s, 2H), 4.27 (q, J=6.9 Hz, 2H), 3.89 (s, 2H), 3.33 (s, 2H), 1.54 (t, J=6.9 Hz, 3H), 1.07 (s, 6H); MS (ESI) (M+H)⁺=384.6; HPLC analysis: 98.7% purity.

Example 55

Compound 1597

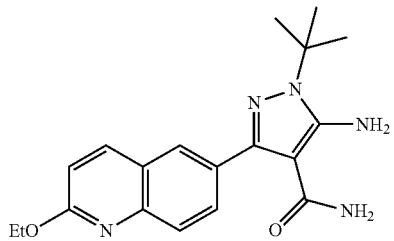 [SMILES: CCOc1ccc2cc(-c3nn(C(C)(C)C)c(N)c3C(N)=O)ccc2n1]

1597: 5-amino-1-(tert-butyl)-3-(2-ethoxyquinolin-6-yl)-1H-pyrazole-4-carboxamide. ¹H NMR (500 MHz, CDCl₃) δ 8.05 (d, J=8.4 Hz, 1H), 8.01 (d, J=8.8 Hz, 1H), 7.94 (s, 1H), 7.82 (d, J=8.4 Hz, 1H), 6.97 (d, J=8.8 Hz, 1H), 5.42 (s, 2H), 4.61 (q, J=6.9 Hz, 2H), 1.72 (s, 6H), 1.50 (t, J=6.9 Hz, 3H); MS (ESI) (M+H)⁺=354.7; HPLC analysis: 95.4% purity.

Example 56

Compound 1635

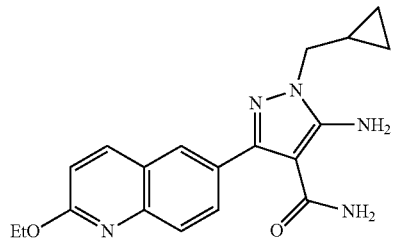 [SMILES: CCOc1ccc2cc(-c3nn(CC4CC4)c(N)c3C(N)=O)ccc2n1]

1635: 5-amino-1-(cyclopropylmethyl)-3-(2-ethoxyquinolin-6-yl)-1H-pyrazole-4-carboxamide. ¹H NMR (500 MHz, MeOD) δ 8.67 (d, J=8.9 Hz, 1H), 8.26 (s, 1H), 8.05 (d, J=8.4 Hz, 1H), 7.99 (d, J=8.4 Hz, 1H), 7.43 (d, J=8.9 Hz, 1H), 3.98 (d, J=6.8 Hz, 2H), 1.56 (t, J=6.9 Hz, 3H), 1.42-1.36 (m, 1H), 0.68-0.60 (m, 2H), 0.54-0.44 (m, 2H); MS (ESI) (M+H)⁺=352.6; HPLC analysis: 95.0% purity.

Example 57

Compound 1633

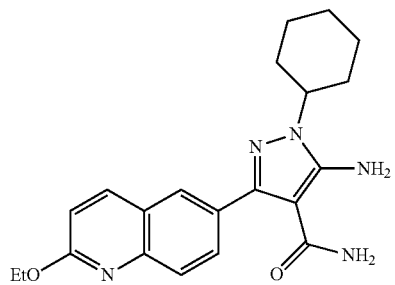 [SMILES: CCOc1ccc2cc(-c3nn(C4CCCCC4)c(N)c3C(N)=O)ccc2n1]

1633: 5-amino-1-cyclohexyl-3-(2-ethoxyquinolin-6-yl)-1H-pyrazole-4-carboxamide. ¹H NMR (500 MHz, MeOD) δ 8.88 (d, J=9.1 Hz, 1H), 8.38 (s, 1H), 8.15 (d, J=8.5 Hz, 1H), 8.04 (d, J=8.5 Hz, 1H), 7.63 (d, J=9.1 Hz, 1H), 4.76 (q, J=7.0 Hz, 4H), 4.36-4.28 (m, 1H), 2.08-2.01 (m, 2H), 2.01-1.94 (m, 2H), 1.93-1.85 (m, 2H), 1.83-1.74 (m, 2H), 1.55 (q, J=7.0 Hz, 3H), 1.39-1.24 (m, 2H); MS (ESI) (M+H)⁺=380.6; HPLC analysis: 97.1% purity.

Example 58

Compound 1632

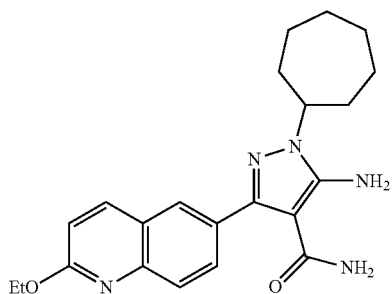 [SMILES: CCOc1ccc2cc(-c3nn(C4CCCCCC4)c(N)c3C(N)=O)ccc2n1]

1632: 5-amino-1-cycloheptyl-3-(2-ethoxyquinolin-6-yl)-1H-pyrazole-4-carboxamide. $^1$H NMR (500 MHz, MeOD) δ 8.31 (d, J=9.0 Hz, 1H), 8.04 (d, J=1.8 Hz, 1H), 7.93 (d, J=8.6 Hz, 1H), 7.85 (dd, J=8.6, 1.8 Hz, 1H), 7.11 (d, J=9.0 Hz, 1H), 4.58 (q, J=7.1 Hz, 2H), 4.41-4.26 (m, 1H), 2.17-1.96 (m, 6H), 1.95-1.81 (m, 2H), 1.81-1.71 (m, 2H), 1.69-1.59 (m, 4H), 1.49 (t, J=7.1 Hz, 3H); MS (ESI) (M+H)$^+$=394.6; HPLC analysis: 96.2% purity.

Example 59

Compound 1622

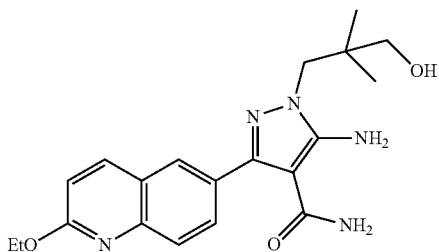 [SMILES: CCOc1ccc2cc(-c3nn(CC(C)(C)CO)c(N)c3C(N)=O)ccc2n1]

1622: 5-amino-3-(2-ethoxyquinolin-6-yl)-1-(3-hydroxy-2,2-dimethylpropyl)-1H-pyrazole-4-carboxamide. $^1$H NMR (500 MHz, CDCl$_3$) δ 8.01 (d, J=8.8 Hz, 1H), 7.95-7.88 (m, 2H), 7.78 (d, J=8.5 Hz, 1H), 6.95 (d, J=8.8 Hz, 1H), 6.29-5.67 (br, 2H), 5.31 (s, 2H), 4.57 (q, J=7.0 Hz, 2H), 3.86 (s, 2H), 3.33 (s, 2H), 1.48 (t, J=7.0 Hz, 3H), 1.04 (s, 6H); MS (ESI) (M+H)$^+$=384.6; HPLC analysis: 96.3% purity.

Example 60

Compound 1545

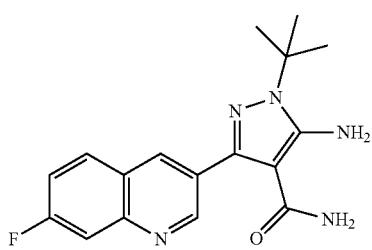 [SMILES: CC(C)(C)n1nc(-c2cnc3cc(F)ccc3c2)c(C(N)=O)c1N]

1545: 5-amino-1-tert-butyl-3-(7-fluoroquinolin-3-yl)-1H-pyrazole-4-carboxamide

Example 61

Compound 1554

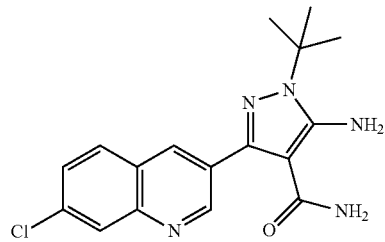 [SMILES: CC(C)(C)n1nc(-c2cnc3cc(Cl)ccc3c2)c(C(N)=O)c1N]

1554: 5-amino-1-tert-butyl-3-(7-chloroquinolin-3-yl)-1H-pyrazole-4-carboxamide. $^1$H NMR (300 MHz, CDCl$_3$) δ 9.29 (s, 1H), 8.65 (s, 1H), 8.32 (s, 1H), 7.94 (d, J=8.3 Hz, 1H), 7.69 (d, J=8.3 Hz, 1H), 5.77 (s, 2H), 1.69 (s, 9H); MS (ESI) (M+H)$^+$=344.6; HPLC analysis: 97.4% purity.

Example 62

Compound 1555

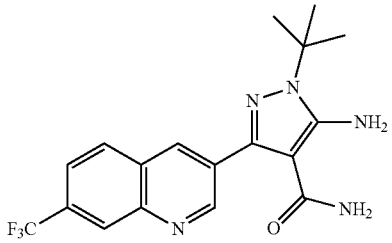 [SMILES: CC(C)(C)n1nc(-c2cnc3cc(C(F)(F)F)ccc3c2)c(C(N)=O)c1N]

1555: 5-amino-1-tert-butyl-3-(7-(trifluoromethyl)quinolin-3-yl)-1H-pyrazole-4-carboxamide. $^1$H NMR (300 MHz, CDCl$_3$) δ 9.32 (s, 1H), 8.57 (s, 1H), 8.54 (s, 1H), 8.07 (d, J=8.0 Hz, 1H), 7.85 (d, J=8.0 Hz, 1H), 5.72 (s, 2H), 1.71 (s, 9H); MS (ESI) (M+H)$^+$=378.5; HPLC analysis: 95.0% purity.

Example 63

Compound 1544

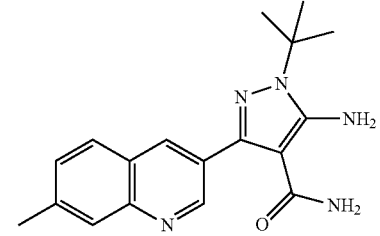 [SMILES: Cc1ccc2cc(-c3nn(C(C)(C)C)c(N)c3C(N)=O)cnc2c1]

1544: 5-amino-1-tert-butyl-3-(7-methylquinolin-3-yl)-1H-pyrazole-4-carboxamide

Example 64

Compound 1592

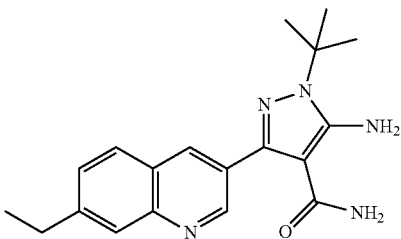

1592: 5-amino-1-(tert-butyl)-3-(7-ethylquinolin-3-yl)-1H-pyrazole-4-carboxamide. $^1$H NMR (300 MHz, CDCl$_3$) δ 9.12 (s, 1H), 8.41 (s, 1H), 8.03 (s, 1H), 7.83 (d, J=8.4 Hz, 1H), 7.51 (d, J=8.4 Hz, 1H), 5.72 (s, 2H), 5.16 (s, 2H), 2.92 (q, J=7.5 Hz, 2H), 1.72 (s, 9H), 1.39 (t, J=7.5 Hz, 3H); MS (ESI) (M+H)$^+$=338.5; HPLC analysis: 95.0% purity.

Example 65

Compound 1543

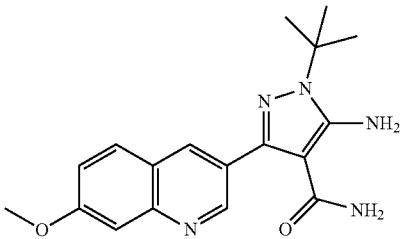 [SMILES: COc1ccc2cc(-c3nn(C(C)(C)C)c(N)c3C(N)=O)cnc2c1]

1543: 5-amino-1-tert-butyl-3-(7-methoxyquinolin-3-yl)-1H-pyrazole-4-carboxamide

Example 66

Compound 1565

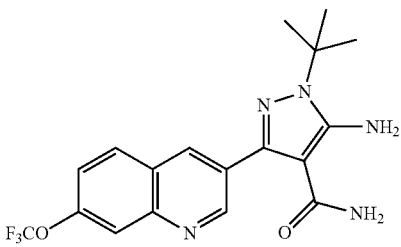 [SMILES: CC(C)(C)n1nc(-c2cnc3cc(OC(F)(F)F)ccc3c2)c(C(N)=O)c1N]

1565: 5-amino-1-tert-butyl-3-(7-(trifluoromethoxy)quinolin-3-yl)-1H-pyrazole-4-carboxamide. $^1$H NMR (500 MHz, CDCl$_3$) δ 9.23 (s, 1H), 8.51 (s, 1H), 8.09 (s, 1H), 7.97 (d, J=8.9 Hz, 1H), 7.52 (d, J=8.9 Hz, 1H), 5.71 (s, 2H), 5.18 (s, 2H), 1.72 (s, 9H); MS (ESI) (M+H)$^+$=394.3; HPLC analysis: 97.2% purity.

Example 67

Compound 1569

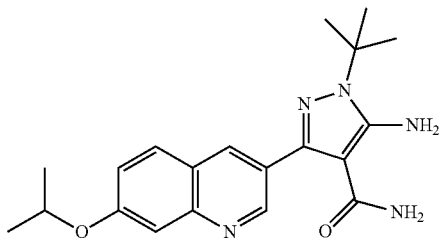 [SMILES: CC(C)Oc1ccc2cc(-c3nn(C(C)(C)C)c(N)c3C(N)=O)cnc2c1]

1569: 5-amino-1-(tert-butyl)-3-(7-isopropoxyquinolin-3-yl)-1H-pyrazole-4-carboxamide. $^1$H NMR (500 MHz, CDCl$_3$) δ 9.04 (s, 1H), 8.29 (s, 1H), 7.77 (d, J=8.9 Hz, 1H), 7.48 (s, 1H), 7.24 (d, J=8.9 Hz, 1H), 5.73 (s, 2H), 5.17 (s, 2H), 4.87-4.74 (m, 1H), 1.73 (s, 9H), 1.47 (d, J=6.0 Hz, 6H); MS (ESI) (M+H)$^+$=368.6; HPLC analysis: 98.0% purity.

Example 68

Compound 1566

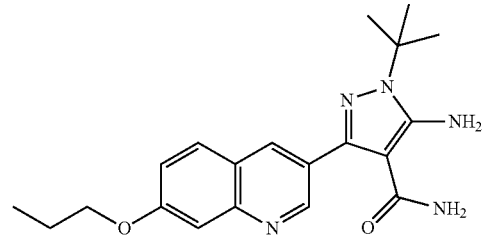 [SMILES: CCCOc1ccc2cc(-c3nn(C(C)(C)C)c(N)c3C(N)=O)cnc2c1]

1566: 5-amino-1-tert-butyl-3-(7-propoxyquinolin-3-yl)-1H-pyrazole-4-carboxamide. $^1$H NMR (300 MHz, CDCl$_3$) δ 9.24 (s, 1H), 8.84 (s, 1H), 7.98 (d, J=9.0 Hz, 1H), 7.82 (s, 1H), 7.48 (d, J=9.0 Hz, 1H), 5.89 (s, 1H), 4.20 (t, J=6.2 Hz, 2H), 2.02-1.86 (m, 2H), 1.70 (s, 6H), 1.12 (t, J=7.4 Hz, 3H); MS (ESI) (M+H)$^+$=368.5; HPLC analysis: 95.7% purity.

Example 69

Compound 1585

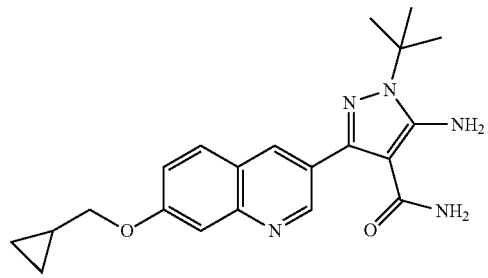 [SMILES: CC(C)(C)n1nc(-c2cnc3cc(OCC4CC4)ccc3c2)c(C(N)=O)c1N]

1585: 5-amino-1-(tert-butyl)-3-(7-(cyclopropylmethoxy)quinolin-3-yl)-1H-pyrazole-4-carboxamide. $^1$H NMR (500 MHz, CDCl$_3$) δ 9.05 (s, 1H), 8.31 (s, 1H), 7.79 (s, 1H), 7.46 (s, 1H), 7.31 (d, J=8.9 Hz, 1H), 5.72 (s, 2H), 5.17 (s, 2H), 4.01 (d, J=6.8 Hz, 2H), 1.72 (s, 9H), 1.45-1.35 (m, 1H), 0.84-0.64 (m, 2H), 0.56-0.38 (m, 2H); MS (ESI) (M+H)$^+$ =380.4; HPLC analysis: 99.0% purity.

Example 70

Compound 1586

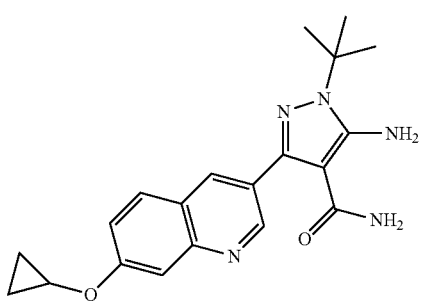 [SMILES: CC(C)(C)n1nc(-c2cnc3cc(OC4CC4)ccc3c2)c(C(N)=O)c1N]

1586: 5-amino-1-(tert-butyl)-3-(7-cyclopropoxyquinolin-3-yl)-1H-pyrazole-4-carboxamide. $^1$H NMR (500 MHz, MeOD) δ 9.29 (s, 1H), 9.25 (s, 1H), 8.30 (d, J=9.0 Hz, 1H), 7.86 (s, 1H), 7.63 (d, J=9.0 Hz, 1H), 4.20-4.11 (m, 1H), 1.71 (s, 9H), 1.08-0.98 (m, 2H), 0.95-0.86 (m, 2H); MS (ESI) (M+H)$^+$=366.5; HPLC analysis: 99.8% purity.

Example 71

Compound 1643

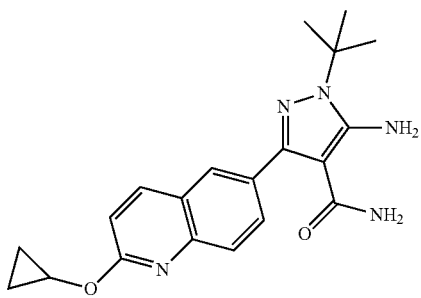 [SMILES: CC(C)(C)n1nc(-c2ccc3nc(OC4CC4)ccc3c2)c(C(N)=O)c1N]

1643: 5-amino-1-(tert-butyl)-3-(2-cyclopropoxyquinolin-6-yl)-1H-pyrazole-4-carboxamide. $^1$H NMR (500 MHz, MeOD) δ 8.24 (d, J=8.9 Hz, 1H), 8.00 (s, 1H), 7.96 (d, J=8.6 Hz, 1H), 7.82 (dd, J=8.6, 1.7 Hz, 1H), 7.06 (d, J=8.9 Hz, 1H), 4.48 (td, J=6.2, 3.1 Hz, 1H), 1.69 (s, 9H), 0.93-0.87 (m, 2H), 0.86-0.79 (m, 2H); MS (ESI) (M+H)$^+$=366.4; HPLC analysis: 96.4% purity.

Example 72

Compound 1630

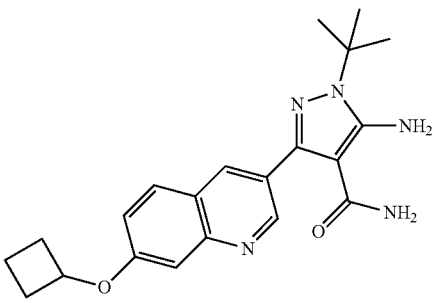 [SMILES: CC(C)(C)n1nc(-c2cnc3cc(OC4CCC4)ccc3c2)c(C(N)=O)c1N]

1630: 5-amino-1-(tert-butyl)-3-(7-cyclobutoxyquinolin-3-yl)-1H-pyrazole-4-carboxamide. $^1$H NMR (500 MHz, MeOD) δ 9.27 (s, 1H), 9.22 (s, 1H), 8.29 (d, J=9.1 Hz, 1H), 7.58 (dd, J=9.1, 1.9 Hz, 1H), 7.41 (s, 1H), 5.08-4.99 (m, 1H), 2.73-2.59 (m, 1H), 2.38-2.25 (m, 2H), 2.06-1.95 (m, 1H), 1.94-1.82 (m, 1H), 1.71 (s, 9H); MS (ESI) (M+H)$^+$=380.6; HPLC analysis: 99.0% purity.

Example 73

Compound 1639

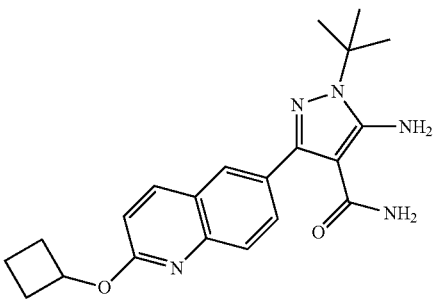 [SMILES: CC(C)(C)n1nc(-c2ccc3nc(OC4CCC4)ccc3c2)c(C(N)=O)c1N]

1639: 5-amino-1-(tert-butyl)-3-(2-cyclobutoxyquinolin-6-yl)-1H-pyrazole-4-carboxamide. $^1$H NMR (500 MHz, MeOD) δ 8.89 (d, J=9.1 Hz, 1H), 8.34 (s, 1H), 8.17 (d, J=8.2 Hz, 1H), 7.98 (d, J=8.2 Hz, 1H), 7.52 (d, J=9.1 Hz, 1H), 5.55-5.35 (m, 1H), 2.79-2.61 (m, 2H), 2.51-2.32 (m, 2H), 2.10-1.98 (m, 1H), 1.94-1.81 (m, 1H), 1.71 (s, 9H); MS (ESI) (M+H)$^+$=380.5; HPLC analysis: 98.3% purity.

Example 74

Compound 1657

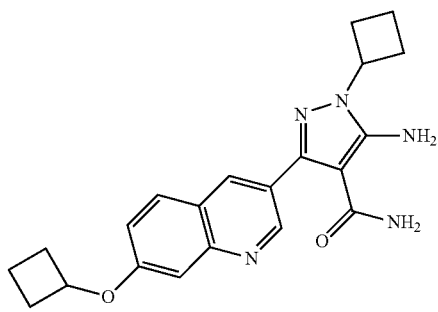 [SMILES: NC(=O)c1c(-c2cnc3cc(OC4CCC4)ccc3c2)nn(C2CCC2)c1N]

1657: 5-amino-3-(7-cyclobutoxyquinolin-3-yl)-1-cyclobutyl-1H-pyrazole-4-carboxamide. $^1$H NMR (500 MHz, MeOD) δ 9.32 (s, 1H), 9.26 (s, 1H), 8.29 (d, J=9.1 Hz, 1H), 7.58 (d, J=9.1 Hz, 1H), 7.43 (s, 1H), 5.08-5.00 (m, 1H), 2.75-2.60 (m, 4H), 2.53-2.39 (m, 2H), 2.37-2.25 (m, 2H), 2.04-1.83 (m, 4H); MS (ESI) (M+H)$^+$=378.6; HPLC analysis: 97.4% purity.

Example 75

Compound 1656

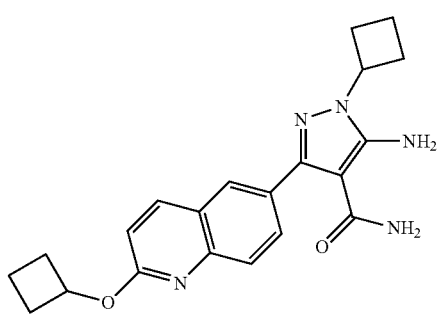 [SMILES: NC(=O)c1c(-c2ccc3nc(OC4CCC4)ccc3c2)nn(C2CCC2)c1N]

1656: 5-amino-3-(2-cyclobutoxyquinolin-6-yl)-1-cyclobutyl-1H-pyrazole-4-carboxamide. $^1$H NMR (500 MHz, CDCl$_3$) δ 8.09 (d, J=8.7 Hz, 2H), 7.97 (s, 1H), 7.85 (d, J=8.6 Hz, 1H), 6.96 (d, J=8.6 Hz, 1H), 5.60-5.48 (m, 1H), 5.20 (s, 2H), 4.63-4.51 (m, 1H), 2.86-2.73 (m, 2H), 2.68-2.56 (m, 2H), 2.52-2.40 (m, 2H), 2.33-2.19 (m, 2H), 2.00-1.86 (m, 4H); MS (ESI) (M+H)$^+$=378.7; HPLC analysis: 97.8% purity.

Example 76

Compound 1658

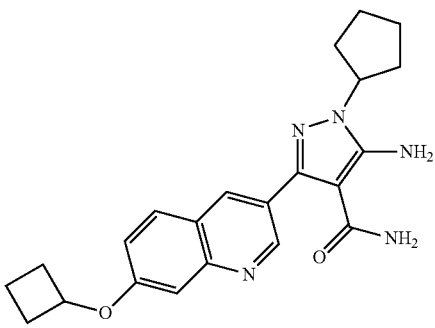 [SMILES: NC(=O)c1c(-c2cnc3cc(OC4CCC4)ccc3c2)nn(C2CCCC2)c1N]

1658: 5-amino-3-(7-cyclobutoxyquinolin-3-yl)-1-cyclopentyl-1H-pyrazole-4-carboxamide. $^1$H NMR (500 MHz, MeOD) δ 9.28 (s, 1H), 9.23 (s, 1H), 8.28 (d, J=9.0 Hz, 1H), 7.57 (d, J=9.0 Hz, 1H), 7.40 (s, 1H), 5.06-4.99 (m, 1H), 4.73-4.67 (m, 1H), 2.70-2.58 (m, 2H), 2.37-2.24 (m, 2H), 2.20-2.04 (m, 4H), 2.04-1.82 (m, 4H), 1.81-1.68 (m, 2H); MS (ESI) (M+H)$^+$=392.6; HPLC analysis: 98.7% purity.

Example 77

Compound 1653

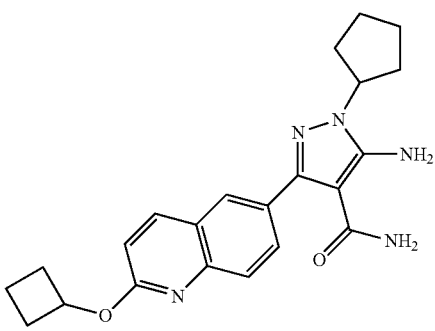 [SMILES: NC(=O)c1c(-c2ccc3nc(OC4CCC4)ccc3c2)nn(C2CCCC2)c1N]

1653: 5-amino-3-(2-cyclobutoxyquinolin-6-yl)-1-cyclopentyl-1H-pyrazole-4-carboxamide. $^1$H NMR (500 MHz, MeOD) δ 8.88 (d, J=8.7 Hz, 1H), 8.34 (s, 1H), 8.16 (d, J=8.1 Hz, 1H), 7.98 (d, J=8.1 Hz, 1H), 7.51 (d, J=8.7 Hz, 1H), 5.49-5.40 (m, 1H), 4.75-4.67 (m, 2H), 2.77-2.60 (m, 2H), 2.49-2.33 (m, 2H), 2.25-2.10 (m, 2H), 2.06-1.83 (m, 6H), 1.81-1.66 (s, 2H); MS (ESI) (M+H)$^+$=392.5; HPLC analysis: 99.5% purity.

Example 78

Compound 1647

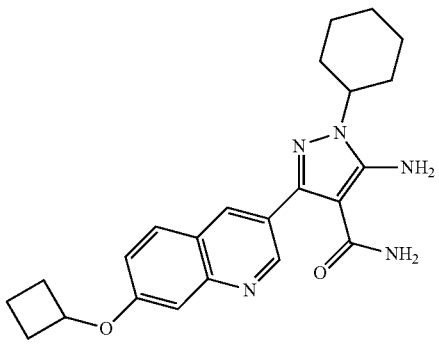 [SMILES: NC(=O)c1c(-c2cnc3cc(OC4CCC4)ccc3c2)nn(C2CCCCC2)c1N]

1647: 5-amino-3-(7-cyclobutoxyquinolin-3-yl)-1-cyclohexyl-1H-pyrazole-4-carboxamide. $^1$H NMR (500 MHz, MeOD) δ 9.28 (s, 1H), 9.23 (s, 1H), 8.28 (d, J=9.0 Hz, 1H), 7.57 (d, J=9.0 Hz, 1H), 7.42 (s, 1H), 5.07-5.00 (m, 1H), 4.25-4.11 (m, 1H), 2.71-2.61 (m, 2H), 2.38-2.25 (m, 2H), 2.05-1.84 (m, 8H), 1.83-1.73 (m, 1H), 1.61-1.47 (m, 2H), 1.38-1.24 (m, 1H); MS (ESI) (M+H)$^+$=406.6; HPLC analysis: 97.2% purity.

Example 79

Compound 1646

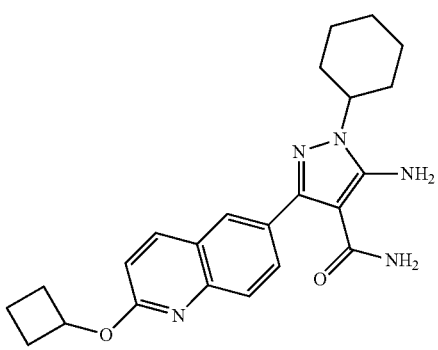 [SMILES: NC(=O)c1c(-c2ccc3nc(OC4CCC4)ccc3c2)nn(C2CCCCC2)c1N]

1646: 5-amino-3-(2-cyclobutoxyquinolin-6-yl)-1-cyclohexyl-1H-pyrazole-4-carboxamide. $^1$H NMR (500 MHz, MeOD) δ 8.88 (d, J=8.9 Hz, 1H), 8.37 (s, 1H), 8.15 (d, J=8.6 Hz, 1H), 8.01 (d, J=8.6 Hz, 2H), 7.52 (d, J=8.9 Hz, 1H), 5.52-5.41 (m, 1H), 4.38-4.23 (m, 1H), 2.78-2.63 (m, 2H), 2.51-2.34 (m, 2H), 2.08-2.00 (m, 2H), 2.00-1.93 (m, 2H), 1.92-1.83 (m, 4H), 1.82-1.74 (m, 1H), 1.64-1.48 (m, 2H), 1.40-1.25 (m, 1H); MS (ESI) (M+H)$^+$=406.6; HPLC analysis: 96.3% purity.

Example 80

Compound 1644

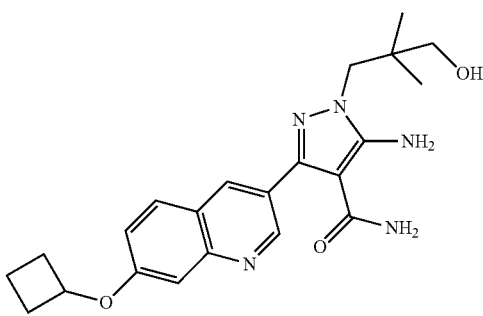 [SMILES: CC(C)(CO)Cn1nc(-c2cnc3cc(OC4CCC4)ccc3c2)c(C(N)=O)c1N]

1644: 5-amino-3-(7-cyclobutoxyquinolin-3-yl)-1-(3-hydroxy-2,2-dimethylpropyl)-1H-pyrazole-4-carboxamide. $^1$H NMR (500 MHz, MeOD) δ 9.28 (s, 1H), 9.23 (s, 1H), 8.29 (d, J=9.0 Hz, 1H), 7.58 (d, J=9.0 Hz, 1H), 7.46 (s, 1H), 5.08-5.00 (m, 2H), 3.95 (s, 2H), 2.74-2.61 (m, 2H), 2.39-2.24 (m, 2H), 2.06-1.95 (m, 1H), 1.95-1.82 (m, 1H), 1.04 (s, 6H); MS (ESI) (M+H)$^+$=410.6; HPLC analysis: 95.7% purity.

Example 81

Compound 1645

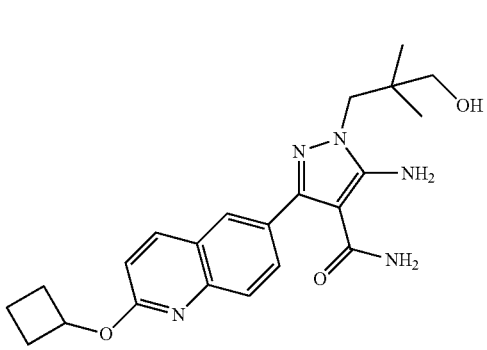 [SMILES: CC(C)(CO)Cn1nc(-c2ccc3nc(OC4CCC4)ccc3c2)c(C(N)=O)c1N]

1645: 5-amino-3-(2-cyclobutoxyquinolin-6-yl)-1-(3-hydroxy-2,2-dimethylpropyl)-1H-pyrazole-4-carboxamide. $^1$H NMR (500 MHz, MeOD) δ 8.76 (d, J=8.6 Hz, 1H), 8.29 (s, 1H), 8.09 (d, J=7.2 Hz, 1H), 7.98 (d, J=8.2 Hz, 1H), 7.42 (d, J=8.6 Hz, 1H), 5.50-5.40 (m, 1H), 3.94 (s, 2H), 3.37 (s, 2H), 2.77-2.62 (m, 2H), 2.48-2.30 (m, 2H), 2.09-1.95 (m, 1H), 1.95-1.77 (m, 1H), 1.04 (s, 6H); MS (ESI) (M+H)$^+$=410.5; HPLC analysis: 99.7% purity.

Examples 82-103

Additional compounds were prepared using the above-disclosed methods:

| Ex. No. | Comp. No. | Structure | Chemical Name and Chemical Data |
|---|---|---|---|
| 82 | 1570 | 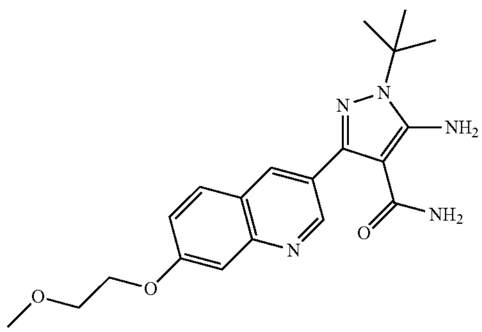 [SMILES: COCCOc1ccc2cc(-c3nn(C(C)(C)C)c(N)c3C(N)=O)cnc2c1] | 5-amino-1-(tert-butyl)-3-(7-(2-methoxyethoxy)quinolin-3-yl)-1H-pyrazole-4-carboxamide<br>MS (ESI) (M + H)$^+$ = 384.5 |
| 83 | 1577 | 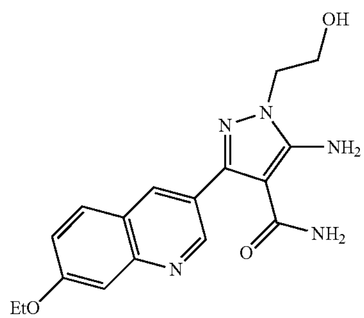 [SMILES: CCOc1ccc2cc(-c3nn(CCO)c(N)c3C(N)=O)cnc2c1] | 5-amino-3-(7-ethoxyquinolin-3-yl)-1-(2-hydroxyethyl)-1H-pyrazole-4-carboxamide<br>MS (ESI) (M + H)$^+$ = 342.4 |
| 84 | 1587 | 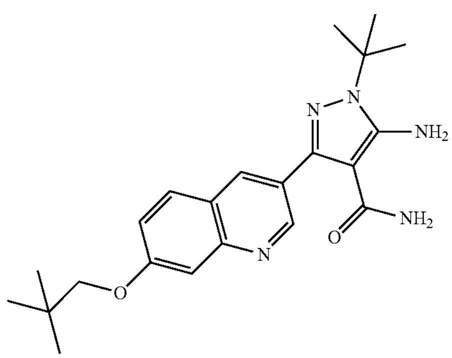 [SMILES: CC(C)(C)COc1ccc2cc(-c3nn(C(C)(C)C)c(N)c3C(N)=O)cnc2c1] | 5-amino-1-(tert-butyl)-3-(7-(neopentyloxy)quinolin-3-yl)-1H-pyrazole-4-carboxamide<br>MS (ESI) (M + H)$^+$ = 396.6 |
| 85 | 1588 | 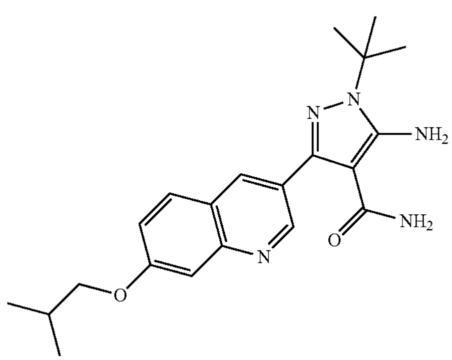 [SMILES: CC(C)COc1ccc2cc(-c3nn(C(C)(C)C)c(N)c3C(N)=O)cnc2c1] | 5-amino-1-(tert-butyl)-3-(7-isobutoxyquinolin-3-yl)-1H-pyrazole-4-carboxamide<br>$^1$H NMR (500 MHz, MeOD) δ 9.27 (s, 1H), 9.23 (s, 1H), 8.30 (d, J = 9.2 Hz, 1H), 7.63 (dd, J = 9.2, 1.8 Hz, 1H), 7.55 (s, 1H), 4.09 (d, J = 6.4 Hz, 2H), 2.35-2.16 (m, 1H), 1.72 (s, 9H), 1.15 (d, J = 6.6 Hz, 6H); MS (ESI) (M + H)$^+$ = 382.4; HPLC analysis: 99.2% purity. |

| Ex. No. | Comp. No. | Structure | Chemical Name and Chemical Data |
|---|---|---|---|
| 86 | 1593 | 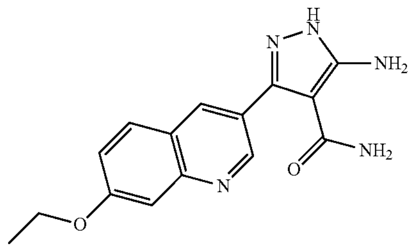 [SMILES: CCOc1ccc2cc(-c3n[nH]c(N)c3C(N)=O)cnc2c1] | 5-amino-3-(7-ethoxyquinolin-3-yl)-1H-pyrazole-4-carboxamide<br>$^1$H NMR (300 MHz, MeOD) δ 8.94 (s, 1H), 8.46 (d, J = 2.0 Hz, 1H), 7.92 (d, J = 9.0 Hz, 1H), 7.41 (d, J = 2.0 Hz, 1H), 7.32 (dd, J = 9.0, 2.0 Hz, 1H), 4.25 (q, J = 7.0 Hz, 2H), 1.51 (t, J = 7.0 Hz, 3H); MS (ESI) (M + H)$^+$ = 298.5; HPLC analysis: 99.0% purity. |
| 87 | 1594 | 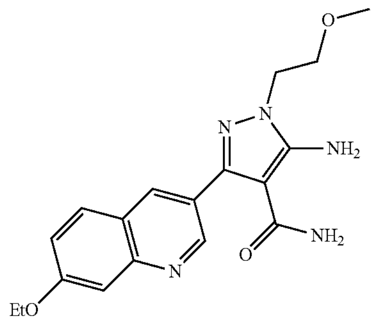 [SMILES: CCOc1ccc2cc(-c3nn(CCOC)c(N)c3C(N)=O)cnc2c1] | 5-amino-3-(7-ethoxyquinolin-3-yl)-1-(2-methoxyethyl)-1H-pyrazole-4-carboxamide<br>MS (ESI) (M + H)$^+$ = 356.7 |
| 88 | 1595 | 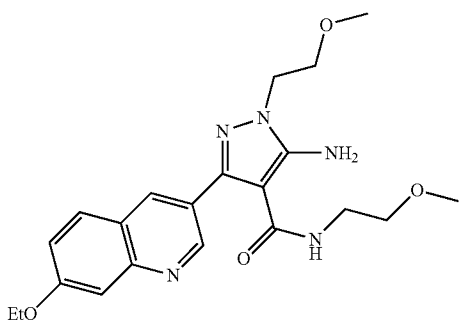 [SMILES: CCOc1ccc2cc(-c3nn(CCOC)c(N)c3C(=O)NCCOC)cnc2c1] | 5-amino-3-(7-ethoxyquinolin-3-yl)-N,1-bis(2-methoxyethyl)-1H-pyrazole-4-carboxamide<br>MS (ESI) (M + H)$^+$ = 414.8 |
| 89 | 1607 | 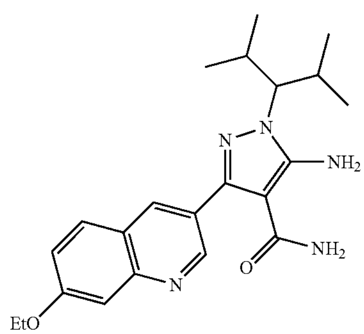 [SMILES: CCOc1ccc2cc(-c3nn(C(C(C)C)C(C)C)c(N)c3C(N)=O)cnc2c1] | 5-amino-1-(2,4-dimethylpentan-3-yl)-3-(7-ethoxyquinolin-3-yl)-1H-pyrazole-4-carboxamide<br>MS (ESI) (M + H)$^+$ = 396.6 |
| 90 | 1609 | 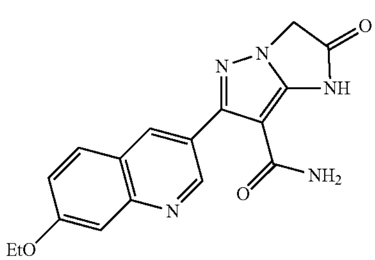 [SMILES: CCOc1ccc2cc(-c3nn4c(c3C(N)=O)NC(=O)C4)cnc2c1] | 6-(7-ethoxyquinolin-3-yl)-2-oxo-2,3-dihydro-1H-imidazo[1,2-b]pyrazole-7-carboxamide<br>$^1$H NMR (500 MHz, DMSO) δ 9.26 (d, J = 12.9 Hz, 1H), 9.17 (s, 1H), 8.35 (d, J = 9.1 Hz, 1H), 7.72 (s, 1H), 7.59 (d, J = 9.1 Hz, 1H), 6.77 (s, 2H), 4.88 (s, 2H), 4.30 (q, J = 6.7 Hz, 2H), 1.46 (t, J = 6.7 Hz, 3H), MS (ESI) (M + H)$^+$ = 338.5 |

-continued

| Ex. No. | Comp. No. | Structure | Chemical Name and Chemical Data |
|---|---|---|---|
| 91 | 1611 | 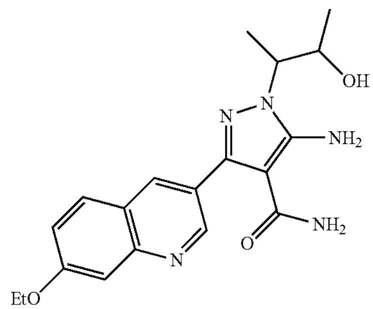 [SMILES: CCOc1ccc2cc(-c3nn(C(C)C(C)O)c(N)c3C(N)=O)cnc2c1] | 5-amino-3-(7-ethoxyquinolin-3-yl)-1-(3-hydroxybutan-2-yl)-1H-pyrazole-4-carboxamide<br>$^1$H NMR (500 MHz, MeOD) δ 8.99 (d, J = 12.0 Hz, 1H), 8.55 (d, J = 7.6 Hz, 1H), 7.96 (d, J = 9.0 Hz, 1H), 7.42 (d, J = 1.8 Hz, 1H), 7.35 (d, J = 9.0 Hz, 1H), 4.26 (q, J = 7.0 Hz, 2H), 4.23-4.17 (m, 1H), 4.16-4.05 (m, 1H), 1.60-1.45 (m, 6H), 1.28 (d, J = 6.3 Hz, 2H), 1.12 (d, J = 6.2 Hz, 2H). MS (ESI) (M + H)$^+$ = 370.6 |
| 92 | 1612 | 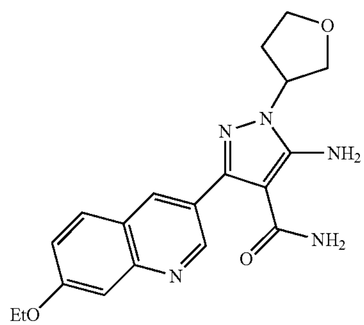 [SMILES: CCOc1ccc2cc(-c3nn(C4CCOC4)c(N)c3C(N)=O)cnc2c1] | 5-amino-3-(7-ethoxyquinolin-3-yl)-1-(tetrahydrofuran-3-yl)-1H-pyrazole-4-carboxamide<br>MS (ESI) (M + H)$^+$ = 368.7 |
| 93 | 1626 | 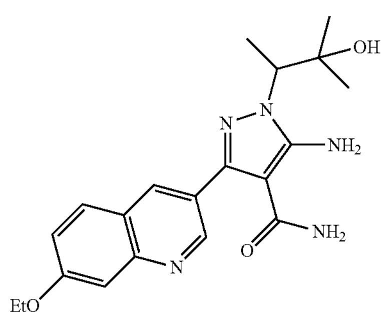 [SMILES: CCOc1ccc2cc(-c3nn(C(C)C(C)(C)O)c(N)c3C(N)=O)cnc2c1] | 5-amino-3-(7-ethoxyquinolin-3-yl)-1-(3-hydroxy-3-methylbutan-2-yl)-1H-pyrazole-4-carboxamide<br>$^1$H NMR (500 MHz, MeOD) δ 9.31 (s, 1H), 9.26 (s, 1H), 8.30 (d, J = 9.2 Hz, 1H), 7.62 (d, J = 9.2 Hz, 1H), 7.54 (s, 1H), 4.38 (q, J = 7.0 Hz, 2H), 4.36-4.29 (m, 1H), 1.59-1.53 (m, 6H), 1.30 (s, 3H), 1.26 (s, 3H), MS (ESI) (M + H)$^+$ = 384.6 |
| 94 | 1628 | 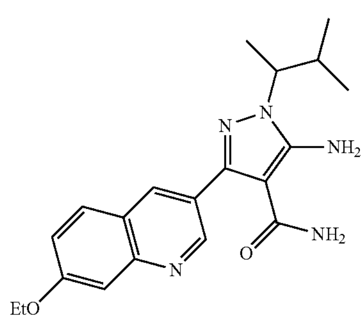 [SMILES: CCOc1ccc2cc(-c3nn(C(C)C(C)C)c(N)c3C(N)=O)cnc2c1] | 5-amino-3-(7-ethoxyquinolin-3-yl)-1-(3-methylbutan-2-yl)-1H-pyrazole-4-carboxamide<br>MS (ESI) (M + H)$^+$ = 368.6 |

-continued

| Ex. No. | Comp. No. | Structure | Chemical Name and Chemical Data |
|---|---|---|---|
| 95 | 1629 | 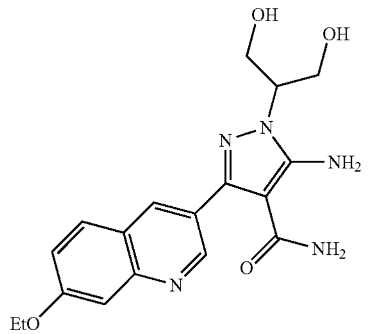 [SMILES: CCOc1ccc2cc(-c3nn(C(CO)CO)c(N)c3C(N)=O)cnc2c1] | 5-amino-1-(1,3-dihydroxypropan-2-yl)-3-(7-ethoxyquinolin-3-yl)-1H-pyrazole-4-carboxamide<br>MS (ESI) (M + H)$^+$ = 372.5 |
| 96 | 1631 | 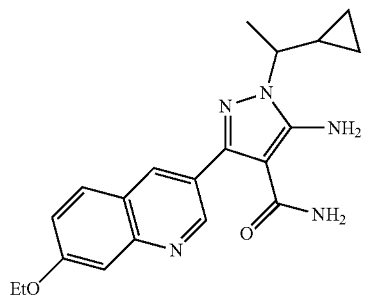 [SMILES: CCOc1ccc2cc(-c3nn(C(C)C4CC4)c(N)c3C(N)=O)cnc2c1] | 5-amino-1-(1-cyclopropylethyl)-3-(7-ethoxyquinolin-3-yl)-1H-pyrazole-4-carboxamide<br>MS (ESI) (M + H)$^+$ = 366.7 |
| 97 | 1634 | 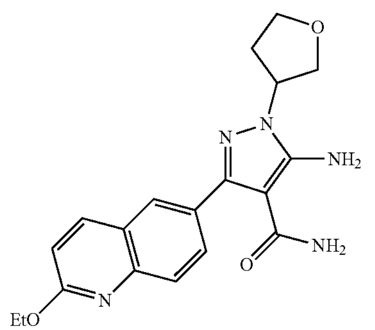 [SMILES: CCOc1ccc2cc(-c3nn(C4CCOC4)c(N)c3C(N)=O)ccc2n1] | 5-amino-3-(2-ethoxyquinolin-6-yl)-1-(tetrahydrofuran-3-yl)-1H-pyrazole-4-carboxamide<br>MS (ESI) (M + H)$^+$ = 368.5 |
| 98 | 1636 | 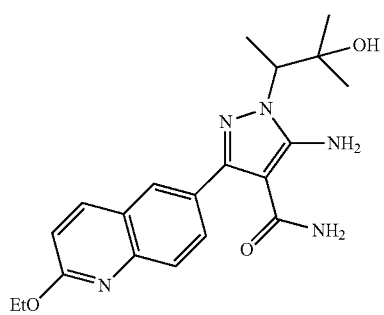 [SMILES: CCOc1ccc2cc(-c3nn(C(C)C(C)(C)O)c(N)c3C(N)=O)ccc2n1] | 5-amino-3-(2-ethoxyquinolin-6-yl)-1-(3-hydroxy-3-methylbutan-2-yl)-1H-pyrazole-4-carboxamide<br>MS (ESI) (M + H)$^+$ = 384.8 |
| 99 | 1637 | 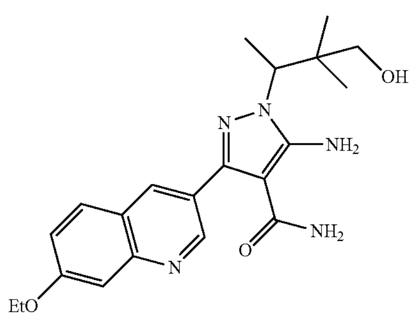 [SMILES: CCOc1ccc2cc(-c3nn(C(C)C(C)(C)CO)c(N)c3C(N)=O)cnc2c1] | 5-amino-3-(7-ethoxyquinolin-3-yl)-1-(4-hydroxy-3,3-dimethylbutan-2-yl)-1H-pyrazole-4-carboxamide<br>$^1$H NMR (500 MHz, MeOD) δ 9.27 (s, 1H), 9.24 (s, 1H), 8.30 (d, J = 9.1 Hz, 1H), 7.62 (d, J = 9.1 Hz, 1H), 7.51 (s, 1H), 4.48-4.35 (m, 5H), 1.61-1.50 (m, 6H), 1.11 (s, 3H), 1.00 (s, 3H); MS (ESI) (M + H)$^+$ = 398.6 |

-continued

| Ex. No. | Comp. No. | Structure | Chemical Name and Chemical Data |
|---|---|---|---|
| 100 | 1640 | 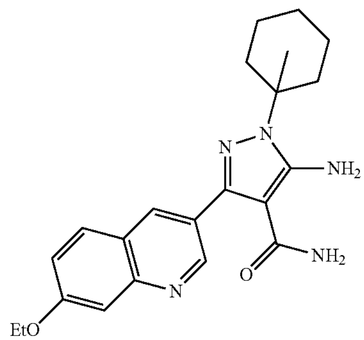 | 5-amino-3-(7-ethoxyquinolin-3-yl)-1-(1-methylcyclohexyl)-1H-pyrazole-4-carboxamide MS (ESI) (M + H)$^+$ = 394.7 |
| 101 | 1654 | 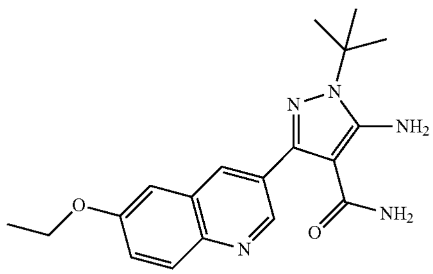 [SMILES: CCOc1ccc2ncc(-c3nn(C(C)(C)C)c(N)c3C(N)=O)cc2c1] | 5-amino-1-(tert-butyl)-3-(6-ethoxyquinolin-3-yl)-1H-pyrazole-4-carboxamide MS (ESI) (M + H)$^+$ = 354.6 |
| 102 | 1655 | 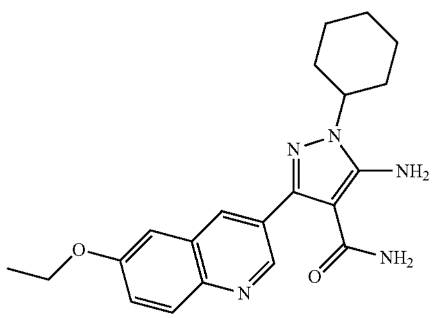 [SMILES: CCOc1ccc2ncc(-c3nn(C4CCCCC4)c(N)c3C(N)=O)cc2c1] | 5-amino-1-cyclohexyl-3-(6-ethoxyquinolin-3-yl)-1H-pyrazole-4-carboxamide $^1$H NMR (500 MHz, MeOD) δ 8.85 (s, 1H), 8.31 (s, 1H), 7.99 (d, J = 9.2 Hz, 1H), 7.42 (d, J = 9.2 Hz, 1H), 7.13 (s, 1H), 4.15 (q, J = 6.9 Hz, 3H), 4.09 (s, 3H), 3.97-3.79 (m, 1H), 1.93-1.83 (m, 6H), 1.48 (t, J= 6.9 Hz, 3H), 1.44-1.35 (m, 2H), 1.32-1.18 (m, 2H). MS (ESI) (M + H)$^+$ = 380.5 |
| 103 | 1661 | 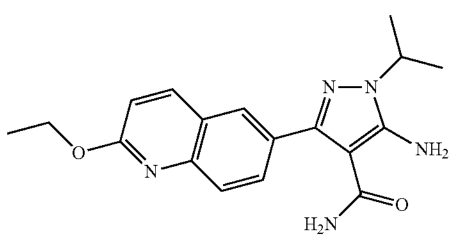 [SMILES: CCOc1ccc2cc(-c3nn(C(C)C)c(N)c3C(N)=O)ccc2n1] | 5-amino-3-(2-ethoxyquinolin-6-yl)-1-isopropyl-1H-pyrazole-4-carboxamide $^1$H NMR (500 MHz, MeOD) δ 8.86 (d, J = 8.9 Hz, 1H), 8.37 (s, 1H), 8.15 (d, J = 8.5 Hz, 1H), 8.04 (d, J = 8.5 Hz, 1H), 7.61 (d, J = 8.9 Hz, 1H), 4.76 (q, J = 6.6 Hz, 2H), 4.71-4.62 (m, 1H), 1.61 (t, J = 6.6 Hz, 3H), 1.53 (d, J = 6.5 Hz, 6H), MS (ESI) (M + H)$^+$ = 340.5; HPLC analysis: 99.3% purity. |

Example 104

Inhibition of TgCDPK1 and CpCDPK1

Inhibition of TgCDPK1 and CpCDPK1 was determined using a luminescent kinase assay which measures ATP depletion in the presence of the Syntide 2 peptide substrate (KinaseGlo). For description of the methods and assays, see WO 2011/094628, incorporated by reference herein. Similar to TgCDPK1, exogenous calcium was necessary for CpCDPK1 to possess maximum catalytic activity (data not shown). Notably, both kinases were tested at the same ATP concentration which allows direct comparison of inhibitor potencies due to these enzymes possessing similar $K_m$s for this cofactor. The following compounds were tested for inhibition of TgCDPK1 and CpCDPK1 according to the known methods:

TABLE 1

TgCDPK1 and CpCDPK1 IC$_{50}$ data

| Entry No. | Comp. No. | TgCDPK1 IC$_{50}$ (μM) | CpCDPK1 IC$_{50}$ (μM) |
|---|---|---|---|
| 1 | 1 | 0.002 | 0.004 |
| 2 | 2 | 0.008 | 0.016 |

TABLE 1-continued

TgCDPK1 and CpCDPK1 IC$_{50}$ data

| Entry No. | Comp. No. | TgCDPK1 IC$_{50}$ (µM) | CpCDPK1 IC$_{50}$ (µM) |
|---|---|---|---|
| 3 | 3 | 0.004 | 0.004 |
| 4 | 4 | 0.033 | 0.043 |
| 5 | 5 | 0.13 | 0.13 |
| 6 | 6 | 0.035 | 0.064 |
| 7 | 7 | 0.003 | 0.001 |
| 8 | 8 | 0.011 | 0.009 |
| 9 | 9 | 0.003 | 0.001 |
| 10 | 10 | 0.035 | 0.014 |
| 11 | 11 | 0.081 | 0.048 |
| 12 | 12 | 0.008 | 0.011 |
| 13 | 13 | 0.006 | 0.007 |
| 14 | 14 | 0.008 | 0.016 |
| 15 | 15 | 0.007 | 0.010 |
| 16 | 16 | 0.059 | 0.15 |
| 17 | 17 | 0.011 | 0.016 |
| 18 | 18 | 0.004 | 0.007 |
| 19 | 19 | 0.011 | 0.024 |
| 20 | 20 | 0.026 | 0.013 |
| 21 | 21 | 0.039 | 0.017 |
| 22 | 22 | 0.015 | 0.021 |
| 23 | 23 | 0.005 | 0.018 |
| 24 | 24 | 0.007 | 0.017 |
| 25 | 25 | 0.002 | 0.002 |
| 26 | 26 | 0.007 | 0.010 |
| 27 | 27 | 0.71 | 2.3 |
| 28 | 28 | 0.040 | 0.42 |
| 29 | 29 | 0.017 | 0.20 |
| 30 | 30 | 0.032 | 0.15 |
| 31 | 31 | 0.64 | >3 |
| 32 | 32 | >3 | >3 |
| 33 | 33 | 0.73 | 0.99 |
| 34 | 34 | 0.032 | 0.20 |
| 35 | 35 | 0.049 | 0.29 |
| 36 | 36 | 0.35 | 0.39 |
| 37 | 37 | 0.010 | 0.070 |
| 38 | 38 | 0.006 | 0.007 |
| 39 | 39 | 0.002 | 0.001 |
| 40 | 1517 | 0.002 | 0.001 |
| 41 | 1572 | 0.008 | 0.005 |
| 42 | 1573 | 0.028 | 0.008 |
| 43 | 1591 | 0.021 | 0.007 |
| 44 | 1575 | 0.013 | 0.005 |
| 45 | 1598 | 0.012 | 0.005 |
| 46 | 1652 | 0.012 | 0.003 |
| 47 | 1605 | 0.011 | 0.004 |
| 48 | 1571 | 0.008 | 0.005 |
| 49 | 1606 | 0.031 | 0.008 |
| 50 | 1604 | 0.006 | 0.002 |
| 51 | 1574 | 0.080 | 0.030 |
| 52 | 1627 | 0.020 | 0.009 |
| 53 | 1641 | 0.041 | 0.021 |
| 54 | 1608 | 0.017 | 0.005 |
| 55 | 1596 | 0.011 | 0.005 |
| 56 | 1597 | 0.006 | 0.003 |
| 57 | 1635 | 0.006 | 0.003 |
| 58 | 1633 | 0.004 | 0.002 |
| 59 | 1632 | 0.007 | 0.006 |
| 60 | 1622 | 0.007 | 0.002 |
| 61 | 1545 | 0.006 | 0.006 |
| 62 | 1554 | 0.036 | 0.022 |
| 63 | 1555 | 0.247 | 0.222 |
| 64 | 1544 | 0.016 | 0.011 |
| 65 | 1592 | 0.115 | 0.085 |
| 66 | 1543 | 0.005 | 0.003 |
| 67 | 1565 | 0.031 | 0.038 |
| 68 | 1569 | 0.011 | 0.005 |
| 69 | 1566 | 0.005 | 0.003 |
| 70 | 1585 | 0.016 | 0.009 |
| 71 | 1588 | 0.086 | 0.052 |
| 72 | 1586 | 0.010 | 0.005 |
| 73 | 1643 | 0.0057 | 0.003 |
| 74 | 1630 | 0.003 | 0.004 |
| 75 | 1639 | 0.005 | 0.006 |
| 76 | 1657 | 0.012 | 0.005 |
| 77 | 1656 | 0.007 | 0.003 |
| 78 | 1658 | 0.012 | 0.004 |
| 79 | 1653 | 0.012 | 0.006 |
| 80 | 1647 | 0.019 | 0.008 |
| 81 | 1646 | 0.016 | 0.013 |
| 82 | 1644 | 0.012 | 0.005 |
| 83 | 1645 | 0.010 | 0.005 |
| 84 | 1570 | 0.258 | 0.255 |
| 85 | 1577 | 0.181 | 0.089 |
| 86 | 1587 | 0.175 | 0.490 |
| 87 | 1593 | 0.164 | 0.067 |
| 88 | 1594 | 0.321 | 0.172 |
| 89 | 1595 | 0.723 | 0.398 |
| 90 | 1607 | 0.099 | 0.020 |
| 91 | 1609 | 1.433 | 0.577 |
| 92 | 1611 | 0.019 | 0.006 |
| 93 | 1612 | 0.010 | 0.003 |
| 94 | 1626 | 0.03 | 0.013 |
| 95 | 1628 | 0.011 | 0.005 |
| 96 | 1629 | 0.12 | 0.052 |
| 97 | 1631 | 0.010 | 0.005 |
| 98 | 1634 | 0.006 | 0.003 |
| 99 | 1636 | 0.058 | 0.018 |
| 100 | 1637 | 0.012 | 0.004 |
| 101 | 1640 | 0.009 | 0.006 |
| 102 | 1654 | >2 | >2 |
| 103 | 1655 | >2 | >2 |
| 104 | 1661 | 0.005 | 0.002 |

Example 105

Additional Biological Data

A select group of compounds with low nanomolar IC$_{50}$s for CDPK1s were tested for inhibition of a mammalian kinase with a small gatekeeper residue (Src), for inhibition of *T. gondii* cell proliferation, and for cytotoxicity against a mammalian cell line (CRL8155) using reported procedures (see WO 2011/094628, incorporated by reference herein). The results are summarized in Tables 2 and 3. Some of the compounds were several thousand-fold selective for TgCDPK1 over Src. Most inhibited parasite proliferation at sub-micromolar concentrations, and all of them demonstrated low toxicity to mammalian cells.

TABLE 2

Further characterization of select compounds of the disclosure.

| Entry No. | Comp. No. | Src IC$_{50}$ (µM) | Selectivity Index (Src/TgCDPK1) | *T. gondii* EC$_{50}$ (µM) | Cytotoxicity (CRL8155) EC$_{50}$ (µM) |
|---|---|---|---|---|---|
| 1 | 1 | 1.3 | 650 | 0.26 | >40 |
| 2 | 3 | 7.3 | 1825 | 0.39 | >30 |
| 3 | 18 | 0.98 | 245 | 0.26 | >30 |
| 4 | 19 | 2.7 | 225 | 0.32 | >40 |
| 5 | 25 | 6.9 | >3500 | 0.072 | >40 |
| 6 | 38 | >10 | >1600 | 1.1 | >40 |
| 7 | 39 | >30 | >15000 | 0.22 | >30 |

TABLE 3

Further characterization of select compounds of the disclosure with solubility data.

| Entry No. | Comp. No. | T. gondii $EC_{50}$ (μM) | Cytotoxicity (CRL8155) $EC_{50}$ (μM) | Src $IC_{50}$ (μM) | Solubility pH = 6.5 |
|---|---|---|---|---|---|
| 1 | 1517 | 0.22 | >30 | >30 | 26 |
| 2 | 1597 | 0.20 | >40 | >10 | 83.5 |
| 3 | 1572 | 0.72 | — | >30 | 99.0 |
| 4 | 1598 | 1.21 | >40 | >10 | 26.5 |
| 5 | 1635 | 0.48 | >40 | >10 | 10.9 |
| 6 | 1652 | 0.52 | >40 | >10 | 10.9 |
| 7 | 1605 | 0.97 | >40 | >10 | 98.7 |
| 8 | 1571 | 0.33 | — | >10 | 34.3 |
| 9 | 1633 | 0.43 | >40 | >10 | 88.9 |
| 10 | 1604 | 0.41 | >40 | >10 | 8.5 |
| 11 | 1632 | 0.32 | — | — | 46.5 |
| 12 | 1596 | 1.19 | >40 | >10 | >100 |
| 13 | 1622 | 0.21 | >40 | >10 | >100 |
| 14 | 1545 | 2.25 | >40 | >30 | >100 |
| 15 | 1543 | 0.59 | >40 | >30 | >100 |
| 16 | 1569 | 1.21 | >40 | — | >100 |
| 17 | 1566 | 0.69 | >40 | >10 | 12.7 |
| 18 | 1585 | 1.47 | — | — | 26.8 |
| 19 | 1586 | 0.43 | — | 4.75 | 83.7 |
| 20 | 1643 | 0.045 | >40 | >10 | 96.3 |
| 21 | 1630 | 0.48 | >40 | >10 | 3.7 |
| 22 | 1639 | 0.48 | >40 | >10 | 80.6 |
| 23 | 1657 | 0.69 | >40 | >10 | 76.1 |
| 24 | 1656 | 0.069 | >40 | >10 | 8.7 |
| 25 | 1658 | 0.40 | >40 | >10 | 59.7 |
| 26 | 1653 | 0.21 | >40 | >10 | 43.1 |
| 27 | 1647 | 1.14 | >40 | >10 | 87.8 |
| 28 | 1646 | 0.31 | >40 | >10 | 31.0 |
| 29 | 1644 | 0.77 | >40 | >10 | 97.5 |
| 30 | 1645 | 0.48 | >40 | >10 | 45.8 |

All compounds were assayed for inhibition of TgCDPK1 and CpCDPK1 and on the small-gatekeeper (Thr) human kinases, Src and Abl. Human cell toxicity was evaluated in two human cell lines, HepG2 (hepatocellular carcinoma) and CRL8155 (lymphoblast, spleen). hERG inhibition has been associated with long Q-T syndrome (cardiotoxicity), and the compounds were evaluated for hERG inhibitory activity. The results comparing several compounds of the disclosure are shown in Table 4.

TABLE 4

| Comp. No. | Enzyme Inhibition ($IC_{50}$, μM) | | | | Inhibit Parasite Prolif. ($EC_{50}$, μM) | | Cell toxicity ($EC_{50}$, μM) | | hERG ($IC_{50}$, μM) | Solubility pH 6.5 |
|---|---|---|---|---|---|---|---|---|---|---|
| | Tg CDPK1 | Cp CDPK1 | SrcKD | AblKD | T. gondii | C. parvum | HepG2 | CRL 8155 | | |
| 1517 | 0.002 | 0.001 | >10 | >10 | 0.26 | 0.05 | >40 | >40 | >30 | 26 |
| 1543 | 0.005 | 0.003 | >10 | >10 | 0.59 | ND | >40 | >40 | ND | >100 |
| 1458 | 0.002 | 0.002 | 7 | 4.6 | 0.07 | 0.1 | >40 | >40 | >10 | 18 |
| 1473 | 0.004 | 0.004 | 7.3 | 5.1 | 0.47 | 0.05 | >40 | >30 | >10 | 15 |
| 1474 | 0.007 | 0.01 | 7.8 | >10 | 0.37 | ND | >40 | 38 | ND | 10 |
| 1566 | 0.005 | ND | >10 | >10 | 0.69 | ND | >40 | 16 | ND | 13 |
| 1571 | 0.007 | ND | 10 | >10 | 0.62 | ND | >40 | >40 | ND | 17 |
| 1572 | 0.006 | ND | >10 | >10 | 0.23 | ND | >40 | >40 | ND | 99 |

ND = not done

Pharmacokinetic (PK) studies in mice for several compounds of the disclosure are shown in Table 5. Maximum concentration ($C_{max}$), time at which is observed ($T_{max}$) and area under the curve (AUC) are evaluated for the dosage of 10 mg/kg.

TABLE 5

Pharmacokinetic studies in mice

| | | PK (10 mg/kg) | | |
|---|---|---|---|---|
| Entry No. | Comp. No. | $C_{max}$ (μM) | $T_{max}$ (min) | AUC (μM-min) |
| 1 | 1517 | 9.9 | 60 | 2449.6 |
| 2 | 1597 | 5.3 | 80 | 1693.6 |
| 3 | 1571 | 4.6 | 80 | 1608.1 |
| 4 | 1585 | 7.1 | 140 | 3713.2 |
| 5 | 1458 | 3.1 | 30 | 356.5 |

Example 106

Selectivity in a Panel of Kinases

The selectivity of compound 39 for CpCDPK1 was evaluated. In particular, the activity for CpCDPK1 was compared to the activity for over 20 representative kinases. The results are shown in Table 5.

TABLE 5

Selectivity of compound 39.

| Kinase | $IC_{50}$, μM | $K_i$, μM | $pK_i$ |
|---|---|---|---|
| CDPK1 | 0.0003 | 0.0008 | 9.52 |
| Prkcn | 1.11 | 0.427 | 6.37 |
| **Kdr | 2.46 | 0.569 | 6.24 |
| **EGFR | >10 | 1.67 | 5.78 |
| CAMK 1D^ | >10 | 2.48 | 5.61 |
| *MAP3K10 | >10 | 3.06 | 5.51 |
| CAMKK2^ | >10 | 3.1 | 5.51 |
| MEK1 | >10 | 3.29 | 5.48 |
| **BRAF | >10 | 3.37 | 5.47 |
| **Rock1 | >10 | 3.59 | 5.44 |
| **FLT1 | >10 | 3.67 | 5.44 |
| p38 alpha | >10 | 3.92 | 5.41 |
| **AUR1 | >10 | 4.05 | 5.39 |
| Ck1alpha1 | >10 | 4.12 | 5.39 |
| ACVR1 | >10 | 4.32 | 5.36 |
| *CAMK2A^ | >10 | 4.32 | 5.36 |
| *JAK3 | >10 | 4.79 | 5.32 |

TABLE 5-continued

Selectivity of compound 39.

| Kinase | IC$_{50}$, µM | K$_i$, µM | pK$_i$ |
|---|---|---|---|
| **Akt1 | >10 | 5.01 | 5.30 |
| Zipk^ | >10 | 5.41 | 5.27 |
| *ALK | >10 | 5.79 | 5.24 |
| **Erk2 | >10 | 6.6 | 5.18 |

**/*Denotes Kinases (**) or close relatives (*) whose inhibition causes cardiotoxicity
^Denotes human kinases that are most closely related to CDPK1.

Example 107

Crystal Structure of TgCDPK1-Compound Complex

A crystal structure of the TgCDPK1-35 complex at 2.0 Å was obtained. Superposition of the structures of TgCDPK1 in complex with 35 and with a PP analog 2 shows that the compound 35 core can preserve the projections of N1 and C3 substitutions as well as hydrogen bond interactions with TgCDPK1 seen for the PP core (FIG. 1). The amide group of the compound core is essentially on top of the aminopyrimidine moiety of the PP core. Further away, on the naphthyl/quinolinyl and t-butyl substitutions, the matching carbons are 0.5-0.6 Å apart. It is not clear if the deviations are caused by the difference in the aromatic rings or by the overall electronic configurations of the two inhibitors. The two series of inhibitors have different tolerance of methyl piperidine substituents on the N1 position (i.e., $R^2$) since these substitutions project distally into the ribose binding pocket and the solvent.

Example 108

T. gondii Infection in Mice

Figure 2:
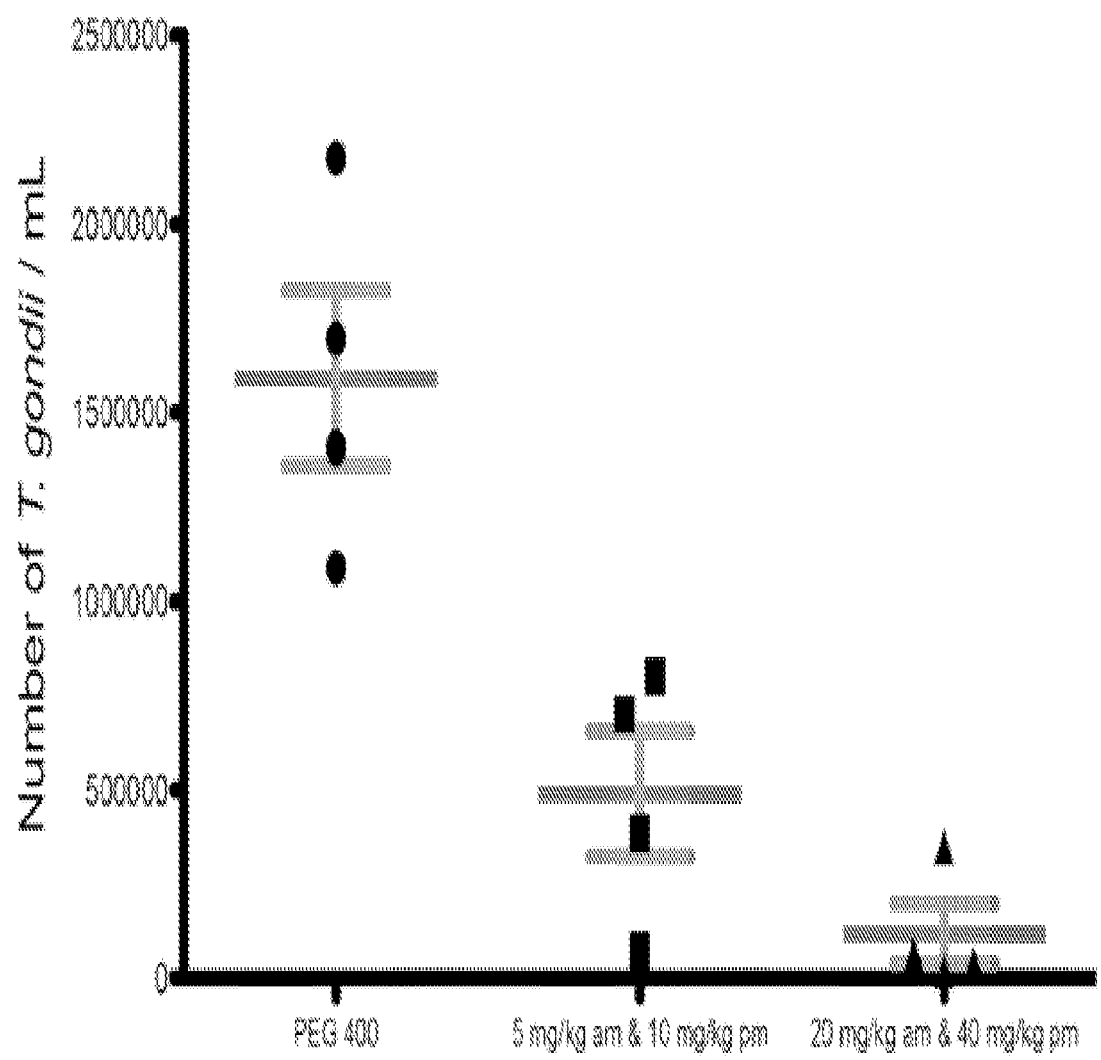
FIG. 2 illustrates compound 39 (1517) treatment of *Toxoplasma* infection in mice.

1×10$^5$ T. gondii Type 1 RH strain tachyzoites expressing YFP were inoculated i.p. into 4-5 wk old female CF-1 mice (n=4). After 48 h, compound 39 or vehicle-alone (PEG 400) were administered via oral gavage at 8 AM and 5 PM for 5 d. On day 8, the mice were killed, and underwent peritoneal lavage. T. gondii were enumerated via fluorescent microscopy and plotted, per mouse. Results are shown in FIG. 2. A dose response in efficacy was seen in that the mean parasite burden was decreased by 69% in the 5/10 mg/kg [AM/PM] group and 93% in the 20/40 mg/kg group.

Example 109

C. parvum Infection in Mice

Figure 3:
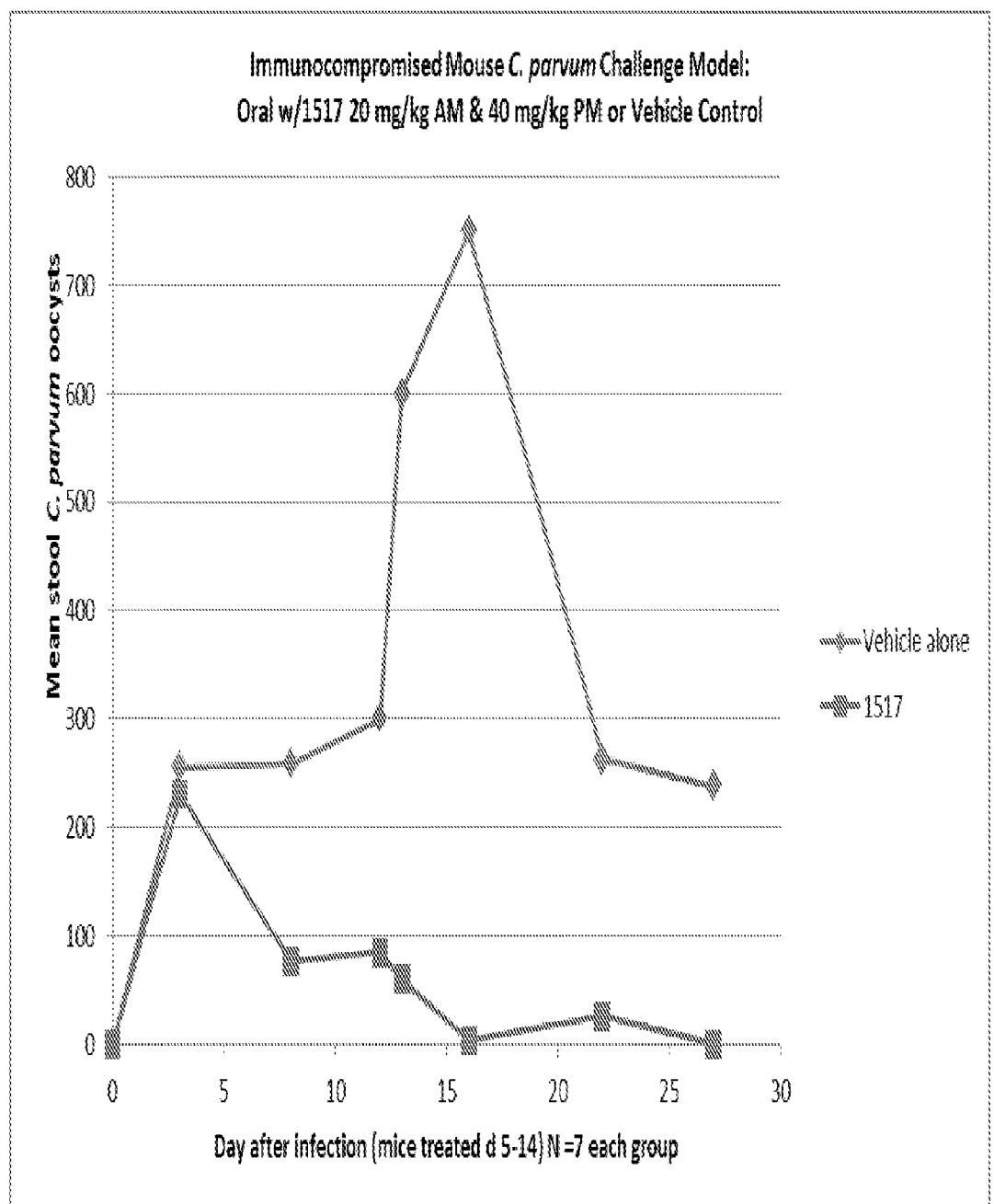
FIG. 3 illustrates the effects of treatment with compound 39 in a beige/SCID mouse model of *C. parvum* infection.

Mice (7 wk old) were infected with 10$^6$ oocysts of C. parvum Iowa strain by oral gavage. Mean oocysts shed in 250 mg mouse stool are shown from mice treated with compound 39 (1517) (squares, N=7) or vehicle alone (diamonds, N=7) are shown for each time point. Compound 39-treated mice were oral gavaged with compound 39 at a dose of 20 mg/kg at 8 AM and 40 mg/kg at 5 PM on days 5-14 after infection. Control mice were given vehicle alone by oral gavage at 8 AM and 5 PM on days 5-14 after infection). The number of oocysts in treated and vehicle groups was quantified by qRT-PCR and normalized to the number of oocysts using a standard curve. Differences between groups were compared at each time point and p values calculated by non-parametric analysis of Kruskal-Wallis and for each time point, except before treatment (Days 0 and 3), the difference was significant (p≤0.05). The results are illustrated in FIG. 3.

Additional Results:

In addition to these positive therapeutic tests in vivo, compound 39 (1517) has been found to have parameters consistent with CNS penetration (necessary for T. gondii therapeutics). These included excellent diffusion across the MDCK-PGP monolayer that predicts CNS penetration (=563 nm/sec, similar to a positive control CNS penetrant molecule) and 25% brain levels/plasma levels in orally-dosed mice at 1 hour after dosing. Finally, compound 39 (1517) has been tested by AbbVie in their panel of 80 human protein kinases (hPKs) and 24 off-target liabilities (e.g. ion channels, G-protein receptors). No hPKs were inhibited at levels up to 3 µM and no signal was detected in the 24 off-target liability screen. These results demonstrate that the compounds of the disclosure can be specific for CDPKs.

In addition, compound 39 (1517) has shown good solubility, good stability, and higher oral availability than the compound of prior art, 3-(6-ethoxynaphthalen-2-yl)-1-((1-methylpiperidin-4-yl)methyl)-1H-pyrazolo[3,4-d]pyrimidin-4-amine (compound 9, also 1294). In addition, hERG inhibition has been associated with long Q-T syndrome (cardiotoxicity), and compounds without the recombinant hERG binding present better clinical candidates. Indeed, compound 39 (1517) has shown no hERG inhibitory activity as compared to compound 9 (1294).

Example 110

Efficacy in Calf Model

The calf model is a clinical model of C. parvum, as calves develop profuse watery diarrhea commencing 2-3 days PI which peaks around day 7-8. Diarrhea is less severe or sometimes resolved by day 10 PI. A total of six male calves per treatment or control group are used, allowing potential exclusion of up to one animal from each group without compromising statistical analyses. All calves are sourced from the same closed herd of approximately 12,000 Holstein dairy cows at Shamrock Dairy (Casa Grande, Ariz.). Beginning at 12 h of age, calves are maintained on milk replacer twice daily until end of the experiment at day 10 post challenge. For efficacy evaluation against C. parvum, each calf is challenged by oral inoculation with 3×10$^7$ oocysts on day 0, when 36-48 h of age. At challenge and every 12 h thereafter until the end of the experiment, calves are orally administered an individual BKI. Dosages of 10 mg/kg/day and 100 mg/kg/day are evaluated, but the actual dosage and intervals may be modified based on expected PK from allometric dose adjustments, the compound protein binding of calf plasma, and the relative metabolism of compounds by bovine liver microsomes. Control calves are identically infected and treated with vehicle alone. Fecal samples are examined for oocysts prior to challenge and daily thereafter to determine pre-patent and patent periods. Total daily oocyst counts for each calf are determined by real-time PCR using feces collected over successive 24 h periods. Clinical and parasitological data is analyzed statistically by ANOVA using the General Linear Modes Program. Fecal samples are collected at 80 h post challenge for measurement of stool BKI content (control: pre-infection stools). Plasma BKI levels are measured from calves at the first and last peaks and troughs. Blood is collected at the end of BKI dosing for CBC and a complete metabolic profile to screen for toxicity. Calves are euthanized on day 10 PI. Tissues are evaluated for toxicologic pathology. Feces from each calf are examined for possible bacterial and viral enteropathogens by standard methods operative in the Arizona Veterinary Diagnostic Laboratory.

Example 111

Efficacy in Sheep Model

Pregnant sheep are selected from a high health status closed pure Churra breed flock. For each compound, enough number of sheep are oestrus synchronized and fertilized through programmed mating in the flock Pregnancy diagnose are carried out through ultrasound scan (US) at 40 days of gestation. Each group consists of two pregnant sheep. Rectal temperatures are recorded 2 days before drug supplying and then daily during the experiment. Blood samples are taken weekly and analyzed to monitor health status. Sheep are also monitored by ultrasound scan (US) weekly throughout the experiment until lambing or fetal death. When this occurs, sheep and lamb/fetus are euthanized and complete PM carried out. Blood is collected pre-dosing (control), and after the first and fifth dosage, 1, 2, 4, 8 and 24 hrs (48 hrs for every other dosing). Blood is collected with EDTA and plasma separated. Three days after the end of the exposure, blood is worked up for a complete blood count and full chemistry and the animals are sacrificed and liver, kidney, muscle, and placenta are examined histologically for toxicity.

For testing each compound, pregnant sheep are randomly allocated in different groups: 1) treated and challenged with *N. caninum;* 2) treated and challenged with *T. gondii;* 3) non-treated and challenged with *N. caninum;* 4) non-treated and challenged with *T. gondii;* 5) treated and non-challenged; and 6) non-treated, non-challenged. Each group is composed of seven sheep. Treatments are supplied from day 5 to day 15 after infection on animals from groups 1, 2 and 5, following the schedule estimated from the results obtained above in the PK studies to give values above the EC90 for the organism throughout the dosing interval. Animals in groups 3, 4 and 6 remain untreated. On day 90 of gestation, sheep to be infected with *N. caninum* (groups 1 and 3), is inoculated intravenously (i.v.) with 2 ml PBS containing $10^6$ live *N. caninum* tachyzoites of the Nc-Spain7 isolate. Sheep to be infected with *T. gondii* (groups 2 and 4) are orally inoculated with 50 sporulated oocysts of the M4 isolate. The animals from group 4 do not receive any drug treatment and will be administered orally with PBS (diluent of *T. gondii* oocysts) and the animals in group 2 are inoculated intravenously with a comparable number of cells from the same cell-line used as host cell for growth of *N. caninum* tachyzoites. Rectal temperatures are recorded 2 days before inoculation and then daily until 14 days post infection (p.i.), later once a week. Blood samples are taken weekly and analyzed to monitor health status. Heparinised blood and serum are also taken to monitor specific immune responses against the parasites. Lambs and dams are culled at day 7 after birth or immediately after detection of fetal mortality. Samples are collected for histopathological, PK analyses and PCR-parasite detection and quantification. A sample of thoracic liquid from aborted fetuses of precalostral serum from lambs is collected for serology. Antibody responses, cellular immune responses (IFN-γ), histopathology, and DNA extraction of tissue samples/*Neospora* and *Toxoplasma* PCRs are evaluated.

It is understood that the examples and embodiments described herein are for illustrative purposes only and that various modifications or changes in light thereof will be suggested to persons skilled in the art and are to be incorporated within the spirit and purview of this application and scope of the appended claims. All publications, patents, and patent applications cited herein are hereby incorporated herein by reference for all purposes.

We claim:

1. A compound of the formula:

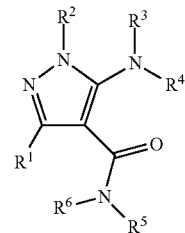

or a pharmaceutically acceptable salt thereof, wherein $R^1$ is one of the formulas:

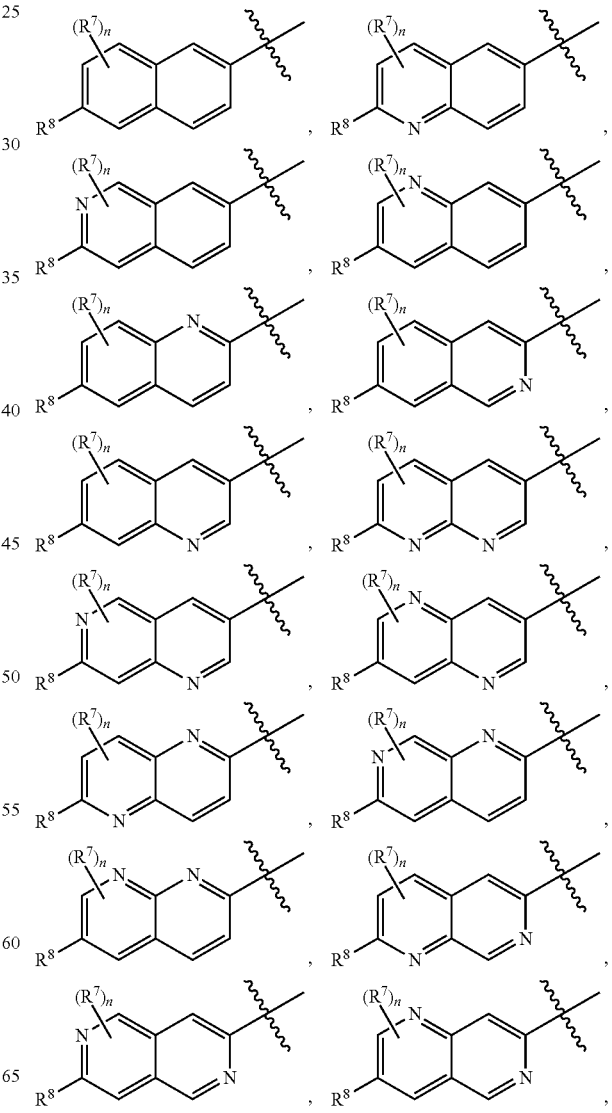

-continued

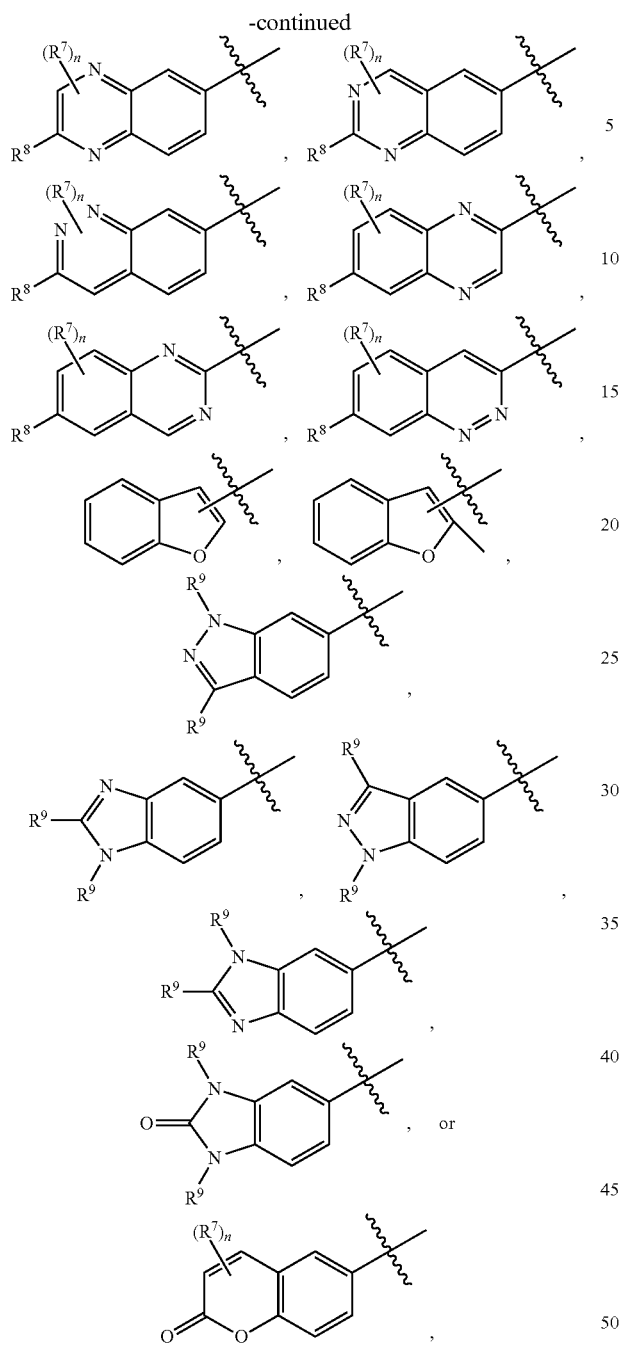

wherein
n is 0;
each $R^7$ is independently halogen, cyano, nitro, $C_{1-6}$ alkyl, $C_{1-6}$ haloalkyl, —$OR^{10}$, —$SR^{10}$, —$N(R^{10})_2$, —$C(O)R^{10}$, —$C(O)OR^{10}$, —$C(O)N(R^{10})_2$, —$S(O)_2R^{10}$, —$OC(O)R^{10}$, —$OC(O)OR^{10}$, —$OC(O)N(R^{10})_2$, —$N(R^{10})C(O)R^{10}$, —$N(R^{10})C(O)OR^{10}$, or —$N(R^{10})C(O)N(R^{10})_2$, wherein each $R^{10}$ is independently hydrogen or $C_{1-6}$ alkyl;
$R^8$ is halogen, cyano, nitro, $C_{1-6}$ alkyl, $C_{1-6}$ haloalkyl, or -Q-$R^{8'}$;
Q is —O—, —S—, —NH—, or —N($C_{1-6}$ alkyl)-;
$R^{8'}$ is hydrogen, $C_{1-6}$ alkyl, $C_{2-6}$ alkenyl, $C_{1-6}$ haloalkyl, $C_{3-8}$ cycloalkyl, heterocyclyl, aryl, aryl$C_{1-6}$ alkyl, heteroaryl, or heteroaryl$C_{1-6}$ alkyl, wherein the alkyl, aryl, arylalkyl, heteroaryl, and heteroarylalkyl are optionally substituted with one, two, three, or four groups that are each independently halogen, cyano, nitro, $C_{1-6}$ alkyl, $C_{1-6}$ haloalkyl, —$OR^{14}$, —$SR^{14}$, —$N(R^{14})_2$, —$C(O)R^{14}$, —$C(O)OR^{14}$, —$C(O)N(R^{14})_2$, —$S(O)_2R^{14}$, —$OC(O)R^{14}$, —$OC(O)OR^{14}$, —$OC(O)N(R^{14})_2$, —$N(R^{14})C(O)R^{14}$, —$N(R^{14})C(O)OR^{14}$, or —$N(R^{14})C(O)N(R^{14})_2$, wherein each $R^{14}$ is independently hydrogen or $C_{1-6}$ alkyl; and
each $R^9$ is independently hydrogen or $C_{1-6}$ alkyl;
$R^2$ is hydrogen, $C_{1-6}$ alkyl, $C_{1-6}$ haloalkyl, —$C_{1-4}$ alkyl-$R^{12}$, $C_{2-6}$ alkenyl, $C_{2-6}$ alkynyl, $C_{3-8}$ cycloalkyl, monocyclic heterocyclyl, monocyclic heteroaryl, or phenyl, wherein the alkyl, cycloalkyl, heterocyclyl, heteroaryl, and phenyl groups are each optionally substituted with one or two $R^{13}$ groups;
each $R^{13}$ is independently $C_{1-6}$ alkyl, $C_{1-6}$ haloalkyl, —OR, —SR, —$NR_2$, —C(O)R, —C(O)OR, —C(O)$NR_2$, —$S(O)_2NR_2$, or —$S(O)_2R$; and
where $R^{12}$ is —OR, —SR, —$NR_2$, —C(O)R, —C(O)OR, —C(O)$NR_2$, —$S(O)_2R$, —OC(O)R, —OC(O)OR, —OC(O)$NR_2$, —N(R)C(O)R, —N(R)C(O)OR, —N(R)C(O)$NR_2$, phenyl, monocyclic heteroaryl, $C_{3-8}$ cycloalkyl, or monocyclic heterocyclyl, wherein the aryl, heteroaryl, $C_{3-8}$ cycloalkyl, and heterocyclyl groups are each optionally substituted by one, two, or three groups that are each independently halogen, cyano, nitro, $C_{1-6}$ alkyl, $C_{1-6}$ haloalkyl, —OR, —SR, —$NR_2$, —C(O)R, —C(O)OR, —C(O)$NR_2$, —$S(O)_2R$, —OC(O)R, —OC(O)OR, —OC(O)$NR_2$, —N(R)C(O)R, —N(R)C(O)OR, or —N(R)C(O)$NR_2$;
and each R is independently hydrogen, $C_{1-6}$ alkyl, $C_{2-6}$ alkenyl, $C_{1-6}$ haloalkyl, $C_{3-8}$ cycloalkyl, heterocyclyl, aryl, aryl$C_{1-6}$ alkyl, heteroaryl, or heteroaryl$C_{1-6}$ alkyl, wherein the alkyl, aryl, arylalkyl, heteroaryl, and heteroarylalkyl are optionally substituted with one, two, three, or four groups that are each independently halogen, cyano, nitro, $C_{1-6}$ alkyl, $C_{1-6}$ haloalkyl, —$OR^o$, —$SR^o$, —$N(R^o)_2$, —$C(O)R^o$, —$C(O)OR^o$, —$C(O)N(R^o)_2$, —$S(O)_2R^o$, —$OC(O)R^o$, —$OC(O)OR^o$, —$OC(O)N(R^o)_2$, —$N(R^o)C(O)R^o$, —$N(R^o)C(O)OR^o$, or —$N(R^o)C(O)N(R^o)_2$, wherein each $R^o$ is independently hydrogen or $C_{1-6}$ alkyl;
or $R^2$ and $R^3$ together with the atoms to which they are attached form 2-oxo-2,3-dihydro-imidazolyl ring;
$R^3$ and $R^4$ are independently hydrogen; and
$R^5$ and $R^6$ are independently hydrogen.

2. A compound according to claim 1, wherein R is one of the formulas:

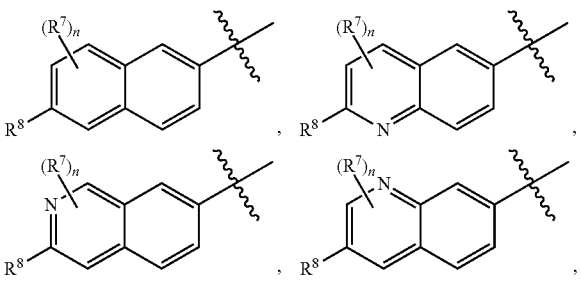

-continued

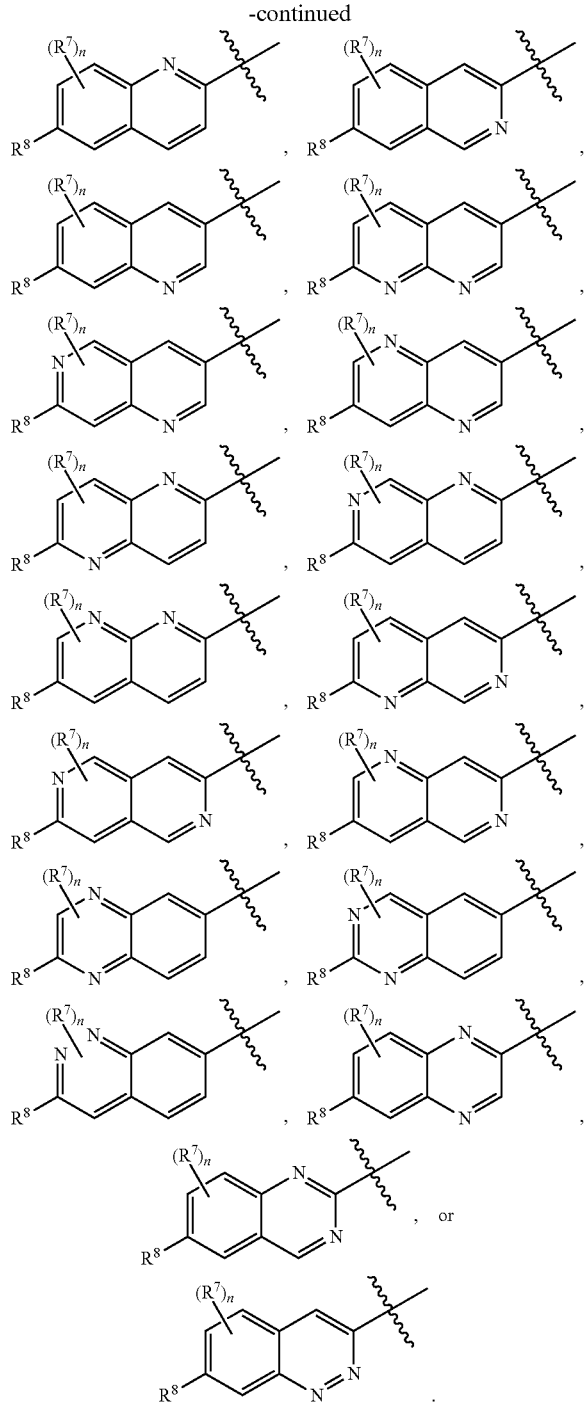

3. A compound according to claim 2, wherein $R^8$ is -Q-$R^{8'}$; wherein

Q is —O—, —S—, —NH—, or —N($C_{1-6}$ alkyl)-;

$R^{8'}$ is hydrogen, $C_{1-6}$ alkyl, $C_{2-6}$ alkenyl, $C_{1-6}$ haloalkyl, $C_{3-8}$ cycloalkyl, heterocyclyl, aryl, aryl$C_{1-6}$ alkyl, heteroaryl, or heteroaryl$C_{1-6}$ alkyl wherein the alkyl, aryl, arylalkyl, heteroaryl, and heteroarylalkyl are optionally substituted with one, two, three, or four groups that are each independently halogen, cyano, nitro, $C_{1-6}$ alkyl, $C_{1-6}$ haloalkyl, —OR$^{14}$, —SR$^{14}$, —N(R$^{14}$)$_2$, —C(O)R$^{14}$, —C(O) OR$^{14}$, —C(O)N(R$^{14}$)$_2$, —S(O)$_2$R$^{14}$—OC(O)OR$^{14}$, —OC(O)N(R$^{14}$)$_2$, —N(R$^{14}$)C(O)R$^{14}$, —N(R$^{14}$)C(O)OR$^{14}$, or —N(R$^{14}$)C(O)N(R$^{14}$)$_2$, wherein each $R^{14}$ is independently hydrogen or $C_{1-6}$ alkyl.

4. A compound according to claim 2, wherein $R^8$ is halogen, $C_{1-6}$ alkyl, or $C_{1-6}$ haloalkyl.

5. A compound according to claim 1, wherein $R^1$ is one of the formulas:

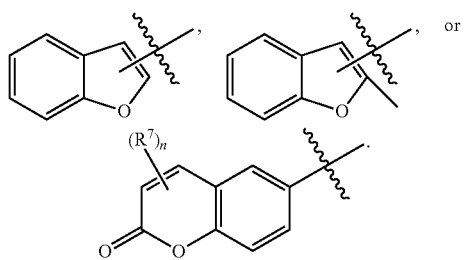

6. A compound according to claim 1, wherein each $R^7$ is independently halogen, cyano, nitro, $C_{1-6}$ alkyl, $C_{1-6}$ haloalkyl, —OR$^{10}$, —SR$^{10}$, —N(R$^{10}$)$_2$, —C(O)R$^{10}$, —C(O)OR$^{10}$, or —C(O)N(R$^{10}$)$_2$, wherein each $R^{10}$ is independently hydrogen or $C_{1-6}$ alkyl.

7. A compound according to claim 6, wherein each $R^7$ is independently halogen, cyano, nitro, $C_{1-6}$ alkyl, or $C_{1-6}$ haloalkyl.

8. A compound according to claim 1, wherein $R^1$ is one of the formulas:

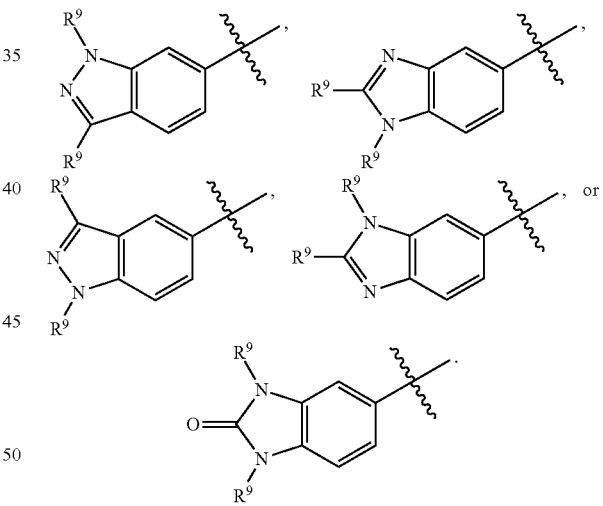

9. A compound according to claim 1, wherein each $R^9$ is independently hydrogen or $C_{1-4}$ alkyl.

10. A compound according to claim 9, wherein each $R^9$ is independently hydrogen or methyl.

11. A compound according to claim 1, wherein $R^2$ is $C_{1-6}$ alkyl, $C_{1-6}$ haloalkyl, —$C_{1-4}$ alkyl-$R^{12}$, $C_{2-6}$ alkenyl, $C_{2-6}$ alkynyl, $C_{3-8}$ cycloalkyl, monocyclic heterocyclyl, monocyclic heteroaryl, or phenyl, wherein the alkyl, cycloalkyl, heterocyclyl, heteroaryl, and phenyl groups are each optionally substituted with one or two $R^{13}$ groups.

12. A compound according to claim 11, where $R^{12}$ is —OR, —NR$_2$, —C(O)R, —C(O)OR, —C(O)NR$_2$, —S(O)$_2$R, phenyl, monocyclic heteroaryl, $C_{3-8}$ cycloalkyl, or monocyclic heterocyclyl, wherein the aryl, heteroaryl, $C_{3-8}$ cycloalkyl, and heterocyclyl groups are each optionally substituted by one, two, or three groups that are each independently halogen, cyano, nitro, $C_{1-6}$ alkyl, $C_{1-6}$ haloalkyl, —OR, —SR, —$NR_2$, —C(O)R, —C(O)OR, —C(O)$NR_2$, —S(O)$_2$R, —OC(O)R, —OC(O)OR, —OC(O)$NR_2$, —N(R)C(O)R, —N(R)C(O)OR, or —N(R)C(O)$NR_2$.

13. A compound according to claim 12, where $R^{12}$ is —OR.

14. A compound according to claim 1, wherein $R^2$ is $C_{3-8}$ cycloalkyl or monocyclic heterocyclyl, each optionally substituted with one or two $R^{13}$ groups.

15. A compound, which is:
5-amino-1-tert-butyl-3-(6-ethoxynaphthalen-2-yl)-1H-pyrazole-4-carboxamide;
1-tert-butyl-3-(6-ethoxynaphthalen-2-yl)-1H-pyrazole-4-carboxamide;
5-amino-3-(naphthalen-2-yl)-1-(piperidin-4-ylmethyl)-1H-pyrazole-4-carboxamide;
5-amino-3-(6-ethoxynaphthalen-2-yl)-1-((1-methylpiperidin-4-yl)methyl)-1H-pyrazole-4-carboxamide;
5-amino-3-(6-methoxynaphthalen-2-yl)-1-((1-methylpiperidin-4-yl)methyl)-1H-pyrazole-4-carboxamide;
5-amino-3-(6-methoxynaphthalen-2-yl)-1H-pyrazole-4-carboxamide;
5-amino-1-ethyl-3-(naphthalen-2-yl)-1H-pyrazole-4-carboxamide;
5-amino-1-isopropyl-3-(naphthalen-2-yl)-1H-pyrazole-4-carboxamide;
5-amino-1-isobutyl-3-(naphthalen-2-yl)-1H-pyrazole-4-carboxamide;
5-amino-1-(cyclopropylmethyl)-3-(naphthalen-2-yl)-1H-pyrazole-4-carboxamide;
5-amino-1-(cyclohexylmethyl)-3-(naphthalen-2-yl)-1H-pyrazole-4-carboxamide;
5-amino-1-cyclohexyl-3-(naphthalen-2-yl)-1H-pyrazole-4-carboxamide;
5-amino-3-(naphthalen-2-yl)-1-(2,2,2-trifluoroethyl)-1H-pyrazole-4-carboxamide;
5-amino-3-(naphthalen-2-yl)-1-neopentyl-1H-pyrazole-4-carboxamide;
5-amino-1-(1-methylpiperidin-4-yl)-3-(naphthalen-2-yl)-1H-pyrazole-4-carboxamide;
5-amino-1-((1-methylpiperidin-4-yl)methyl)-3-(naphthalen-2-yl)-1H-pyrazole-4-carboxamide;
5-amino-1-(2-hydroxyethyl)-3-(naphthalen-2-yl)-1H-pyrazole-4-carboxamide;
5-amino-1-(2-morpholinoethyl)-3-(naphthalen-2-yl)-1H-pyrazole-4-carboxamide;
5-amino-1-(tert-butyl)-3-(6-hydroxynaphthalen-2-yl)-1H-pyrazole-4-carboxamide;
5-amino-1-(tert-butyl)-3-(6-methoxynaphthalen-2-yl)-1H-pyrazole-4-carboxamide;
5-amino-1-(tert-butyl)-3-(6-propoxynaphthalen-2-yl)-1H-pyrazole-4-carboxamide;
5-amino-1-(tert-butyl)-3-(2-methylbenzofuran-3-yl)-1H-pyrazole-4-carboxamide;
3-(3-amino-1H-indazol-6-yl)-1-(tert-butyl)-1H-pyrazole-4-carboxamide;
3-(3-amino-1-methyl-1H-indazol-6-yl)-1-(tert-butyl)-1H-pyrazole-4-carboxamide;
5-amino-1-(tert-butyl)-3-(1-methyl-1H-indazol-5-yl)-1H-pyrazole-4-carboxamide;
5-amino-1-(tert-butyl)-3-(1-methyl-2-oxo-2,3-dihydro-1H-benzo[d]imidazol-5-yl)-1H-pyrazole-4-carboxamide;
5-amino-1-(tert-butyl)-3-(1,2-dimethyl-1H-benzo[d]imidazol-5-yl)-1H-pyrazole-4-carboxamide;
5-amino-3-(2-amino-1-methyl-1H-benzo[d]imidazol-5-yl)-1-(tert-butyl)-1H-pyrazole-4-carboxamide;
5-amino-1-(tert-butyl)-3-(2-oxo-2H-chromen-6-yl)-1H-pyrazole-4-carboxamide;
5-amino-1-(tert-butyl)-3-(quinolin-2-yl)-1H-pyrazole-4-carboxamide;
5-amino-1-(tert-butyl)-3-(6-ethoxyquinolin-2-yl)-1H-pyrazole-4-carboxamide;
5-amino-1-(tert-butyl)-3-(quinolin-6-yl)-1H-pyrazole-4-carboxamide;
5-amino-1-(tert-butyl)-3-(quinolin-3-yl)-1H-pyrazole-4-carboxamide;
5-amino-1-(tert-butyl)-3-(7-ethoxyquinolin-3-yl)-1H-pyrazole-4-carboxamide;
5-amino-3-(7-ethoxyquinolin-3-yl)-isopropyl-1H-pyrazole-4-carboxamide;
5-amino-3-(7-ethoxyquinolin-3-yl)-isobutyl-1H-pyrazole-4-carboxamide;
5-amino-3-(7-ethoxyquinolin-3-yl)-1-neopentyl-1H-pyrazole-4-carboxamide;
5-amino-3-(7-ethoxyquinolin-3-yl)-1-(2,2,2-trifluoroethyl)-1H-pyrazole-4-carboxamide;
5-amino-1-(cyclopropylmethyl)-3-(7-ethoxyquinolin-3-yl)-1H-pyrazole-4-carboxamide;
1-isobutyl-3-(2-(2,2,2-trifluoroethoxy)quinolin-6-yl)-1H-pyrazolo[3,4-d]pyrimidin-4-amine;
5-amino-1-cyclopentyl-3-(7-ethoxyquinolin-3-yl)-1H-pyrazole-4-carboxamide;
5-amino-1-cyclohexyl-3-(7-ethoxyquinolin-3-yl)-1H-pyrazole-4-carboxamide;
5-amino-3-(7-ethoxyquinolin-3-yl)-1-(tetrahydro-2H-pyran-4-yl)-1H-pyrazole-4-carboxamide;
5-amino-1-cycloheptyl-3-(7-ethoxyquinolin-3-yl)-1H-pyrazole-4-carboxamide;
5-amino-1-(cyclohexylmethyl)-3-(7-ethoxyquinolin-3-yl)-1H-pyrazole-4-carboxamide;
5-amino-3-(7-ethoxyquinolin-3-yl)-1-(1-hydroxypropan-2-yl)-1H-pyrazole-4-carboxamide;
5-amino-3-(7-ethoxyquinolin-3-yl)-1-(2-hydroxy-2-methylpropyl)-1H-pyrazole-4-carboxamide;
5-amino-3-(7-ethoxyquinolin-3-yl)-1-(4-hydroxybutan-2-yl)-1H-pyrazole-4-carboxamide;
5-amino-3-(7-ethoxyquinolin-3-yl)-1-(3-hydroxy-2,2-dimethylpropyl)-1H-pyrazole-4-carboxamide;
5-amino-1-(tert-butyl)-3-(2-ethoxyquinolin-6-yl)-1H-pyrazole-4-carboxamide;
5-amino-1-(cyclopropylmethyl)-3-(2-ethoxyquinolin-6-yl)-1H-pyrazole-4-carboxamide;
5-amino-1-cyclohexyl-3-(2-ethoxyquinolin-6-yl)-1H-pyrazole-4-carboxamide;
5-amino-1-cycloheptyl-3-(2-ethoxyquinolin-6-yl)-1H-pyrazole-4-carboxamide;
5-amino-3-(2-ethoxyquinolin-6-yl)-1-(3-hydroxy-2,2-dimethylpropyl)-1H-pyrazole-4-carboxamide;
5-amino-1-tert-butyl-3-(7-fluoroquinolin-3-yl)-1H-pyrazole-4-carboxamide;
5-amino-1-tert-butyl-3-(7-chloroquinolin-3-yl)-1H-pyrazole-4-carboxamide;
5-amino-1-tert-butyl-3-(7-(trifluoromethyl)quinolin-3-yl)-1H-pyrazole-4-carboxamide;
5-amino-1-tert-butyl-3-(7-methylquinolin-3-yl)-1H-pyrazole-4-carboxamide;
5-amino-1-tert-butyl-3-(7-ethylquinolin-3-yl)-1H-pyrazole-4-carboxamide;

5-amino-1-tert-butyl-3-(7-methoxyquinolin-3-yl)-1H-pyrazole-4-carboxamide;
5-amino-1-tert-butyl-3-(7-(trifluoromethoxy)quinolin-3-yl)-1H-pyrazole-4-carboxamide;
5-amino-1-(tert-butyl)-3-(7-isopropoxyquinolin-3-yl)-1H-pyrazole-4-carboxamide;
5-amino-1-tert-butyl-3-(7-propoxyquinolin-3-yl)-1H-pyrazole-4-carboxamide;
5-amino-1-(tert-butyl)-3-(7-(cyclopropylmethoxy)quinolin-3-yl)-1H-pyrazole-4-carboxamide;
5-amino-1-(tert-butyl)-3-(7-cyclopropoxyquinolin-3-yl)-1H-pyrazole-4-carboxamide;
5-amino-1-(tert-butyl)-3-(2-cyclopropoxyquinolin-6-yl)-1H-pyrazole-4-carboxamide;
5-amino-1-(tert-butyl)-3-(7-cyclobutoxyquinolin-3-yl)-1H-pyrazole-4-carboxamide;
5-amino-1-(tert-butyl)-3-(2-cyclobutoxyquinolin-6-yl)-1H-pyrazole-4-carboxamide;
5-amino-3-(7-cyclobutoxyquinolin-3-yl)-1-cyclobutyl-1H-pyrazole-4-carboxamide;
5-amino-3-(2-cyclobutoxyquinolin-6-yl)-1-cyclobutyl-1H-pyrazole-4-carboxamide;
5-amino-3-(7-cyclobutoxyquinolin-3-yl)-1-cyclopentyl-1H-pyrazole-4-carboxamide;
5-amino-3-(2-cyclobutoxyquinolin-6-yl)-1-cyclopentyl-1H-pyrazole-4-carboxamide;
5-amino-3-(7-cyclobutoxyquinolin-3-yl)-1-cyclohexyl-1H-pyrazole-4-carboxamide;
5-amino-3-(2-cyclobutoxyquinolin-6-yl)-1-cyclohexyl-1H-pyrazole-4-carboxamide;
5-amino-3-(7-cyclobutoxyquinolin-3-yl)-1-(3-hydroxy-2,2-dimethylpropyl)-1H-pyrazole-4-carboxamide;
5-amino-3-(2-cyclobutoxyquinolin-6-yl)-1-(3-hydroxy-2,2-dimethylpropyl)-1H-pyrazole-4-carboxamide;
5-amino-1-(tert-butyl)-3-(7-(2-methoxyethoxy)quinolin-3-yl)-1H-pyrazole-4-carboxamide;
5-amino-3-(7-ethoxyquinolin-3-yl)-1-(2-hydroxyethyl)-1H-pyrazole-4-carboxamide;
5-amino-1-(tert-butyl)-3-(7-(neopentyloxy)quinolin-3-yl)-1H-pyrazole-4-carboxamide;
5-amino-1-(tert-butyl)-3-(7-isobutoxyquinolin-3-yl)-1H-pyrazole-4-carboxamide;
5-amino-3-(7-ethoxyquinolin-3-yl)-1H-pyrazole-4-carboxamide;
5-amino-3-(7-ethoxyquinolin-3-yl)-1-(2-methoxyethyl)-1H-pyrazole-4-carboxamide;
5-amino-3-(7-ethoxyquinolin-3-yl)-N,1-bis(2-methoxyethyl)-1H-pyrazole-4-carboxamide;
5-amino-1-(2,4-dimethylpentan-3-yl)-3-(7-ethoxyquinolin-3-yl)-1H-pyrazole-4-carboxamide;
6-(7-ethoxyquinolin-3-yl)-2-oxo-2,3-dihydro-1H-imidazo[1,2-b]pyrazole-7-carboxamide;
5-amino-3-(7-ethoxyquinolin-3-yl)-1-(3-hydroxybutan-2-yl)-1H-pyrazole-4-carboxamide;
5-amino-3-(7-ethoxyquinolin-3-yl)-1-(tetrahydrofuran-3-yl)-1H-pyrazole-4-carboxamide;
5-amino-3-(7-ethoxyquinolin-3-yl)-1-(3-hydroxy-3-methylbutan-2-yl)-1H-pyrazole-4-carboxamide;
5-amino-3-(7-ethoxyquinolin-3-yl)-1-(3-methylbutan-2-yl)-1H-pyrazole-4-carboxamide;
5-amino-1-(1,3-dihydroxypropan-2-yl)-3-(7-ethoxyquinolin-3-yl)-1H-pyrazole-4-carboxamide;
5-amino-1-(1-cyclopropylethyl)-3-(7-ethoxyquinolin-3-yl)-1H-pyrazole-4-carboxamide;
5-amino-3-(2-ethoxyquinolin-6-yl)-1-(tetrahydrofuran-3-yl)-1H-pyrazole-4-carboxamide;
5-amino-3-(2-ethoxyquinolin-6-yl)-1-(3-hydroxy-3-methylbutan-2-yl)-1H-pyrazole-4-carboxamide;
5-amino-3-(7-ethoxyquinolin-3-yl)-1-(4-hydroxy-3,3-dimethylbutan-2-yl)-1H-pyrazole-4-carboxamide;
5-amino-3-(7-ethoxyquinolin-3-yl)-1-(1-methylcyclohexyl)-1H-pyrazole-4-carboxamide;
5-amino-1-(tert-butyl)-3-(6-ethoxyquinolin-3-yl)-1H-pyrazole-4-carboxamide;
5-amino-1-cyclohexyl-3-(6-ethoxyquinolin-3-yl)-1H-pyrazole-4-carboxamide;
5-amino-3-(2-ethoxyquinolin-6-yl)-isopropyl-1H-pyrazole-4-carboxamide;
or pharmaceutically acceptable salt thereof.

16. A pharmaceutical composition comprising one or more of compounds according to claim 1.

* * * * *